(12) United States Patent
Rommelaere et al.

(10) Patent No.: US 11,897,951 B2
(45) Date of Patent: Feb. 13, 2024

(54) POLYPEPTIDES COMPRISING IMMUNOGLOBULIN SINGLE VARIABLE DOMAINS TARGETING IL-6 AND TNF-α

(71) Applicants: Ablynx N.V., Zwijnaarde (BE); Sanofi, Paris (FR)

(72) Inventors: Heidi Rommelaere, Ghent (BE); Christian Asbrand, Frankfurt am Main (DE); Nadine Biesemann, Zwijnaarde (BE); Ann Brigé, Ertvelde (BE); Sigrid Cornelis, St. Martens-Lataem (BE); Karen Heyninck, Zwijnaarde (BE); Eric Lorent, Zwijnaarde (BE); Shanna Van Zwam, Ghent (BE)

(73) Assignees: Ablynx N.V., Zwijnaarde (BE); Sanofi, Paris (FR)

( * ) Notice: Subject to any disclaimer, the term of this patent is extended or adjusted under 35 U.S.C. 154(b) by 0 days.

(21) Appl. No.: 17/553,916

(22) Filed: Dec. 17, 2021

(65) Prior Publication Data
US 2022/0356241 A1 Nov. 10, 2022

Related U.S. Application Data
(60) Provisional application No. 63/167,925, filed on Mar. 30, 2021.

(30) Foreign Application Priority Data
Dec. 18, 2020 (EP) .................................. 20 306 612

(51) Int. Cl.
| C07K 16/24 | (2006.01) |
|---|---|
| A61P 29/00 | (2006.01) |
| C07K 16/28 | (2006.01) |

(52) U.S. Cl.
CPC ............ C07K 16/248 (2013.01); A61P 29/00 (2018.01); C07K 16/2875 (2013.01);
(Continued)

(58) Field of Classification Search
CPC .............. C07K 16/248; C07K 16/2875; C07K 2317/31; C07K 2317/565; C07K 2317/94; A61P 29/00
See application file for complete search history.

(56) References Cited

FOREIGN PATENT DOCUMENTS

| EP | 0 257 406 A2 | 3/1988 |
|---|---|---|
| EP | 0 312 996 A2 | 4/1989 |

(Continued)

OTHER PUBLICATIONS

Kussie PH, Parhami-Seren B, Wysocki LJ, Margolies MN. J Immunol. Jan. 1, 1994;152(1):146-52. PMID: 8254187. (Year: 1994).*
(Continued)

*Primary Examiner* — Adam Weidner
*Assistant Examiner* — Laura Ann Essex
(74) *Attorney, Agent, or Firm* — Wolf, Greenfield & Sacks, P.C.

(57) ABSTRACT

The present disclosure provides a novel type of drug for treating a subject suffering from an inflammatory and/or autoimmune disease, and specifically rheumatoid arthritis. Specifically, the disclosure provides polypeptides comprising at least three immunoglobulin single variable domains (ISVDs), characterized in that at least one ISVD binds to TNF-α and at least two ISVDs bind to IL-6. The present disclosure also provides nucleic acids, vectors and compositions.

Figure 1:
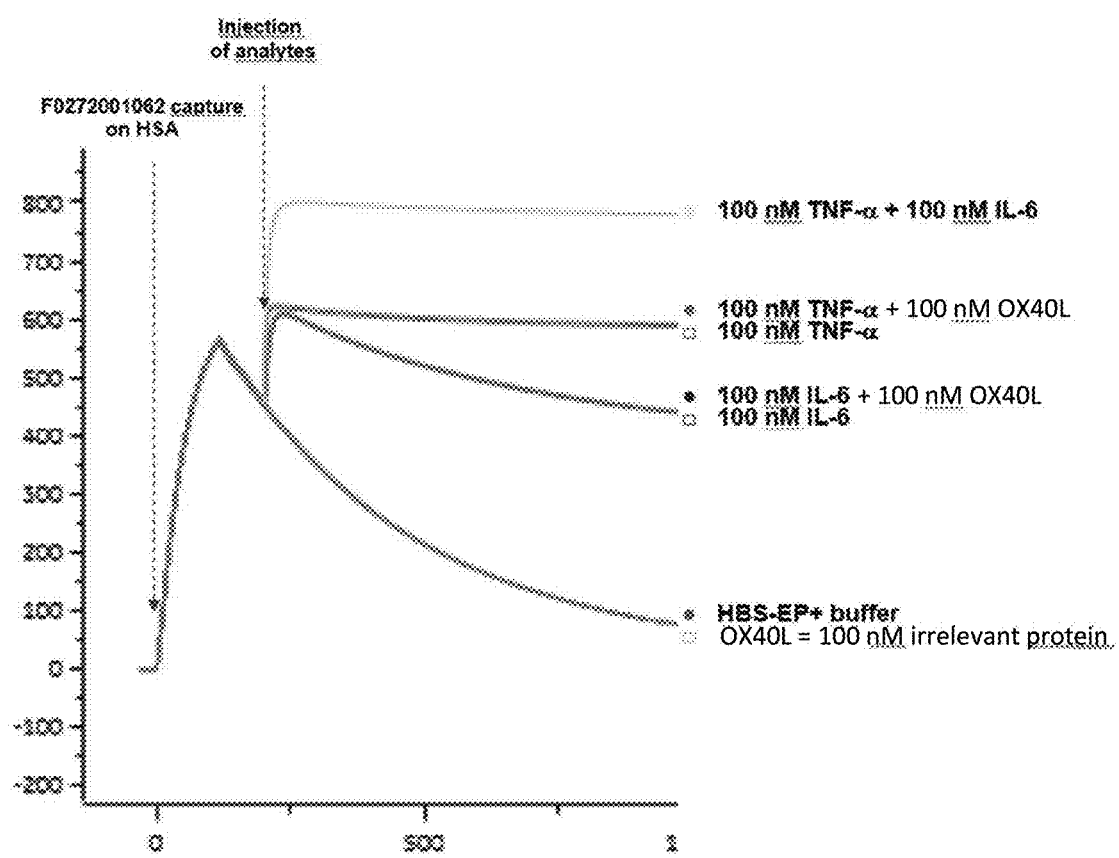

18 Claims, 23 Drawing Sheets
Specification includes a Sequence Listing.

(52) U.S. Cl.
CPC .... *C07K 2317/31* (2013.01); *C07K 2317/565* (2013.01); *C07K 2317/94* (2013.01)

(56) References Cited

FOREIGN PATENT DOCUMENTS

| | | |
|---|---|---|
| EP | 0 325 474 A2 | 7/1989 |
| EP | 0 409 607 A2 | 1/1991 |
| EP | 0 411 946 A2 | 2/1991 |
| EP | 0 572 118 A1 | 12/1993 |
| EP | 1 134 231 A1 | 9/2001 |
| WO | WO 1994/004678 A1 | 3/1994 |
| WO | WO 1994/025591 A1 | 11/1994 |
| WO | WO 1995/004079 A1 | 2/1995 |
| WO | WO 1996/034103 A1 | 10/1996 |
| WO | WO 1997/049805 A2 | 12/1997 |
| WO | WO 1999/023221 A2 | 5/1999 |
| WO | WO 1999/037681 A2 | 7/1999 |
| WO | WO 2000/040968 A1 | 7/2000 |
| WO | WO 2000/043507 A1 | 7/2000 |
| WO | WO 2000/065057 A1 | 11/2000 |
| WO | WO 2001/021817 A1 | 3/2001 |
| WO | WO 2001/040310 A2 | 6/2001 |
| WO | WO 2001/044301 A1 | 6/2001 |
| WO | WO 2001/090190 A2 | 11/2001 |
| WO | WO 2002/048193 A2 | 6/2002 |
| WO | WO 2003/025020 A1 | 3/2003 |
| WO | WO 2003/035694 A2 | 5/2003 |
| WO | WO 2003/050531 A2 | 6/2003 |
| WO | WO 2003/054016 A2 | 7/2003 |
| WO | WO 2003/055527 A2 | 7/2003 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/062551 A2 | 7/2004 |
| WO | WO 2005/044858 A1 | 5/2005 |
| WO | WO 2006/040153 A2 | 4/2006 |
| WO | WO 2006/079372 A1 | 8/2006 |
| WO | WO 2006/122786 A2 | 11/2006 |
| WO | WO 2006/122787 A1 | 11/2006 |
| WO | WO 2006/122825 A2 | 11/2006 |
| WO | WO 2007/104529 A2 | 9/2007 |
| WO | WO-2007104529 A2 * | 9/2007 ............... A61P 1/04 |
| WO | WO 2007/118670 A1 | 10/2007 |
| WO | WO 2008/020079 A1 | 2/2008 |
| WO | WO 2012/175400 A1 | 12/2012 |
| WO | WO 2012/175741 A2 | 12/2012 |
| WO | WO 2015/173325 A2 | 11/2015 |
| WO | WO 2017/068186 A1 | 4/2017 |
| WO | WO 2017/080850 A1 | 5/2017 |
| WO | WO 2017/085172 A2 | 5/2017 |
| WO | WO-2017081320 A1 * | 5/2017 ............... A61P 1/00 |
| WO | WO 2017/134234 A1 | 8/2017 |
| WO | WO 2018/104444 A1 | 6/2018 |
| WO | WO 2018/131234 A1 | 7/2018 |
| WO | WO 2018/134234 A1 | 7/2018 |
| WO | WO 2018/134235 A1 | 7/2018 |
| WO | WO-2018134235 A1 * | 7/2018 ............ C07K 16/18 |

OTHER PUBLICATIONS

Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*

EP 20306612.1, dated Oct. 28, 2021, Extended European Search Report.

Abdiche et al., Determining kinetics and affinities of protein interactions using a parallel real-time label-free biosensor, the Octet. Anal Biochem. Jun. 15, 2008;377(2):209-17. doi: 10.1016/j.ab.2008.03.035. Epub Mar. 25, 2008.

Atreya et al., Blockade of interleukin 6 trans signaling suppresses T-cell resistance against apoptosis in chronic intestinal inflammation: evidence in crohn disease and experimental colitis in vivo. Nat Med. May 2000;6(5):583-8. doi: 10.1038/75068. Erratum in: Nat Med. Nov. 2010;16(11):1341.

Bartok et al., Fibroblast-like synoviocytes: key effector cells in rheumatoid arthritis. Immunol Rev. Jan. 2010;233(1):233-55. doi: 10.1111/j.0105-2896.2009.00859.x.

Bataille et al., Biologic effects of anti-interleukin-6 murine monoclonal antibody in advanced multiple myeloma. Blood. Jul. 15, 1995;86(2):685-91.

Beck et al., Brief report: alleviation of systemic manifestations of Castleman's disease by monoclonal anti-interleukin-6 antibody. N Engl J Med. Mar. 3, 1994;330(9):602-5. doi: 10.1056/NEJM199403033300904.

Becker et al., TGF-beta suppresses tumor progression in colon cancer by inhibition of IL-6 trans-signaling. Immunity. Oct. 2004;21(4):491-501. doi: 10.1016/j.immuni.2004.07.020.

Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.

Choy et al., Therapeutic benefit of blocking interleukin-6 activity with an anti-interleukin-6 receptor monoclonal antibody in rheumatoid arthritis: a randomized, double-blind, placebo-controlled, dose-escalation trial. Arthritis Rheum. Dec. 2002;46(12):3143-50. doi: 10.1002/art.10623.

Conrath et al., Camel single-domain antibodies as modular building units in bispecific and bivalent antibody constructs. J Biol Chem. Mar. 9, 2001;276(10):7346-50. doi: 10.1074/jbc.M007734200. Epub Oct. 25, 2000.

Davies et al., 'Camelising' human antibody fragments: NMR studies on VH domains. FEBS Lett. Feb. 21, 1994;339(3):285-90. doi: 10.1016/0014-5793(94)80432-x.

Davies et al., Single antibody domains as small recognition units: design and in vitro antigen selection of camelized, human VH domains with improved protein stability. Protein Eng. Jun. 1996;9(6):531-7. doi: 10.1093/protein/9.6.531.

Doganci et al., The IL-6R alpha chain controls lung CD4+CD25+ Treg development and function during allergic airway inflammation in vivo. J Clin Invest. Feb. 2005;115(2):313-25. doi: 10.1172/JCI22433. Erratum in: J Clin Invest. May 2005;115(5):1388. Lehr, Hans A [added].

Drake et al., Characterizing high-affinity antigen/antibody complexes by kinetic- and equilibrium-based methods. Anal Biochem. May 1, 2004;328(1):35-43. doi: 10.1016/j.ab.2003.12.025.

Emilie et al., Administration of an anti-interleukin-6 monoclonal antibody to patients with acquired immunodeficiency syndrome and lymphoma: effect on lymphoma growth and on B clinical symptoms. Blood. Oct. 15, 1994;84(8):2472-9.

Fraley et al., The Gyrolab™ immunoassay system: a platform for automated bioanalysis and rapid sample turnaround. Bioanalysis. Jul. 2013;5(14):1765-74. doi: 10.4155/bio.13.145.

GBD 2015 Disease and Injury Incidence and Prevalence Collaborators. Global, regional, and national incidence, prevalence, and years lived with disability for 310 diseases and injuries, 1990-2015: a systematic analysis for the Global Burden of Disease Study 2015. Lancet. Oct. 8, 2016;388(10053):1545-1602. doi: 10.1016/S0140-6736(16)31678-6. Erratum in: Lancet. Jan. 7, 2017;389(10064):e1.

Glennie et al., Preparation and performance of bispecific F(ab' gamma)2 antibody containing thioether-linked Fab' gamma fragments. J Immunol. Oct. 1, 1987;139(7):2367-75.

Hamers-Casterman et al., Naturally occurring antibodies devoid of light chains. Nature. Jun. 3, 1993;363(6428):446-8. doi: 10.1038/363446a0.

Hirano et al., Purification to homogeneity and characterization of human B-cell differentiation factor (BCDF or BSFp-2). Proc Natl Acad Sci U S A. Aug. 1985;82(16):5490-4. doi: 10.1073/pnas.82.16.5490.

Holliger et al., Engineered antibody fragments and the rise of single domains. Nat Biotechnol. Sep. 2005;23(9):1126-36. doi: 10.1038/nbt1142.

Ishihara et al., Molecular basis of the cell specificity of cytokine action. Biochim Biophys Acta. Nov. 11, 2002;1592(3):281-96. doi: 10.1016/s0167-4889(02)00321-x.

(56) References Cited

OTHER PUBLICATIONS

Ito et al., A pilot randomized trial of a human anti-interleukin-6 receptor monoclonal antibody in active Crohn's disease. Gastroenterology. Apr. 2004;126(4):989-96; discussion 947. doi: 10.1053/j.gastro.2004.01.012.

Jang et al., Pharmacokinetic/pharmacodynamic (PK/PD) modeling and trial simulations to guide dose selection with CNTO 328, a chimeric anti-IL-6 monoclonal antibody (MAb), in patients with renal cell carcinoma (RCC). J Clin Oncol. 2004;22(14S):2608. 1 page.

Johnsson et al., Immobilization of proteins to a carboxymethyldextran-modified gold surface for biospecific interaction analysis in surface plasmon resonance sensors. Anal Biochem. Nov. 1, 1991;198(2):268-77. doi: 10.1016/0003-2697(91)90424-r.

Jonsson et al., Real-time biospecific interaction analysis using surface plasmon resonance and a sensor chip technology. Biotechniques. Nov. 1991;11(5):620-7.

Kabat et al., Sequences of Proteins of Immunological Interest. vol. I. 5th Ed. US Department of Health and Human Services. Public Health Service. National Institutes of Health. 1991. 11 pages.

Keffer et al., Transgenic mice expressing human tumour necrosis factor: a predictive genetic model of arthritis. EMBO J. Dec. 1991;10(13):4025-31.

Klareskog et al., Rheumatoid arthritis. Lancet. Feb. 21, 2009;373(9664):659-72. doi: 10.1016/S0140-6736(09)60008-8. Epub Jan. 20, 2009.

Klein et al., Design and characterization of structured protein linkers with differing flexibilities. Protein Eng Des Sel. Oct. 2014;27(10):325-30. doi: 10.1093/protein/gzu043.

Klein et al., Murine anti-interleukin-6 monoclonal antibody therapy for a patient with plasma cell leukemia. Blood. Sep. 1, 1991;78(5):1198-204.

Love et al., Moderated estimation of fold change and dispersion for RNA-seq data with DESeq2. Genome Biol. 2014;15(12):550. doi: 10.1186/s13059-014-0550-8.

Martin, Chapter 3: Protein Sequence and Structure Analysis of Antibody Variable Domains. In Antibody Engineering vol. 2. Springer Lab Manuals. Springer, Berlin, Heidelberg. 2010:33-51. doi: 10.1007/978-3-642-01147-4_3.

Muyldermans et al., Single domain camel antibodies: current status. J Biotechnol. Jun. 2001;74(4):277-302. doi: 10.1016/s1389-0352(01)00021-6.

Nishimoto et al., Humanized anti-interleukin-6 receptor antibody treatment of multicentric Castleman disease. Blood. Oct. 15, 2005;106(8):2627-32. doi: 10.1182/blood-2004-12-4602. Epub Jul. 5, 2005.

Nowell et al., Soluble IL-6 receptor governs IL-6 activity in experimental arthritis: blockade of arthritis severity by soluble glycoprotein 130. J Immunol. Sep. 15, 2003;171(6):3202-9. doi: 10.4049/jimmunol.171.6.3202.

Ober et al., Differences in promiscuity for antibody-FcRn interactions across species: implications for therapeutic antibodies. Int Immunol. Dec. 2001;13(12):1551-9. doi: 10.1093/intimm/13.12.1551.

Prabhakar et al., Correlation of serum CNTO 328-Anti IL-6 monoclonal antibody (MAb) concentrations and biomarker expression in renal cell carcinoma (RCC) patients. J Clin Oncol. 2004;22(14S):2560. 1 page.

Saito et al., Preparation of monoclonal antibodies against the IL-6 signal transducer, gp130, that can inhibit IL-6-mediated functions. J Immunol Methods. Aug. 9, 1993;163(2):217-23. doi: 10.1016/0022-1759(93)90125-q.

Schmidt et al., Complex human adenoid tissue-based ex vivo culture systems reveal anti-inflammatory drug effects on germinal center T and B cells. EBioMedicine. Mar. 2020;53:102684. doi: 10.1016/j.ebiom.2020.102684. Epub Feb. 27, 2020.

Shealy et al., Anti-TNF-alpha antibody allows healing of joint damage in polyarthritic transgenic mice. Arthritis Res. 2002;4(5):R7. doi: 10.1186/ar430. Epub Jun. 28, 2002.

Smolen et al., Rheumatoid arthritis. Nat Rev Dis Primers. Feb. 8, 2018;4:18001. doi: 10.1038/nrdp.2018.1.

Suematsu et al., Generation of plasmacytomas with the chromosomal translocation t(12;15) in interleukin 6 transgenic mice. Proc Natl Acad Sci U S A. Jan. 1, 1992;89(1):232-5. doi: 10.1073/pnas.89.1.232.

Suematsu et al., IgG1 plasmacytosis in interleukin 6 transgenic mice. Proc Natl Acad Sci U S A. Oct. 1989;86(19):7547-51. doi: 10.1073/pnas.86.19.7547.

Taga et al., Interleukin-6 triggers the association of its receptor with a possible signal transducer, gp130. Cell. Aug. 11, 1989;58(3):573-81. doi: 10.1016/0092-8674(89)90438-8.

Van Der Linden et al., Induction of immune responses and molecular cloning of the heavy chain antibody repertoire of Lama glama. J Immunol Methods. Jun. 23, 2000;240(1-2):185-95. doi: 10.1016/s0022-1759(00)00188-5.

Woo et al., Open label phase II trial of single, ascending doses of MRA in Caucasian children with severe systemic juvenile idiopathic arthritis: proof of principle of the efficacy of IL-6 receptor blockade in this type of arthritis and demonstration of prolonged clinical improvement. Arthritis Res Ther. 2005;7(6):R1281-8. doi: 10.1186/ar1826. Epub Sep. 15, 2005.

Yamasaki et al., Cloning and expression of the human interleukin-6 (BSF-2/IFN beta 2) receptor. Science. Aug. 12, 1988;241(4867):825-8. doi: 10.1126/science.3136546.

Zaki et al., CNTO 328, a monoclonal antibody to IL-6, inhibits human tumor-induced cachexia in nude mice. Int J Cancer. Sep. 10, 2004;111(4):592-5. doi: 10.1002/ijc.20270.

\* cited by examiner

POLYPEPTIDES COMPRISING IMMUNOGLOBULIN SINGLE VARIABLE DOMAINS TARGETING IL-6 AND TNF-α

RELATED APPLICATION

This application claims the benefit under 35 U.S.C. § 119(e) of U.S. Provisional Application Ser. No. 63/167,925, filed Mar. 30, 2021, the entire contents of which is incorporated herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 14, 2021, is named A084870222US01-SEQ-JRV.txt, and is 69,484 bytes in size.

1 FIELD

The present disclosure relates to polypeptides targeting interleukin-6 (IL-6) and TNF-α. It also relates to nucleic acid molecules encoding the polypeptide and vectors comprising the nucleic acids, and to compositions comprising the polypeptide, nucleic acid or vector. The disclosure further relates to these products for use in a method of treating a subject suffering from an inflammatory and/or autoimmune disease. Moreover, the disclosure relates to a method of producing these products.

2 TECHNOLOGICAL BACKGROUND

Rheumatoid arthritis is a severe autoimmune disease which affects around 25 million of patients worldwide (GBD 2015, Lancet. 2016 Oct. 8; 388(10053):1545-1602). A major symptom of rheumatoid arthritis are painful and swollen joints. This is caused by joint inflammation which involves an inflammation of the synovial cavity of the joint. This inflamed synovial cavity in rheumatoid arthritis is characterized by infiltration of immune cells and stromal cell activation (Klareskog, Catrina et al., Lancet. 2009 Feb. 21; 373(9664):659-72; Smolen, Aletaha et al., Nat Rev Dis Primers. 2018 Feb. 8; 4:18001). A specialized cell type, Fibroblast-like synoviocytes (FLS), is considered the key player of this process (Bartok and Firestein, Immunol Rev. 2010 January; 233(1):233-55). FLS together with macrophage-like synovial cells form the intimal lining layer of the synovial membrane. In rheumatoid arthritis, FLS proliferation and accumulation of immune cells trigger the inflammation and lead to membrane thickness, known as synovial hyperplasia—one of the primary symptoms of rheumatoid arthritis. As key mediators of joint inflammation in rheumatoid arthritis, FLS represent an attractive target cell type for rheumatoid arthritis treatment.

IL-6 is a pleiotropic cytokine secreted by a large number of cell types, including T and B cells, monocytes, fibroblasts and synoviocytes.

The interaction of IL-6, a protein originally identified as a B cell differentiation factor (Hirano et al., 1985, Proc. Natl. Acad. Sci. USA, 82: 5490-4; EP 0257406), with IL-6R (Yamasaki et al., 1988, Science, 241: 825-8; EP 0325474) results in the formation of the IL-6/IL-6R complex. This complex binds to gp130 (Taga et al, 1989, Cell, 58: 573-81; EP 0411946), a receptor protein which transmits various physiological actions of IL-6. IL-6 is currently known to be involved in—amongst others—the regulation of the immune response, hematopoiesis, the acute phase response, bone metabolism, angiogenesis, and inflammation. Deregulation of IL-6 production is implicated in the pathology of several autoimmune and chronic inflammatory proliferative disease processes (Ishihara and Hirano, 2002, Biochim. Biophys. Acta, 1592: 281-96). Polypeptides specifically binding to IL-6 (Klein et al., 1991, Blood, 78: 1198-204; EP 0312996), IL-6R (EP 0409607) or gp130 (Saito et al., 1993, J. Immunol. Methods, 163: 217-223; EP 0572118) proved to exhibit an efficient inhibitory effect on IL-6 functioning.

The prior art describes antibodies and antibody fragments directed against human IL-6, against human IL-6R and against human gp130 protein for the prevention and treatment of IL-6 relates disorders. Examples are Tocilizumab (see Woo et al., 2005, Arthritis Res. Ther. 7: 1281-8; Nishimoto et al., 2005, Blood 106: 2627-32; Ito et al., 2004, Gastroenterology, 126: 989-96; Choy et al., 2002, Arthritis Rheum. 46: 3143-50), BE8 (see Bataille et al., 1995, Blood 86: 685-91; Emilie et al., 1994, Blood 84: 2472-9; Beck et al., 1994, N. Engl. J. Med. 330: 602-5; Wendling et al., 1993, J. Rheumatol. 20: 259-62) and CNTO-328 of Centocor (see Journal of Clinical Oncology, 2004, 22/14S: 2560; Journal of Clinical Oncology, 2004, 22/14S: 2608; Int. J. Cancer, 2004, 111:592-5). Another active principle known in the art for the prevention and treatment of IL-6 related disorders is an Fc fusion of soluble gp130 (see Becker et al. 2004, immunity, 21: 491-501; Doganci et al., 2005, J. Clin. Invest. 115: 313-25; Nowell et al, 2003, J. Immunol. 171: 3202-9; Atreya et al., 2000, Nat. Med. 6: 583-8). Amino acid sequences and Nanobodies directed against IL-6R and polypeptides comprising the same are described in WO 08/020079.

Tumor Necrosis Factor alpha (TNF-α; TNF-alpha) is a homotrimeric cytokine which is produced mainly by monocytes and macrophages, but also known to be secreted by CD4$^+$ and CD8$^+$ peripheral blood T lymphocytes. TNF-α can exist as a soluble form or as a transmembrane protein. The primary role of TNF-α is in the regulation of immune cells. TNF-α acts as an endogenous pyrogen and dysregulation of its production has been implicated in a variety of human diseases including inflammatory bowel disease and other inflammatory diseases, such as RA.

Treatments currently approved by the FDA for rheumatoid arthritis include anti-TNF-α biologicals (such as Simponi® [golimumab], Enbrel® [etanercept], Remicade® [infliximab] and Humira® [adalimumab]). However, these anti-TNF-α treatments only show a full disease remission in a minority of patients and a substantial portion of non-responders is still remaining. Thus, so far no biological has exhibited sufficient efficacy with respect to disease remission in a significant percentage of patients suffering from rheumatoid arthritis and lack of, or loss of, response is still an issue.

Targeting multiple disease factors may be achieved for example by co-administration or combinatorial use of two separate biologicals, e.g. antibodies binding to different therapeutic targets. However, co-administration or combinatorial use of separate biologicals can be challenging, both from a practical and a commercial point of view. For example, two injections of separate products result in a more inconvenient and more painful treatment regime to the patients which may negatively affect compliance. With regard to a single injection of two separate products, it can be difficult or impossible to provide formulations that allow for acceptable viscosity at the required concentrations and suitable stability of both products. Additionally, co-administration and co-formulation requires production of two separate drugs which can increase overall costs.

Bispecific antibodies that are able to bind to two different antigens have been suggested as one strategy for addressing such limitations associated with co-administration or combinatorial use of separate biologicals, such as antibodies.

Bispecific antibody constructs have been proposed in multiple formats. For example, bispecific antibody formats may involve the chemical conjugation of two antibodies or fragments thereof (Brennan, M, et al., Science, 1985. 229 (4708): p. 81-83; Glennie, M. J., et al., J Immunol, 1987. 139(7): p. 2367-2375).

Disadvantages of such bispecific antibody formats include, however, high viscosity at high concentration, making e.g. subcutaneous administration challenging, and in that each binding unit requires the interaction of two variable domains for specific and high affinity binding, having implications on polypeptide stability and efficiency of production. Such bispecific antibody formats may also potentially lead to CMC (Chemistry Manufacturing and Control) issues related to mispairing of the light chains or mispairing of the heavy chains. No multispecific, such as bispecific, antibody constructs targeting TNF-α and IL-6 have made it to the clinic so far.

3 SUMMARY

Since rheumatoid arthritis patients are at present still inadequately responding to the available standard of care treatments, there remains an unmet medical need for improved agents for the treatment of RA.

The present inventors have developed novel and improved agents for treating inflammatory and/or autoimmune diseases, such as in particular rheumatoid arthritis (RA). These agents target two or multiple disease factors, including IL-6 and TNF-α, which factors mediate the biological mechanisms related to inflammatory diseases, and in particular RA.

The inventors have surprisingly found that dual targeting of IL-6 and TNF-α with a single agent has the potential to confer an efficacious treatment in rheumatoid arthritis patients, where a single monospecific agent therapy for the same indications may not be sufficiently efficacious.

The present inventors found that bi- or multi-specific polypeptides (e.g. immunoglobulin single variable domain (ISVD) constructs) targeting specifically IL-6 and TNF-α at the same time have an increased efficiency of modulating the symptoms of rheumatoid arthritis as compared to monospecific anti-TNF-α or mono-specific anti-IL-6 polypeptides. Such polypeptides (such as ISVD constructs) could be efficiently produced (e.g. In microbial hosts) and conveniently administered. Furthermore, such polypeptides (such as ISVD constructs) could be shown to have limited reactivity to pre-existing antibodies in the subject to be treated (i.e., antibodies present in the subject before the first treatment with the antibody construct). In some embodiments such polypeptides (such as ISVD constructs) exhibit a half-life in the subject to be treated that is long enough such that the number of consecutive treatments can be limited and thus can be sufficiently spaced apart in timing.

The polypeptides of the present disclosure (e.g. immunoglobulin single variable domain (ISVD) constructs) comprise or consist of at least three immunoglobulin single variable domains (ISVDs), wherein at least one ISVD specifically binds to TNF-α and at least two ISVDs specifically bind to IL-6. According to some embodiments, the at least one ISVD binding to TNF-α specifically binds to human TNF-α (hTNF-α) and the at least two ISVDs binding to IL-6 specifically bind to human IL-6 (hIL-6).

According to some preferred embodiments, the polypeptides of the present disclosure further comprise one or more other groups, residues, moieties or binding units, optionally linked via one or more peptidic linkers, in which said one or more other groups, residues, moieties or binding units provide the polypeptide with increased half-life, compared to the corresponding polypeptides without said one or more other groups, residues, moieties or binding units. For example, the binding unit can be an ISVD that binds to a serum protein, for instance to a human serum protein such as human serum albumin.

Also provided are nucleic acid molecules capable of expressing the polypeptides of the present disclosure, nucleic acids or vectors comprising the nucleic acids, and compositions comprising the polypeptides, the nucleic acids or the vectors. In some embodiments, the compositions are pharmaceutical compositions.

Also provided are (non-human) hosts or host cells comprising the nucleic acids or vectors that encode the polypeptides according to the disclosure.

Further provided is a method for producing the polypeptide according to the disclosure, said method at least comprising the steps of:
 a. expressing, in a suitable host cell or (non-human) host organism or in another suitable (e.g. cell-free) expression system, a nucleic acid; optionally followed by:
 b. isolating and/or purifying the polypeptides according to the disclosure.

Moreover, the present disclosure provides the polypeptides, the compositions comprising the polypeptides, or the compositions comprising the nucleic acids or vectors comprising the nucleotide sequences that encode the polypeptides, for use as a medicament. In some embodiments, the polypeptides or compositions are for use in the treatment of an inflammatory and/or autoimmune disease, such as RA.

In addition, provided is a method of treating an inflammatory disease, such as RA, wherein said method comprises administering, to a subject in need thereof, a pharmaceutically active amount of the polypeptide or a composition according to the disclosure. In some embodiments, the method further comprises administering one or more additional therapeutic agents.

Further provided is the use of the polypeptides or compositions of the present disclosure in the preparation of a medicament (such as a pharmaceutical composition) for treating an inflammatory and/or autoimmune disease, such as RA.

In particular, the present disclosure provides the following embodiments:

Embodiment 1. A polypeptide, a composition comprising the polypeptide, or a composition comprising a nucleic acid comprising a nucleotide sequence that encodes the polypeptide, for use as a medicament, wherein the polypeptide comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:
 a) a first ISVD comprises
  i. a CDR1 which has the amino acid sequence of SEQ ID NO: 6 or has 2 or 1
  ii. a CDR2 which has the amino acid sequence of SEQ ID NO: 10 or has 2 or 1 amino acid difference(s) with SEQ ID NO: 10; and iii. a CDR3 which has the amino acid sequence of SEQ ID NO: 14 or has 2 or 1 amino acid difference(s) with SEQ ID NO: 14;
b) a second ISVD comprises
iv. a CDR1 which has the amino acid sequence of SEQ ID NO: 8 or has 2 or 1
v. a CDR2 which has the amino acid sequence of SEQ ID NO: 12 or has 2 or 1 amino acid difference(s) with SEQ ID NO: 12; and
vi. a CDR3 which has the amino acid sequence of SEQ ID NO: 16 or has 2 or 1
c) a third ISVD comprises
vii. a CDR1 which has the amino acid sequence of SEQ ID NO: 9 or has 2 or 1
vii. a CDR2 which has the amino acid sequence of SEQ ID NO: 13 or has 2 or 1 amino acid difference(s) with SEQ ID NO: 13; and
ix. a CDR3 which has the amino acid sequence of SEQ ID NO: 17 or has 2 or 1,
wherein the first, second and third ISVD are optionally comprised in the order starting from the N-terminus.

Embodiment 2. The composition for use according to embodiment 1, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 3. The polypeptide or composition for use according to embodiment 1 or 2, wherein:
a) said first ISVD comprises a CDR1 having the amino acid sequence of SEQ ID NO:6, a CDR2 having the amino acid sequence of SEQ ID NO: 10 and a CDR3 having the amino acid sequence of SEQ ID NO: 14;
b) said second ISVD comprises a CDR1 having the amino acid sequence of SEQ ID NO: 8, a CDR2 having the amino acid sequence of SEQ ID NO: 12 and a CDR3 having the amino acid sequence of SEQ ID NO; 16; and
c) said third ISVD comprises a CDR1 having the amino acid sequence of SEQ ID NO: 9, a CDR2 having the amino acid sequence of SEQ ID NO: 13 and a CDR3 having the amino acid sequence of SEQ ID NO: 17.

Embodiment 4. The polypeptide or composition for use according to any of embodiments 1 to 3, wherein:
a) the amino acid sequence of said first ISVD has a sequence identity of more than 90% with SEQ ID NO: 2;
b) the amino acid sequence of said second ISVD has a sequence identity of more than 90% with SEQ ID NO: 4; and
c) the amino acid sequence of said third ISVD has a sequence identity of more than 90% identity with SEQ ID NO: 5.

Embodiment 5. The polypeptide or composition for use according to any of embodiments 1 to 4, wherein:
a) said first ISVD has the amino acid sequence of SEQ ID NO: 2;
b) said second ISVD has the amino acid sequence of SEQ ID NO: 4; and
c) said third ISVD has the amino acid sequence of SEQ ID NO: 5.

Embodiment 6. The polypeptide or composition for use according to any of embodiments 1 to 5, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 7. The polypeptide or composition for use according to embodiment 6, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 8. The polypeptide or composition for use according to any one of embodiments 6 to 7, in which said one or more other groups, residues, moieties or binding units that provide the polypeptide with increased half-life is chosen from the group consisting of binding units that can bind to serum albumin (such as human serum albumin) or a serum immunoglobulin (such as IgG).

Embodiment 9. The polypeptide or composition for use according to embodiment 8, in which said binding unit that provides the polypeptide with increased half-life is an ISVD that can bind to human serum albumin.

Embodiment 10. The polypeptide or composition for use according to embodiment 9, wherein the ISVD binding to human serum albumin comprises
i. a CDR1 which has the amino acid sequence of SEQ ID NO: 7 amino acid difference(s) with SEQ ID NO: 7;
ii. a CDR2 which has the amino acid sequence of SEQ ID NO: 11 or has 2 or 1 amino acid difference(s) with SEQ ID NO: 11; and
iii. a CDR3 which has the amino acid sequence of SEQ ID NO: 15 or has 2 or 1 amino acid difference(s) with SEQ ID NO: 15.

Embodiment 11. The polypeptide or composition for use according to any of embodiments 9 to 10, wherein the ISVD binding to human serum albumin comprises a CDR1 having the amino acid sequence of SEQ ID NO: 7, a CDR2 having the amino acid sequence of SEQ ID NO: 11 and a CDR3 having the amino acid sequence of SEQ ID NO: 15.

Embodiment 12. The polypeptide or composition for use according to any of embodiments 9 to 11, wherein the amino acid sequence of said ISVD binding to human serum albumin has a sequence identity of more than 90% with SEQ ID NO: 3.

Embodiment 13. The polypeptide or composition for use according to any of embodiments 9 to 12, wherein said ISVD binding to human serum albumin has the amino acid sequence of SEQ ID NO: 3.

Embodiment 14. The polypeptide or composition for use according to any of embodiments 1 to 13, wherein the polypeptide has an extension at its C-terminal end of 1-5 amino acid residues, preferably an extension of a single amino acid residue, wherein the amino acid residues are independently chosen from naturally occurring amino acids, preferably independently chosen from glycine or alanine, leucine, isoleucine and valine, more preferably alanine and glycine, most preferably alanine.

Embodiment 15. The polypeptide or composition for use according to any of embodiments 1 to 14, wherein the amino acid sequence of the polypeptide comprises or consists of an amino acid sequence that has a sequence identity of more than 90% with SEQ ID NO: 1.

Embodiment 16. The polypeptide or composition for use according to any of embodiments 1 to 15, wherein the polypeptide comprises or consists of the amino acid sequence of SEQ ID NO: 1.

Embodiment 17. The polypeptide or composition for use according to any of claims 1 to 16, for use in the treatment of an inflammatory and/or autoimmune disease, such as rheumatoid arthritis.

Embodiment 18. A polypeptide that comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:
- a) a first ISVD binds to IL-6 and comprises
  - i. a CDR1 which has the amino acid sequence of SEQ ID NO: 6 or has 2 or 1
  - ii. a CDR2 which has the amino acid sequence of SEQ ID NO: 10 or has 2 or 1 amino acid difference(s) with SEQ ID NO: 10; and
  - iii. a CDR3 which has the amino acid sequence of SEQ ID NO: 14 or has 2 or 1 amino acid difference(s) with SEQ ID NO: 14;
- b) a second ISVD binds to IL-6 and comprises
  - iv. a CDR1 which has the amino acid sequence of SEQ ID NO: 8 or has 2 or 1
  - v. a CDR2 which has the amino acid sequence of SEQ ID NO: 12 or has 2 or 1 amino acid difference(s) with SEQ ID NO: 12; and
  - vi. a CDR3 which has the amino acid sequence of SEQ ID NO: 16 or has 2 or 1
- c) a third ISVD binds to TNF-α and comprises
  - vii. a CDR1 which has the amino acid sequence of SEQ ID NO: 9 or has 2 or 1
  - viii. a CDR2 which has the amino acid sequence of SEQ ID NO: 13 or has 2 or 1 amino acid difference(s) with SEQ ID NO: 13; and
  - ix. a CDR3 which has the amino acid sequence of SEQ ID NO: 17 or has 2 or 1, wherein the ISVDs are optionally comprised in the order starting from the N-terminus.

Embodiment 19. The polypeptide according to embodiment 18, wherein:
- a) said first ISVD comprises a CDR1 having the amino acid sequence of SEQ ID NO:6, a CDR2 having the amino acid sequence of SEQ ID NO: 10 and a CDR3 having the amino acid sequence of SEQ ID NO: 14;
- b) said second ISVD comprises a CDR1 having the amino acid sequence of SEQ ID NO: 8, a CDR2 having the amino acid sequence of SEQ ID NO: 12 and a CDR3 having the amino acid sequence of SEQ ID NO: 16; and
- c) said third ISVD comprises a CDR1 having the amino acid sequence of SEQ ID NO:9, a CDR2 having the amino acid sequence of SEQ ID NO: 13 and a CDR3 having the amino acid sequence of SEQ ID NO: 17.

Embodiment 20. The polypeptide according to any of embodiments 18 or 19, wherein:
- a) the amino acid sequence of said first ISVD has a sequence identity of more than 90% with SEQ ID NO: 2;
- b) the amino acid sequence of said second ISVD has a sequence identity of more than 90% with SEQ ID NO: 4; and
- c) the amino acid sequence of said third ISVD has a sequence identity of more than 90% identity with SEQ ID NO: 5.

Embodiment 21. The polypeptide according to any of embodiments 18 to 20, wherein:
- a) said first ISVD has the amino acid sequence of SEQ ID NO: 2;
- b) said second ISVD has the amino acid sequence of SEQ ID NO: 4; and
- c) said third ISVD has the amino acid sequence of SEQ ID NO: 5.

Embodiment 22. The polypeptide according to any of embodiments 18 to 21, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 23. The polypeptide according to embodiment 22, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 24. The polypeptide according to any one of embodiments 22 to 23, in which said one or more other groups, residues, moieties or binding units that provide the polypeptide with increased half-life is chosen from the group consisting of binding units that can bind to serum albumin (such as human serum albumin) or a serum immunoglobulin (such as IgG).

Embodiment 25. The polypeptide according to embodiment 24, in which said binding unit that provides the polypeptide with increased half-life is an ISVD that can bind to human serum albumin.

Embodiment 26. The polypeptide according to embodiment 25, wherein the ISVD binding to human serum albumin comprises
  - i. a CDR1 which has the amino acid sequence of SEQ ID NO: 7 amino acid difference(s) with SEQ ID NO: 7;
  - ii. a CDR2 which has the amino acid sequence of SEQ ID NO: 11 or has 2 or 1 amino acid difference(s) with SEQ ID NO: 11; and
  - iii. a CDR3 which has the amino acid sequence of SEQ ID NO: 15 or has 2 or 1 amino acid difference(s) with SEQ ID NO: 15.

Embodiment 27. The polypeptide according to any of embodiments 25 to 26, wherein the ISVD binding to human serum albumin comprises a CDR1 having the amino acid sequence of SEQ ID NO: 7, a CDR2 having the amino acid sequence of SEQ ID NO: 11 and a CDR3 having the amino acid sequence of SEQ ID NO: 15.

Embodiment 28. The polypeptide according to any of embodiments 25 to 27, wherein the amino acid sequence of said ISVD binding to human serum albumin has a sequence identity of more than 90% with SEQ ID NO: 3.

Embodiment 29. The polypeptide according to any of embodiments 25 to 28, wherein said ISVD binding to human serum albumin has the amino acid sequence of SEQ ID NO: 3.

Embodiment 30. The polypeptide according to any of embodiments 18 to 29, wherein the polypeptide has an extension at its C-terminal end of 1-5 amino acid residues, preferably an extension of a single amino acid residue, wherein the amino acid residues are independently chosen from naturally occurring amino acids, preferably independently chosen from glycine or alanine, leucine, isoleucine and valine, more preferably alanine and glycine, most preferably alanine.

Embodiment 31. The polypeptide according to any of embodiments 18 to 30, wherein the amino acid sequence of the polypeptide comprises or consists of an amino acid sequence that has a sequence identity of more than 90% with SEQ ID NO: 1.

Embodiment 32. The polypeptide according to any of embodiments 18 to 31, wherein the polypeptide comprises or consists of the amino acid sequence of SEQ ID NO: 1.

Embodiment 33. A nucleic acid comprising a nucleotide sequence that encodes a polypeptide according to any of embodiments 18 to 32.

Embodiment 34. A host or host cell comprising a nucleic acid according to embodiment 33.

Embodiment 35. A method for producing a polypeptide according to any of embodiments 18-32, said method at least comprising the steps of:
 a) expressing, in a suitable host cell or host organism or in another suitable expression system, a nucleic acid according to embodiment 33; optionally followed by:
 b) isolating and/or purifying the polypeptide according to any of embodiments 18 to 32.

Embodiment 36. A composition comprising at least one polypeptide according to any of embodiments 18 to 32, or a nucleic acid according to embodiment 33.

Embodiment 37. The composition according to embodiment 36, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 38. A method of treating an inflammatory and/or autoimmune disease, such as rheumatoid arthritis, wherein said method comprises administering, to a subject in need thereof, a pharmaceutically active amount of a polypeptide according to any of claims 18 to 32 or a composition according to any of claims 36 to 37.

Embodiment 39. The method according to claim 37, wherein the inflammatory and/or autoimmune disease is rheumatoid arthritis.

Embodiment 40. Use of a polypeptide according to any of claims 18 to 32 or a composition according to any of claims 36 to 37, in the preparation of a pharmaceutical composition for treating an inflammatory and/or autoimmune disease, such as rheumatoid arthritis.

Embodiment 41. Use of the polypeptide or a composition according to claim 40, wherein the inflammatory and/or autoimmune disease is rheumatoid arthritis.

Embodiment 42. A polypeptide that comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:
 a) a first ISVD comprises
  i. a CDR1 which has the amino acid sequence of SEQ ID NO: 6 or has 2 or 1
  ii. a CDR2 which has the amino acid sequence of SEQ ID NO: 10 or has 2 or 1 amino acid difference(s) with SEQ ID NO: 10; and
  iii. a CDR3 which has the amino acid sequence of SEQ ID NO: 14 or has 2 or 1 amino acid difference(s) with SEQ ID NO: 14;
 b) a second ISVD comprises
  iv. a CDR1 which has the amino acid sequence of SEQ ID NO: 8 or has 2 or 1
  v. a CDR2 which has the amino acid sequence of SEQ ID NO: 12 or has 2 or 1 amino acid difference(s) with SEQ ID NO: 12; and
  vi. a CDR3 which has the amino acid sequence of SEQ ID NO: 16 or has 2 or 1
 c) a third ISVD comprises
  vii. a CDR1 which has the amino acid sequence of SEQ ID NO: 9 or has 2 or 1
  viii. a CDR2 which has the amino acid sequence of SEQ ID NO: 13 or has 2 or 1 amino acid difference(s) with SEQ ID NO: 13; and
  ix. a CDR3 which has the amino acid sequence of SEQ ID NO: 17 or has 2 or 1,
 wherein the ISVDs are optionally comprised in the order starting from the N-terminus.

Embodiment 43. A polypeptide, a composition comprising the polypeptide, or a composition comprising a nucleic acid comprising a nucleotide sequence that encodes the polypeptide, for use as a medicament, wherein the polypeptide comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:
 a) a first ISVD comprises
  i. a CDR1 which has the amino acid sequence of SEQ ID NO: 9 or has 2 or 1
  ii. a CDR2 which has the amino acid sequence of SEQ ID NO: 13 or has 2 or 1 amino acid difference(s) with SEQ ID NO: 13; and
  iii. a CDR3 which has the amino acid sequence of SEQ ID NO: 17 or has 2 or 1;
 b) a second ISVD comprises
  iv. a CDR1 which has the amino acid sequence of SEQ ID NO: 150 or has 2 or 1 amino acid difference(s) with SEQ ID NO: 150;
  v. a CDR2 which has the amino acid sequence of SEQ ID NO: 151 or has 2 or 1 amino acid difference(s) with SEQ ID NO: 151; and
  vi. a CDR3 which has the amino acid sequence of SEQ ID NO: 152 or has 2 or 1 amino acid difference(s) with SEQ ID NO: 152; and
 c) a third ISVD comprises
  vii. a CDR1 which has the amino acid sequence of SEQ ID NO: 153 or has 2 or 1 amino acid difference(s) with SEQ ID NO: 153;
  viii. a CDR2 which has the amino acid sequence of SEQ ID NO: 154 or has 2 or 1 amino acid difference(s) with SEQ ID NO: 154; and
  ix. a CDR3 which has the amino acid sequence of SEQ ID NO: 155 or has 2 or 1 amino acid difference(s) with SEQ ID NO: 155,
 wherein the first, second and third ISVD are optionally comprised in the order starting from the N-terminus.

Embodiment 44. The polypeptide or composition for use according to embodiment 43, wherein:
 a) said first ISVD comprises a CDR1 having the amino acid sequence of SEQ ID NO:9, a CDR2 having the amino acid sequence of SEQ ID NO:13 and a CDR3 having the amino acid sequence of SEQ ID NO: 17;
 b) said second ISVD comprises a CDR1 having the amino acid sequence of SEQ ID NO: 150, a CDR2 having the amino acid sequence of SEQ ID NO: 151 and a CDR3 having the amino acid sequence of SEQ ID NO: 152; and
 c) said third ISVD comprises a CDR1 having the amino acid sequence of SEQ ID NO: 153, a CDR2 having the amino acid sequence of SEQ ID NO: 154 and a CDR3 having the amino acid sequence of SEQ ID NO: 155.

Embodiment 45. The polypeptide or composition for use according to any of embodiments 43 or 44, wherein:
a) the amino acid sequence of said first ISVD has a sequence identity of more than 90% with SEQ ID NO: 5;
b) the amino acid sequence of said second ISVD has a sequence identity of more than 90% with SEQ ID NO: 148; and
c) the amino acid sequence of said third ISVD has a sequence identity of more than 90% identity with SEQ ID NO: 149.

Embodiment 46. The polypeptide or composition for use according to any of embodiments 43 to 45, wherein:
a) said first ISVD has the amino acid sequence of SEQ ID NO: 5;
b) said second ISVD has the amino acid sequence of SEQ ID NO: 148; and
c) said third ISVD has the amino acid sequence of SEQ ID NO: 149.

Embodiment 47. A polypeptide, a composition comprising the polypeptide, or a composition comprising a nucleic acid comprising a nucleotide sequence that encodes the polypeptide, for use as a medicament, wherein the polypeptide comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:
a) a first ISVD comprises
  i. a CDR1 which has the amino acid sequence of SEQ ID NO: 9 or has 2 or 1
  ii. a CDR2 which has the amino acid sequence of SEQ ID NO: 13 or has 2 or 1 amino acid difference(s) with SEQ ID NO: 13; and
  iii. a CDR3 which has the amino acid sequence of SEQ ID NO: 17 or has 2 or 1;
b) a second ISVD comprises
  i. a CDR1 which has the amino acid sequence of SEQ ID NO: 160 or has 2 or 1 amino acid difference(s) with SEQ ID NO: 160;
  ii. a CDR2 which has the amino acid sequence of SEQ ID NO: 161 or has 2 or 1 amino acid difference(s) with SEQ ID NO: 161; and
  iii. a CDR3 which has the amino acid sequence of SEQ ID NO: 162 or has 2 or 1 amino acid difference(s) with SEQ ID NO: 162; and
c) a third ISVD comprises
  i. a CDR1 which has the amino acid sequence of SEQ ID NO: 150 or has 2 or 1 amino acid difference(s) with SEQ ID NO: 150;
  ii. a CDR2 which has the amino acid sequence of SEQ ID NO: 151 or has 2 or 1 amino acid difference(s) with SEQ ID NO: 151; and
  iii. a CDR3 which has the amino acid sequence of SEQ ID NO: 152 or has 2 or 1 amino acid difference(s) with SEQ ID NO: 152,
wherein the first, second and third ISVD are optionally comprised in the order starting from the N-terminus.

Embodiment 48. The polypeptide or composition for use according to embodiment 47, wherein:
a) said first ISVD comprises a CDR1 having the amino acid sequence of SEQ ID NO:9, a CDR2 having the amino acid sequence of SEQ ID NO: 13 and a CDR3 having the amino acid sequence of SEQ ID NO: 17;
b) said second ISVD comprises a CDR1 having the amino acid sequence of SEQ ID NO: 160, a CDR2 having the amino acid sequence of SEQ ID NO: 161 and a CDR3 having the amino add sequence of SEQ ID NO: 162; and
c) said third ISVD comprises a CDR1 having the amino acid sequence of SEQ ID NO: 150, a CDR2 having the amino acid sequence of SEQ ID NO: 151 and a CDR3 having the amino acid sequence of SEQ ID NO; 152.

Embodiment 49. The polypeptide or composition for use according to any of embodiments 47 or 48, wherein:
a) the amino acid sequence of said first ISVD has a sequence identity of more than 90% with SEQ ID NO: 5;
b) the amino acid sequence of said second ISVD has a sequence identity of more than 90% with SEQ ID NO: 159; and
c) the amino acid sequence of said third ISVD has a sequence identity of more than 90% identity with SEQ ID NO: 148.

Embodiment 50. The polypeptide or composition for use according to any of embodiments 47 to 49, wherein:
a) said first ISVD has the amino acid sequence of SEQ ID NO: 5;
b) said second ISVD has the amino acid sequence of SEQ ID NO: 159; and
c) said third ISVD has the amino acid sequence of SEQ ID NO: 148.

Embodiment 51. The polypeptide or composition for use according to any of embodiments 43 to 50, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 52. The polypeptide or composition for use according to any one of embodiment 51, in which said one or more other groups, residues, moieties or binding units that provide the polypeptide with increased half-life is chosen from the group consisting of binding units that can bind to serum albumin (such as human serum albumin) or a serum immunoglobulin (such as IgG).

Embodiment 53. The polypeptide or composition for use according to embodiment 52, in which said binding unit that provides the polypeptide with increased half-life is an ISVD that can bind to human serum albumin.

Embodiment 54. The polypeptide or composition for use according to embodiment 53, wherein the ISVD binding to human serum albumin comprises
  i. a CDR1 which has the amino acid sequence of SEQ ID NO: 7 amino acid difference(s) with SEQ ID NO: 7;
  ii. a CDR2 which has the amino acid sequence of SEQ ID NO: 11 or has 2 or 1 amino acid difference(s) with SEQ ID NO: 11; and
  iii. a CDR3 which has the amino acid sequence of SEQ ID NO: 15 or has 2 or 1 amino acid difference(s) with SEQ ID NO: 15.

Embodiment 55. The polypeptide or composition for use according to any of embodiments 53 or 54, wherein the ISVD binding to human serum albumin comprises a CDR1 having the amino acid sequence of SEQ ID NO: 7, a CDR2 having the amino acid sequence of SEQ ID NO: 11 and a CDR3 having the amino acid sequence of SEQ ID NO: 15.

Embodiment 56. The polypeptide or composition for use according to any of embodiments 53 to 55, wherein the amino acid sequence of said ISVD binding to human serum albumin has a sequence identity of more than 90% with SEQ ID NO: 3.

Embodiment 57. The polypeptide or composition for use according to any of embodiments 53 to 56, wherein said ISVD binding to human serum albumin has the amino acid sequence of SEQ ID NO: 3.

Embodiment 58. The polypeptide or composition for use according to any of embodiments 43 to 57, wherein the polypeptide has an extension at its C-terminal end of 1-5 amino acid residues, preferably an extension of a single amino acid residue, wherein the amino acid residues are independently chosen from naturally occurring amino acids, preferably independently chosen from glycine or alanine, leucine, isoleucine and valine, more preferably alanine and glycine, most preferably alanine.

Embodiment 59. The polypeptide or composition for use according to any of embodiments 43 to 46, wherein the amino acid sequence of the polypeptide comprises or consists of an amino acid sequence that has a sequence identity of more than 90% with SEQ ID NO: 147.

Embodiment 60. The polypeptide or composition for use according to any of embodiments 43 to 46, wherein the polypeptide comprises or consists of the amino acid sequence of SEQ ID NO: 147.

Embodiment 61. The polypeptide or composition for use according to any of embodiments 47 to 50, wherein the amino acid sequence of the polypeptide comprises or consists of an amino acid sequence that has a sequence identity of more than 90% with SEQ ID NO: 158.

Embodiment 62. The polypeptide or composition for use according to any of embodiments 47 to 50, wherein the polypeptide comprises or consists of the amino acid sequence of SEQ ID NO: 158.

Embodiment 63. The polypeptide or composition for use according to any of claims 43 to 62, for use in the treatment of an inflammatory and/or autoimmune disease, such as rheumatoid arthritis.

Embodiment 64. A nucleic acid comprising a nucleotide sequence that encodes a polypeptide according to any of embodiments 43 to 63.

Embodiment 65. A host or host cell comprising a nucleic acid according to embodiment 64.

Embodiment 66. A method for producing a polypeptide according to any of embodiments 43 to 63, said method at least comprising the steps of:
  a) expressing, in a suitable host cell or host organism or in another suitable expression system, a nucleic acid according to embodiment 64; optionally followed by:
  b) isolating and/or purifying the polypeptide according to any of embodiments 43 to 63.

Embodiment 67. A composition comprising at least one polypeptide according to any of embodiments 43 to 63, or a nucleic acid according to embodiment 64.

Embodiment 68. The composition according to embodiment 67, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 69. A method of treating an inflammatory and/or autoimmune disease, such as rheumatoid arthritis, wherein said method comprises administering, to a subject in need thereof, a pharmaceutically active amount of a polypeptide according to any of embodiments 43 to 63 or a composition according to any of embodiments 67 or 68.

Embodiment 70. The method according to embodiment 69, wherein the inflammatory and/or autoimmune disease is rheumatoid arthritis.

Embodiment 71. Use of a polypeptide according to any of embodiments 43 to 63 or a composition according to any of embodiments 67 or 68, in the preparation of a pharmaceutical composition for treating an inflammatory and/or autoimmune disease, such as rheumatoid arthritis.

Embodiment 72. Use of the polypeptide or a composition according to claim 71, wherein the inflammatory and/or autoimmune disease is rheumatoid arthritis.

4 BRIEF DESCRIPTION OF THE DRAWINGS

FIG. 1: Sensorgram showing simultaneous binding of recombinant soluble hTNF-$\alpha$ and hIL-6 to F027201062 captured via HSA.

Figure 2:
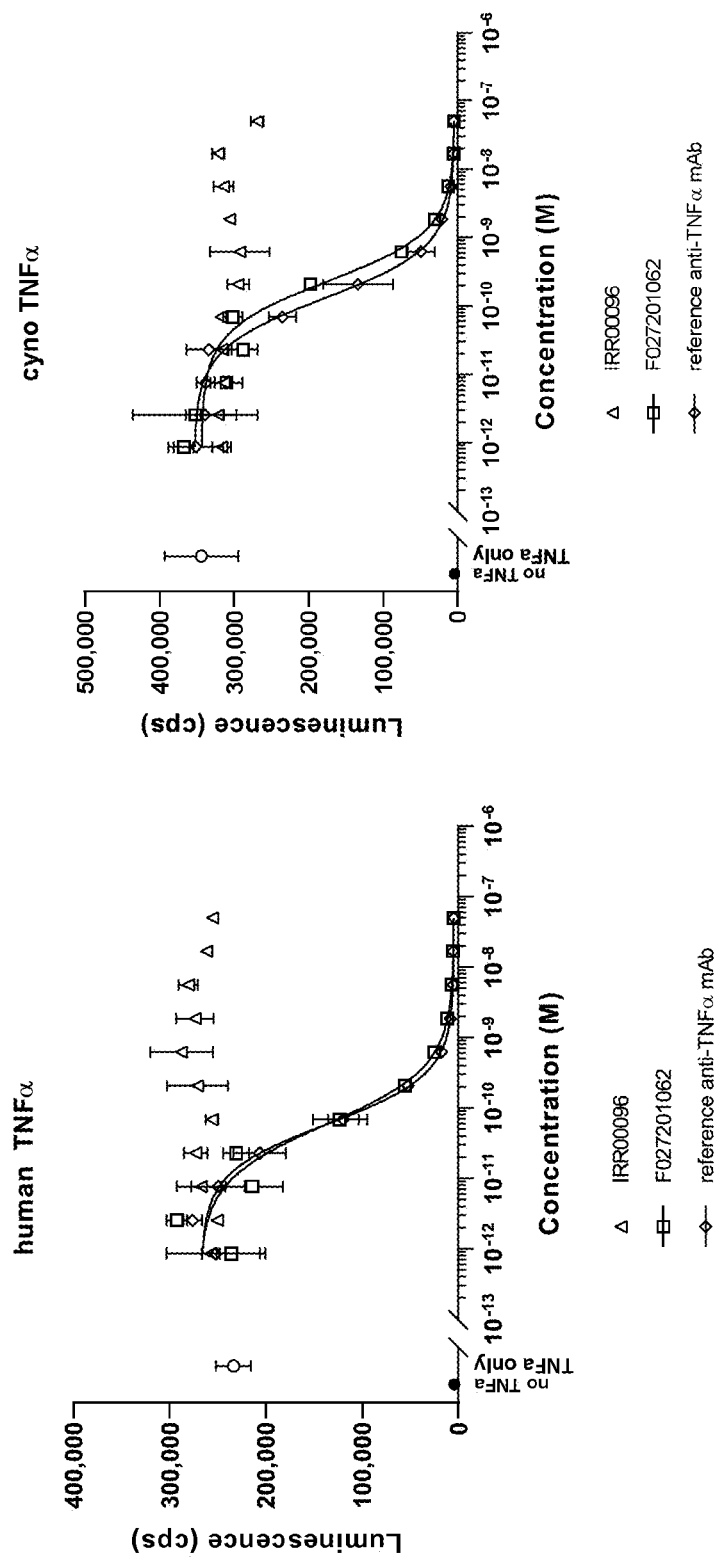

FIG. 2: Representative graph (experiment n3 in Table 11), showing inhibition of soluble human and cyno TNF-$\alpha$ in the Glo Response™ HEK293_NFκB-NLucP reporter assay by ISVD F027201062 and the reference anti-TNF-$\alpha$ mAb, IRR00096 is a negative control ISVD.

Figure 3:
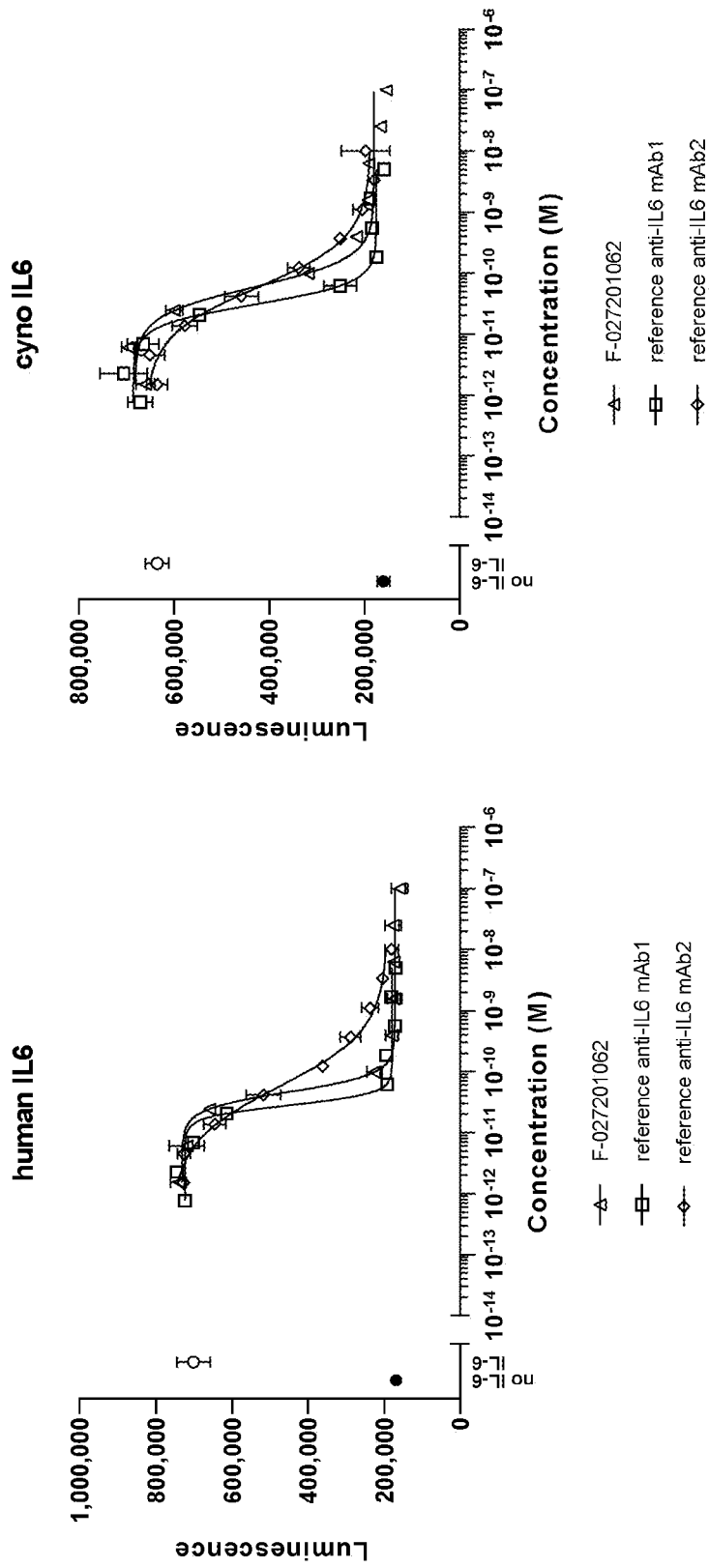

FIG. 3: Representative graph (experiment n3 in Table 12), showing inhibition of soluble human and cyno IL-6 in the IL-6 induced TF-1 proliferation assay by ISVD F027201062 and the reference anti-IL-6 mAb1 and mAb2, IRR00096 is a negative control ISVD. LCI=lower confidence interval, UCI=upper confidence interval.

Figure 4:
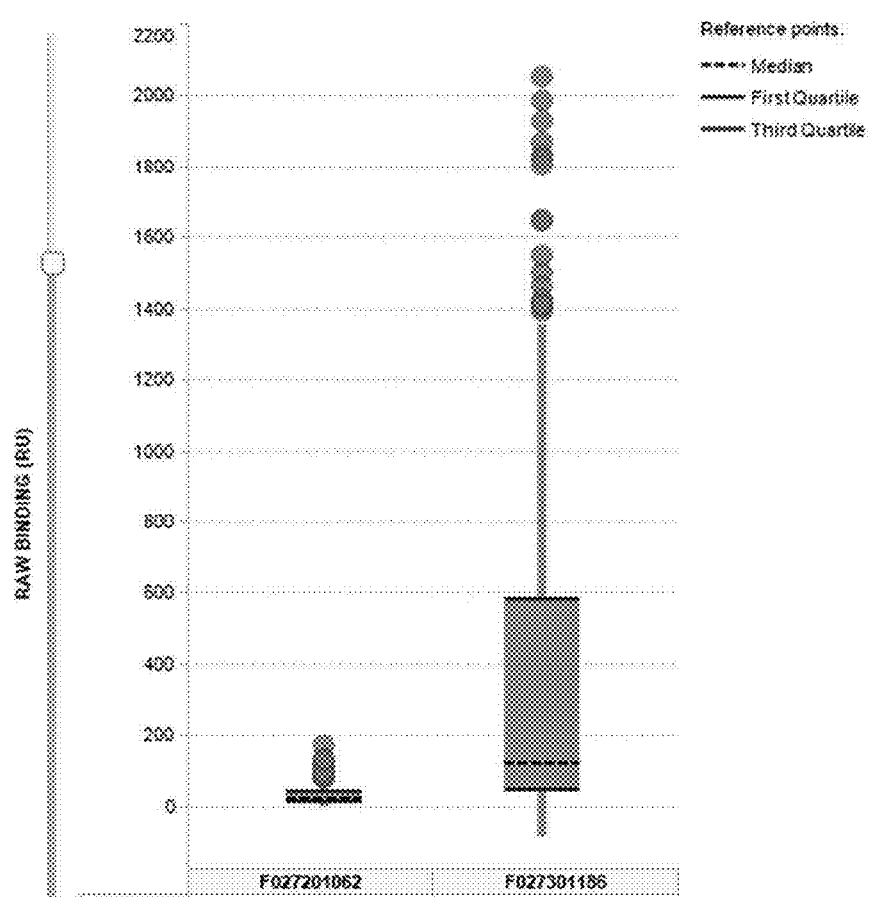

FIG. 4: Box plot showing the binding of pre-existing antibodies present in 96 human serum samples to the anti-IL-6/anti-TNF-$\alpha$ bispecific ISVD F027201062 and the control ISVD F027301186.

Figure 5:
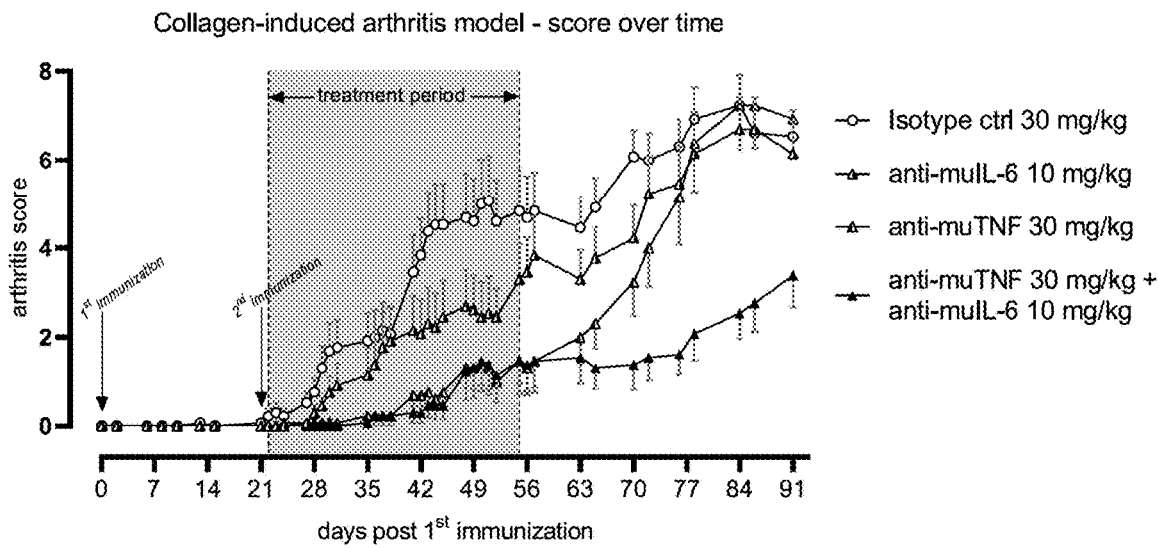

FIG. 5: Progressive arthritis in the collagen-induced arthritis model. N=13 male DBA/1 mice were immunized twice on day 0 and day 21 with 100 μg adjuvanted collagen 11. Starting day 22, mice were treated with the indicted compounds twice per week by intraperitoneal injection. Treatment was discontinued after day 56. Mice were scored for clinical signs and symptoms of joint inflammation. Shown are means±SEM. Statistical analysis is 2-way ANOVA with comparisons of treatments versus negative control for selected days throughout the disease course.

Figure 6:
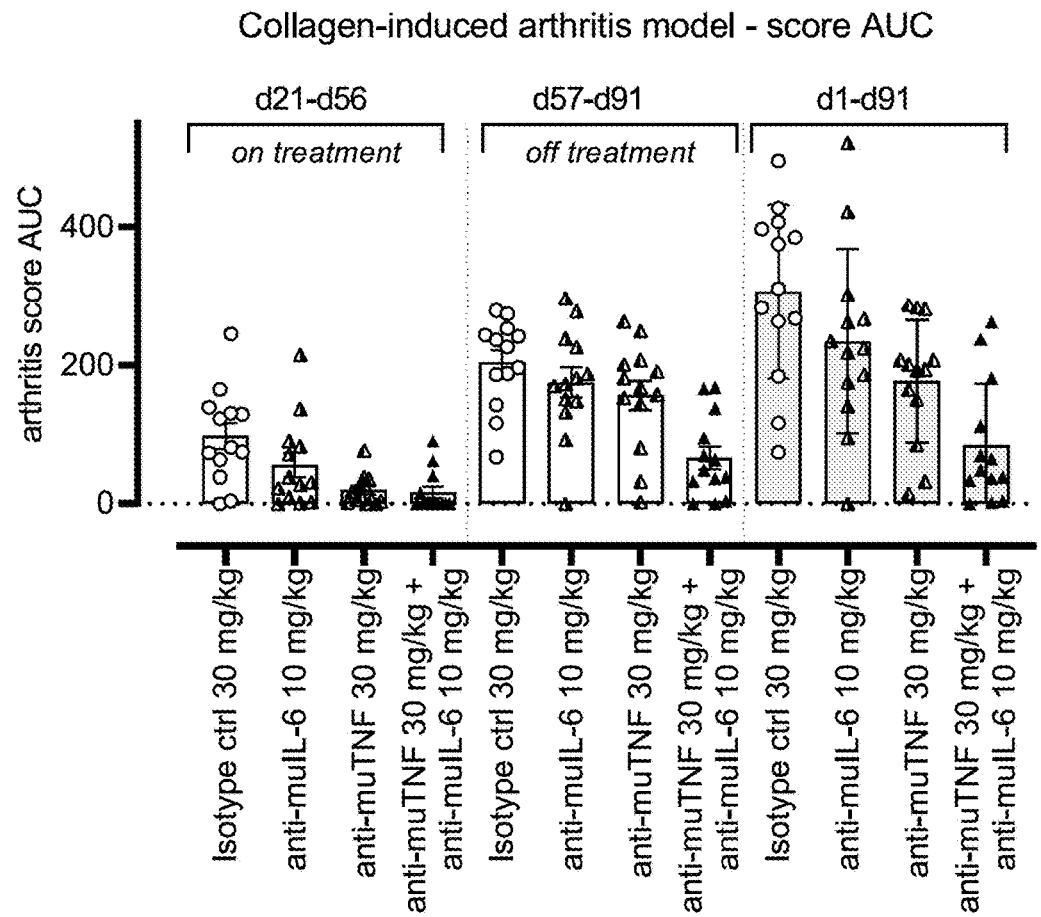

FIG. 6: Area under the arthritis score over time curve for the collagen-induced arthritis model. AUC was calculated separately for the treatment period day 21 through day 56, the off-treatment phase day 57 through day 91, and for the entire study duration. Shown are individual values and means±SEM, Statistical analysis is 1-way ANOVA with comparisons of treatments versus negative control.

Figure 7:
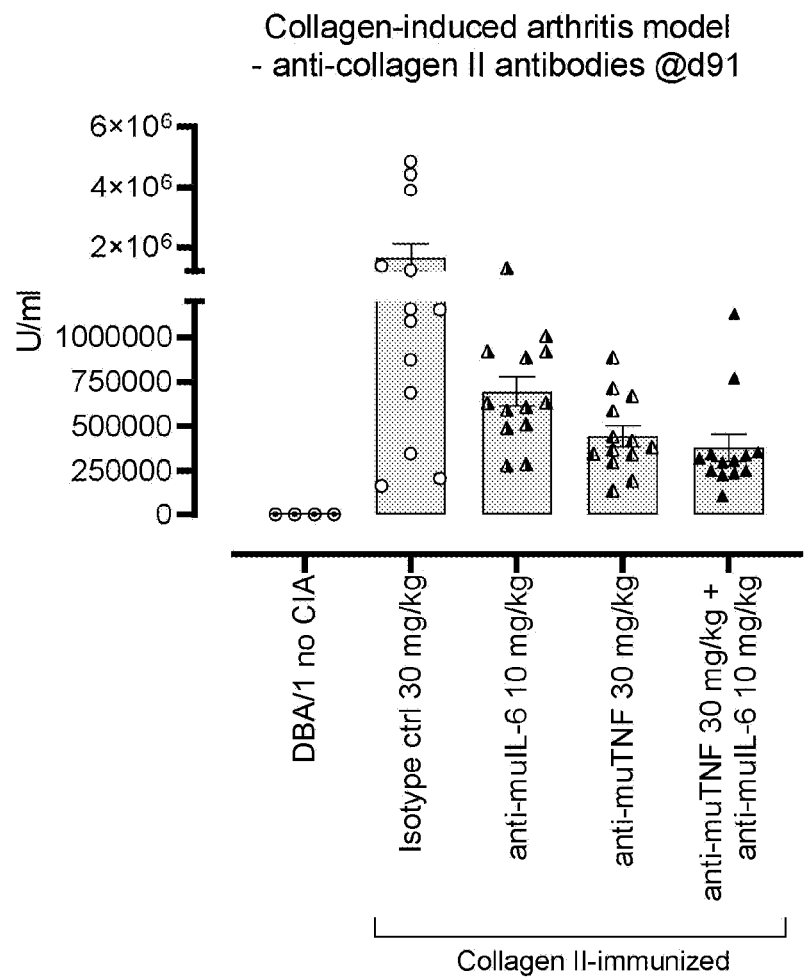

FIG. 7: Anti-collagen II antibodies in plasma at day 91 of the collagen-induced arthritis model. Collagen 11-specific titers were determined by ELISA in collagen II coated plates. Shown are individual values and means±SEM. Statistical analysis is 1-way ANOVA with comparisons of treatments versus negative control.

Figure 8:
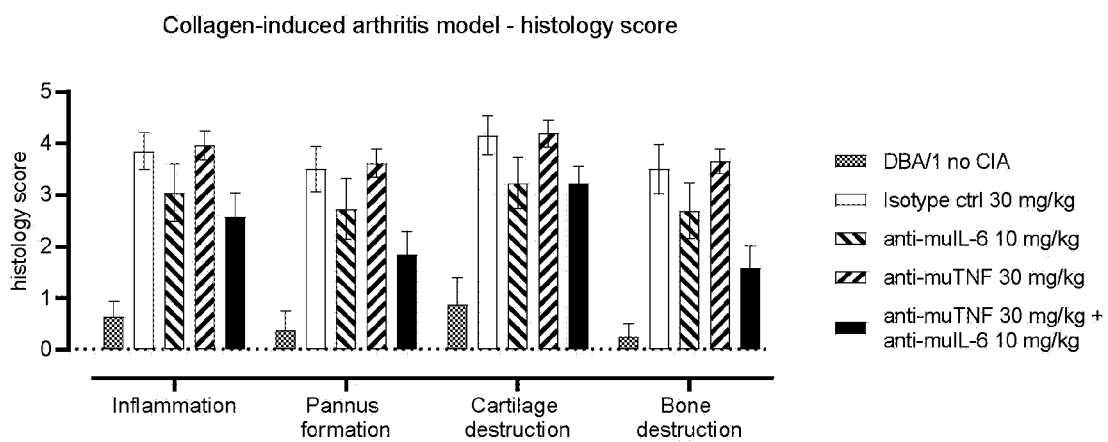

FIG. 8: Histology scores for hind paw metatarsal joints at day 91 of the collagen-induced arthritis model. Hind paws were processed for histology, and sections were stained with hematoxylin and eosin as well as safranin-O for cartilage proteoglycan visualization. Blinded assessment of score was performed by two individuals separately. Shown are means±SEM. Statistical analysis is 2-way ANOVA with comparisons of treatments versus negative control for all 4 dimensions of the histology assessment.

Figure 9:
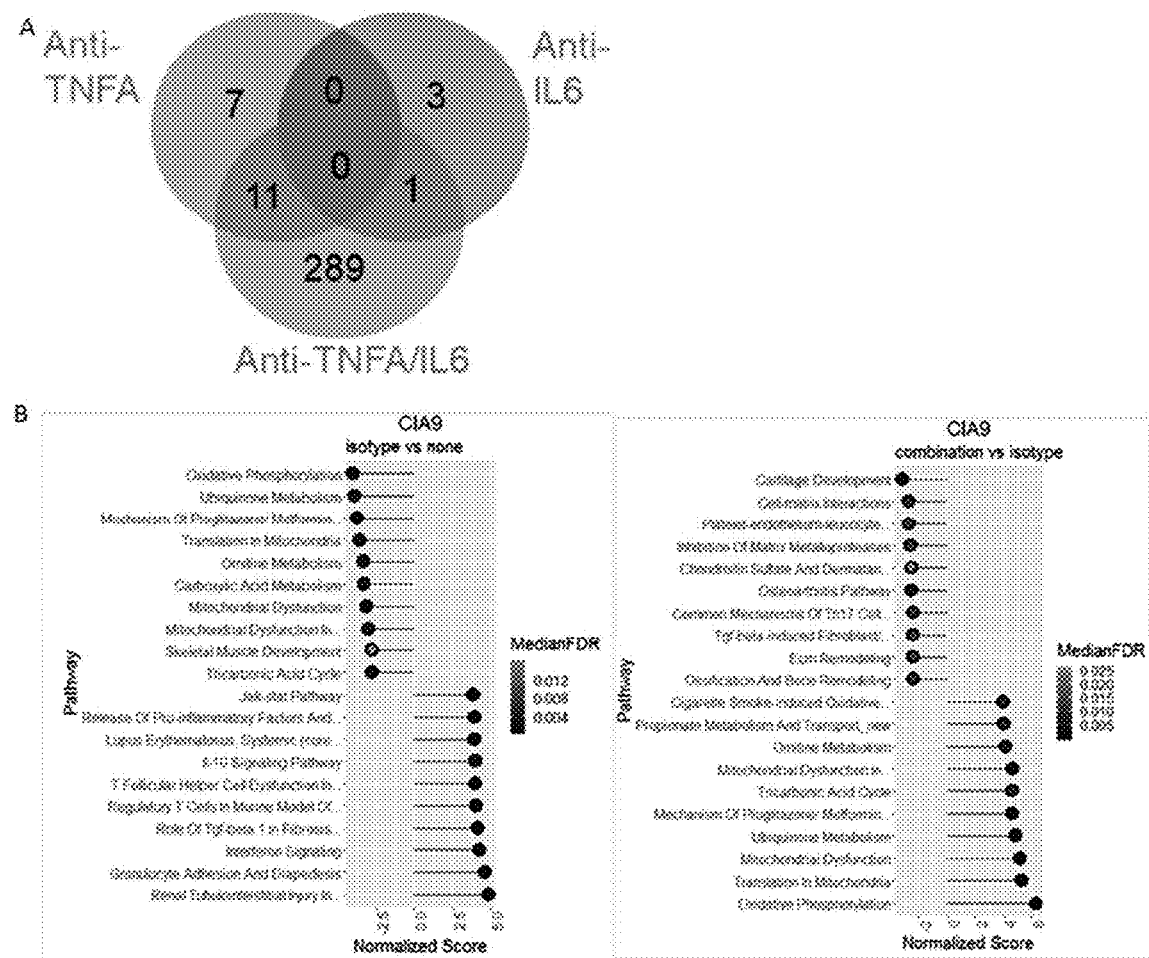

FIG. 9: RNAseq from Collagen-induced arthritis mouse paws treated with anti-IL-6, anti-TNF and combination of both. A) Venn diagram of significant deregulated transcripts (FC>1.2) on day 91 versus Isotype-treated control mice. B) Main up- and downregulated pathways in CIA (left) and after treatment with anti-TNF and anti-IL-6 combination (right).

Figure 10:
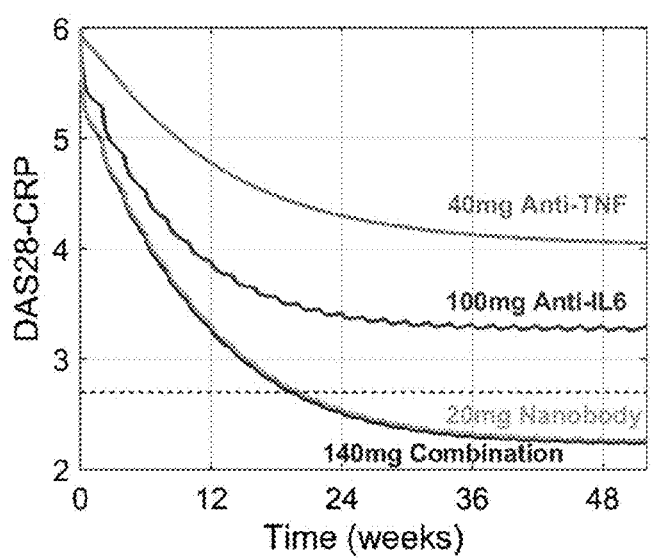

FIG. 10: Quantitative systems pharmacology model of Rheumatoid Arthritis (RA). Model simulates rheumatoid arthritis disease score DAS28-CRP after treatment with an anti-TNF-alpha comparator and anti-IL-6 comparator and shows an improved clinical efficacy (based on DAS28-CRP), even at lower doses of F027201062.

Figure 11:
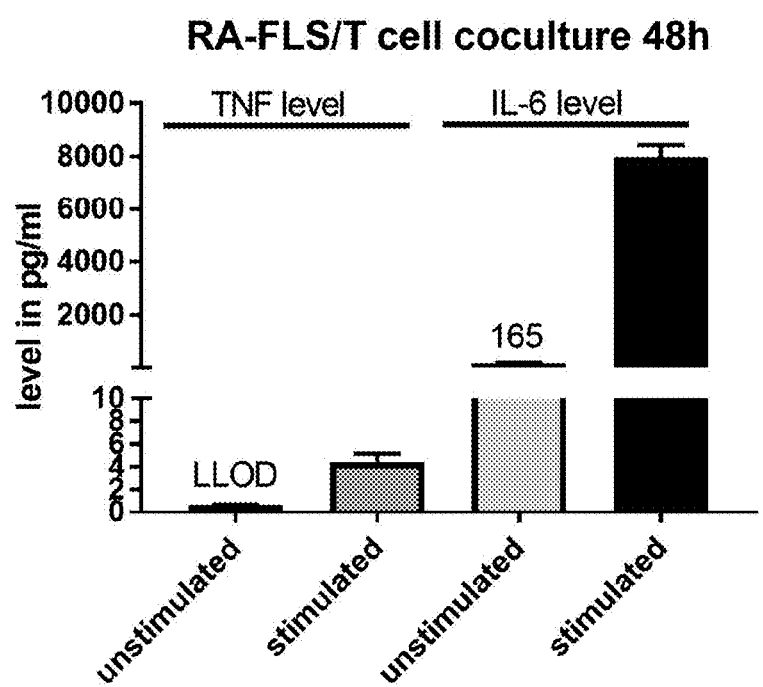

FIG. 11: Coculture of fibroblast-like synoviocytes (FLS) from Rheumatoid Arthritis (RA patients) with T cells from healthy donors. Coculture and stimulation with IL-17A, sIL-6R and anti-CD3 induces levels of TNF-α and IL-6 similar to published levels in human joints from RA patients.

Figure 12:
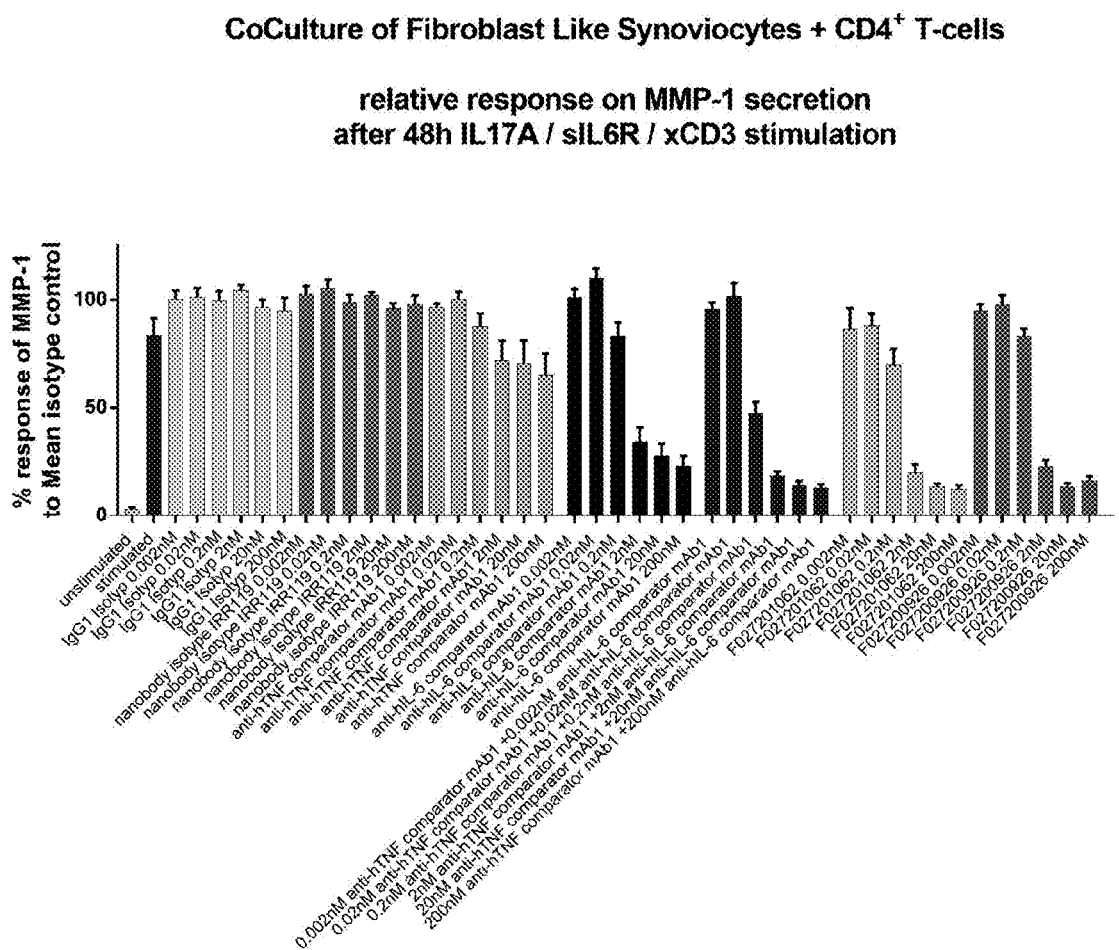

FIG. 12: Additive inhibition of MMP1 secretion in RA-FLS/T cell coculture with F027201062. IgG1 isotype control serves as negative control for comparator antibodies. ISVD isotype control is the negative control for multispecific ISVDs. Comparator antibodies and the combination of them are used as positive controls. Only donors responding to anti-TNF-α treatment are selected. Combination reflects full dose combination (e.g 200 nM anti-human TNF-α+200 nM anti-human IL-6). F027201062 and F027200926 are anti-TNF-α/IL-6 ISVD constructs. Shown are Mean±SEM, 8 different T cell donors. 3 technical replicates.

Figure 13:
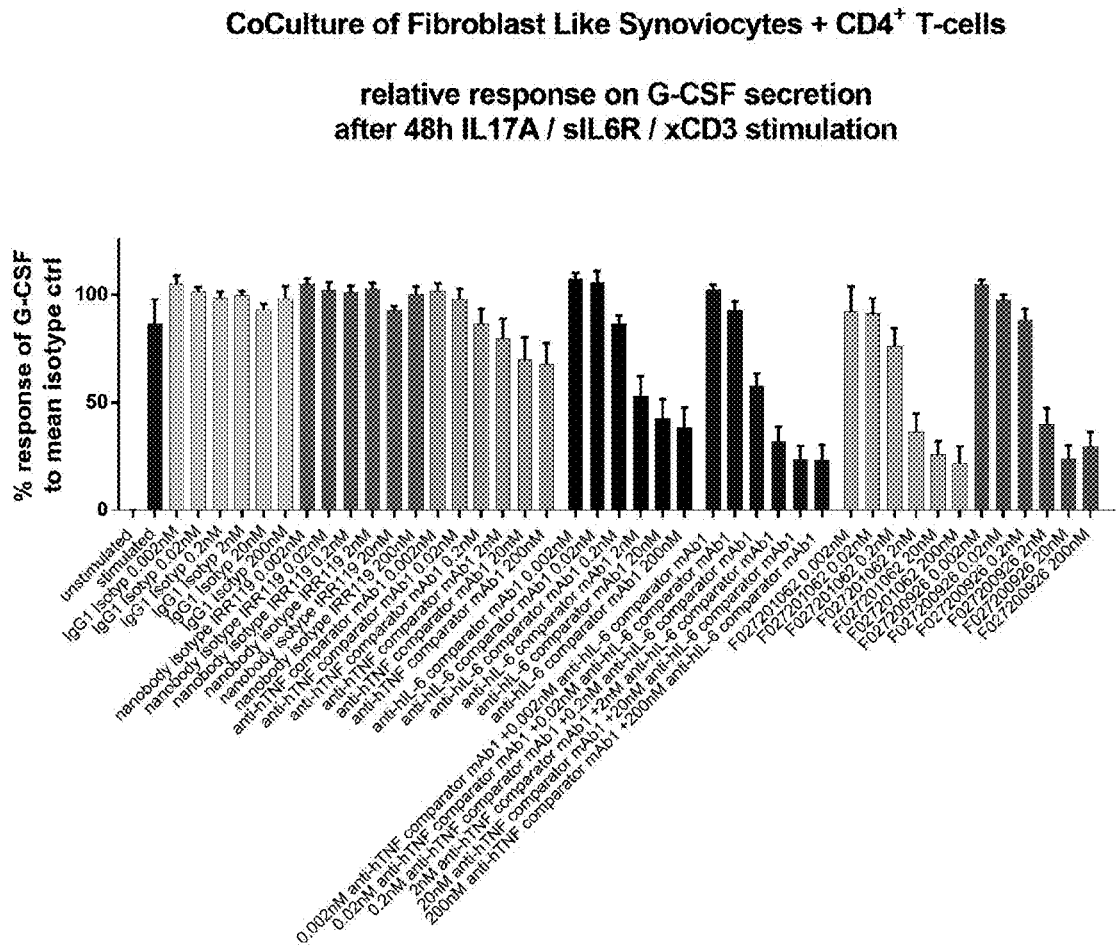

FIG. 13: Additive inhibition of G-CSF secretion in RA-FLS/T cell coculture with F027201062. IgG1 isotype control serves as negative control for comparator antibodies. ISVD isotype control is the negative control for multispecific ISVDs. Comparator antibodies and the combination of them are used as positive controls. Combination reflects full dose combination (e.g. 200 nM anti-human TNF-α+200 nM anti-human IL-6). F027201062 and F027200926 are anti-TNF-α/IL-6 ISVD constructs. Only donors responding to anti-TNF-α treatment are selected. Shown are Mean±SEM, 8 different T cell donors, 3 technical replicates.

Figure 14:
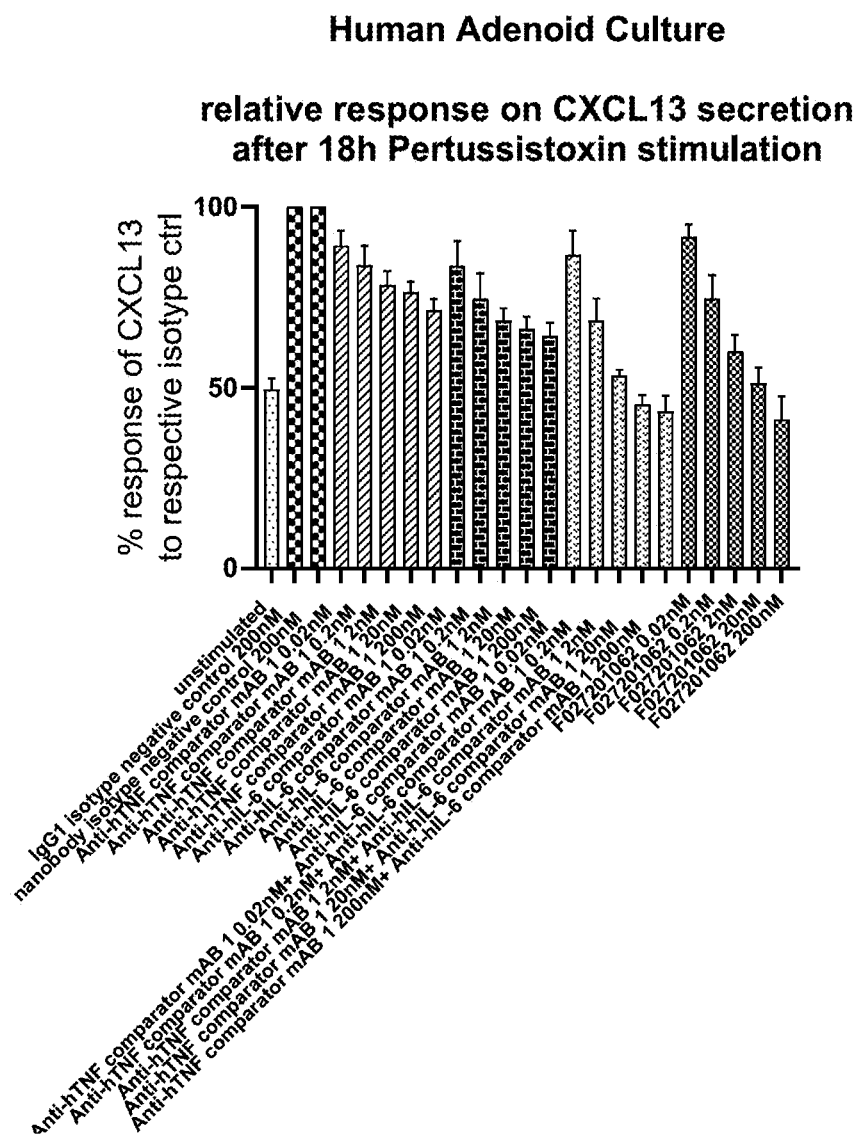

FIG. 14: Additive inhibition of CXCL13 in human adenoid culture with F027201062. IgG1 isotype control serves as negative control for comparator antibodies. ISVD isotype control is the negative control for F027201062 (anti-TNF-α/IL-6 ISVD constructs). Comparator antibodies and the combination of them are used as positive controls. Combination reflects full dose combination (e.g. 200 nM anti-human TNF-α+200 nM anti-human IL-6). Shown are Mean±SEM, 4-7 different donors, 2 technical replicates.

Figure 15:
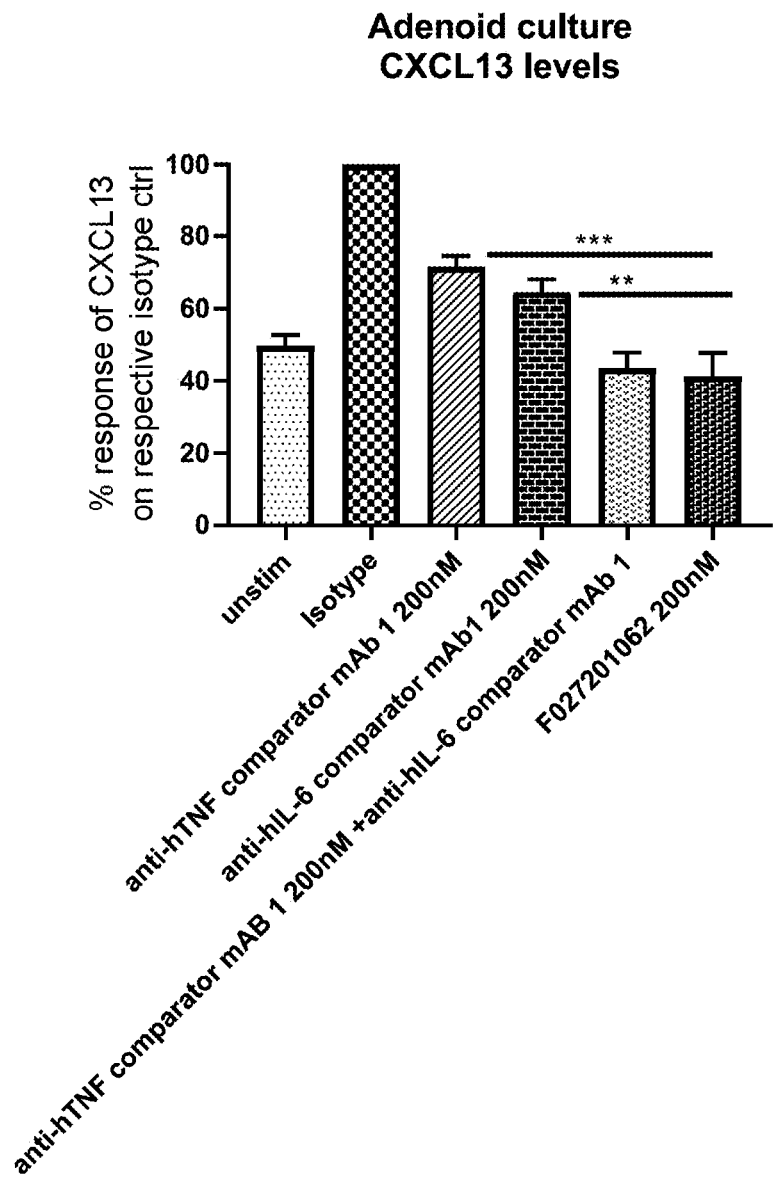

FIG. 15: Additive inhibition of CXCL13 in human adenoid culture with F027201062 at 200 nM. IgG1 isotype control serves as negative control for comparator antibodies. ISVD isotype control is the negative control for F027201062 (anti-TNF-α/IL-6 ISVD constructs). Comparator antibodies and the combination of them are used as positive controls. Combination reflects full dose combination (200 nM anti-human TNF-α+200 nM anti-human IL-6). Shown are Mean±SEM, 7 different donors, 2 technical replicates. Statistics are 1-way ANOVA and Tukey's multiple comparison test. p<0.01. p<0.001.

Figure 16:
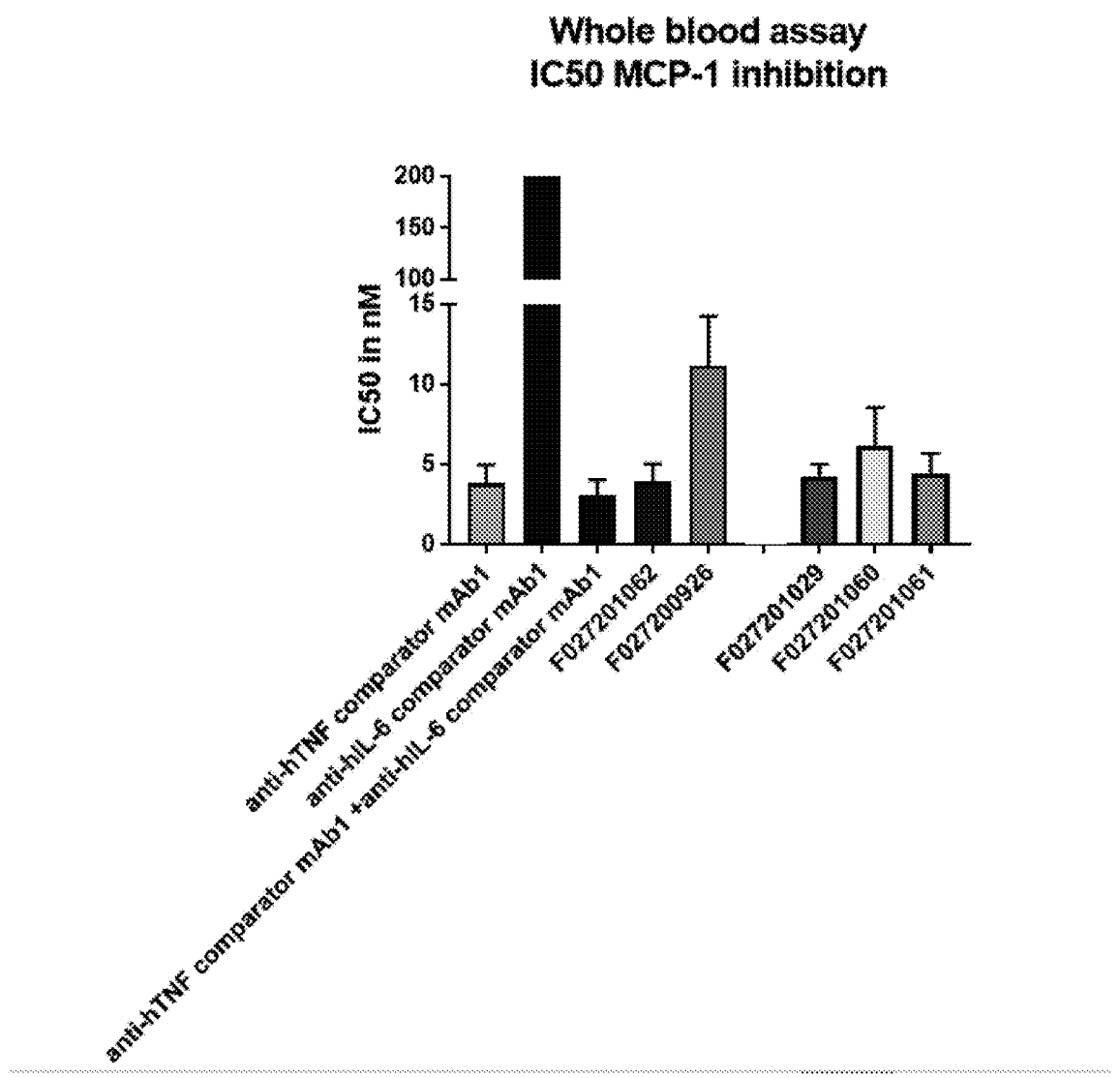

FIG. 16: TNF-α-dependent efficacy of anti-TNF-α/IL-6 ISVD constructs in human whole blood assay. IC50 of MCP-1 inhibition in SEB-stimulated whole blood is shown. IgG1 isotype control serves as negative control for comparator antibodies. ISVD isotype control is the negative control for anti-TNF-α/IL-6 ISVD constructs. Anti-hTNF-α comparator antibody is used as positive control. The following anti-TNF-α/LL-6 ISVD were evaluated: F027200926, F027201029, F027201060, F027201061, F027201062. Shown are Mean±SEM, 7 different donors.

Figure 17:
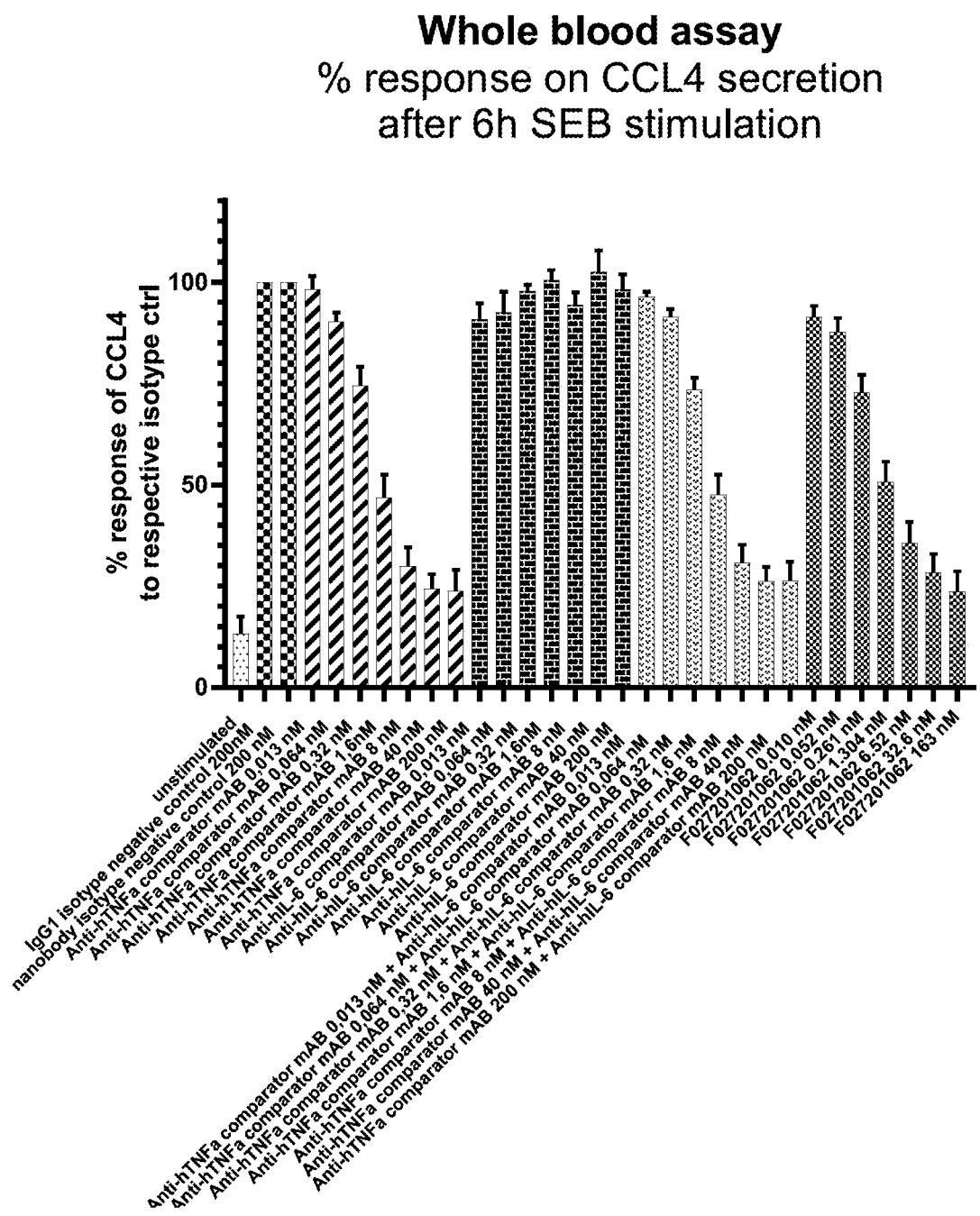

FIG. 17: TNF-α-dependent efficacy of anti-TNF/IL-6 ISVD constructs in human whole blood assay. Dose dependent inhibition of CCL4 in SEB-stimulated whole blood is shown. IgG1 isotype control serves as negative control for comparator antibodies. ISVD isotype control is the negative control for anti-TNF-α/IL-6 ISVD constructs. Anti-hTNF-α comparator antibody is used as positive control. F027201062 is a multispecific anti-TNF-α/IL-6 ISVD. Shown are Mean±SEM, 7 different donors.

Figure 18:
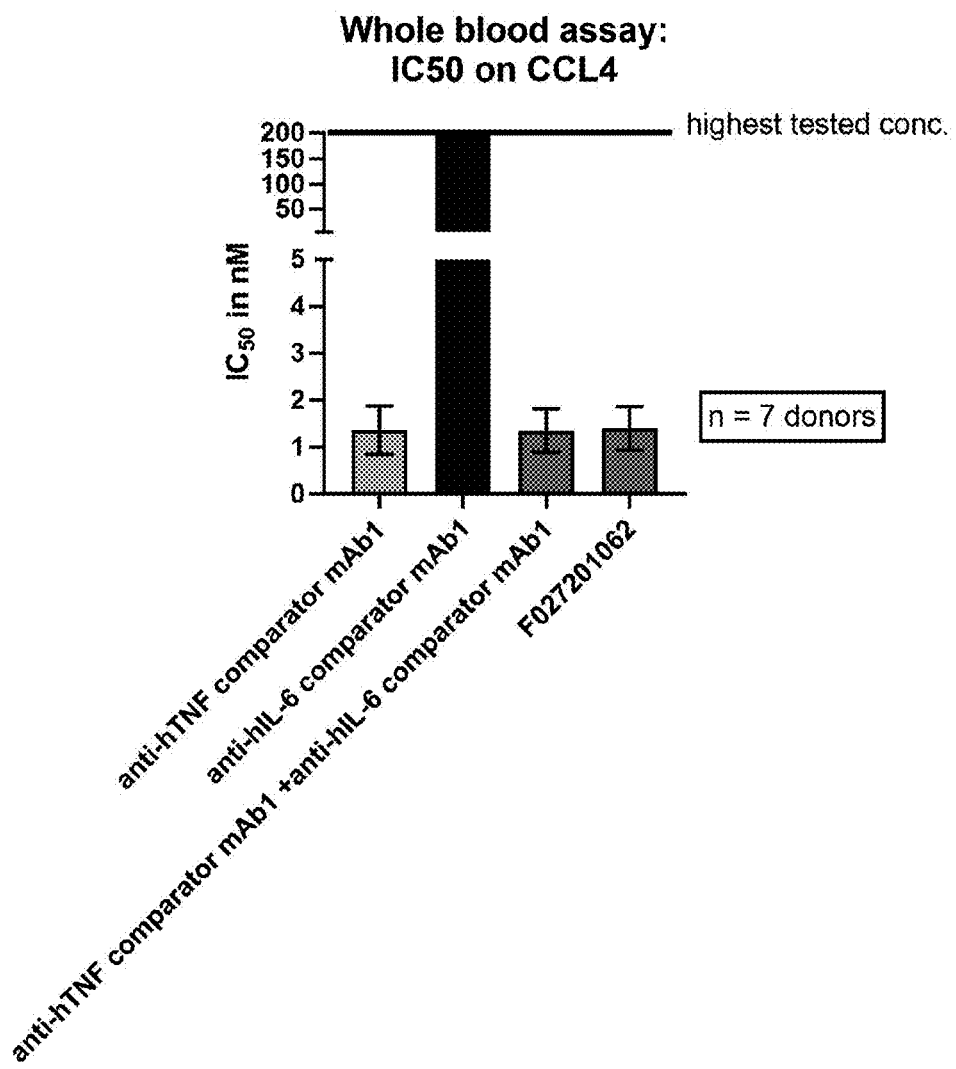

FIG. 18: TNF-dependent efficacy of anti-TNF-α/IL-6 ISVD constructs in human whole blood assay. IC50 of CCL4 inhibition in SEB-stimulated whole blood is shown. IgG1 isotype control serves as negative control for comparator antibodies. ISVD isotype control is the negative control for anti-TNF-α/IL-6 ISVD constructs. Anti-hTNF-α comparator antibody is used as positive control. F027201062 is a multispecific anti-TNF-α/IL-6 ISVD. Shown are Mean±SEM, 7 different donors.

Figure 19:
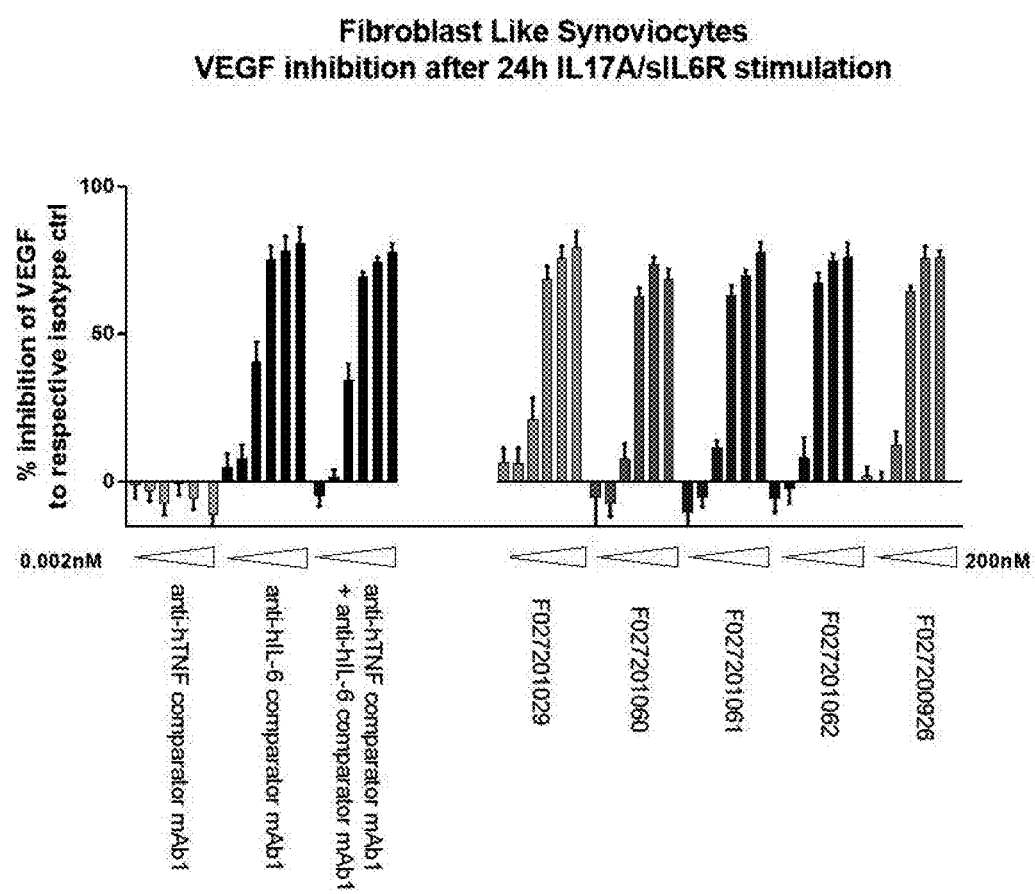

FIG. 19: IL-6 dependent efficacy of anti-TNF-α/IL-6 ISVD constructs in human RA-FLS (Fibroblast-like synoviocytes from rheumatoid arthritis patients). % inhibition of VEGF-A secretion normalized to isotype controls is shown. IgG1 isotype control serves as negative control for comparator antibodies. ISVD isotype control is the negative control for anti-TNF-α/IL-6 ISVD constructs. Dose-dependent inhibition with anti-hIL-6 comparator antibody (positive control) and the following anti-TNF-α/IL-6 ISVD: F027200926, F027201029, F027201060, F027201061, F027201062. Shown are Mean±SEM, 3 different rheumatoid arthritis donors, tested in two different passages.

Figure 20:
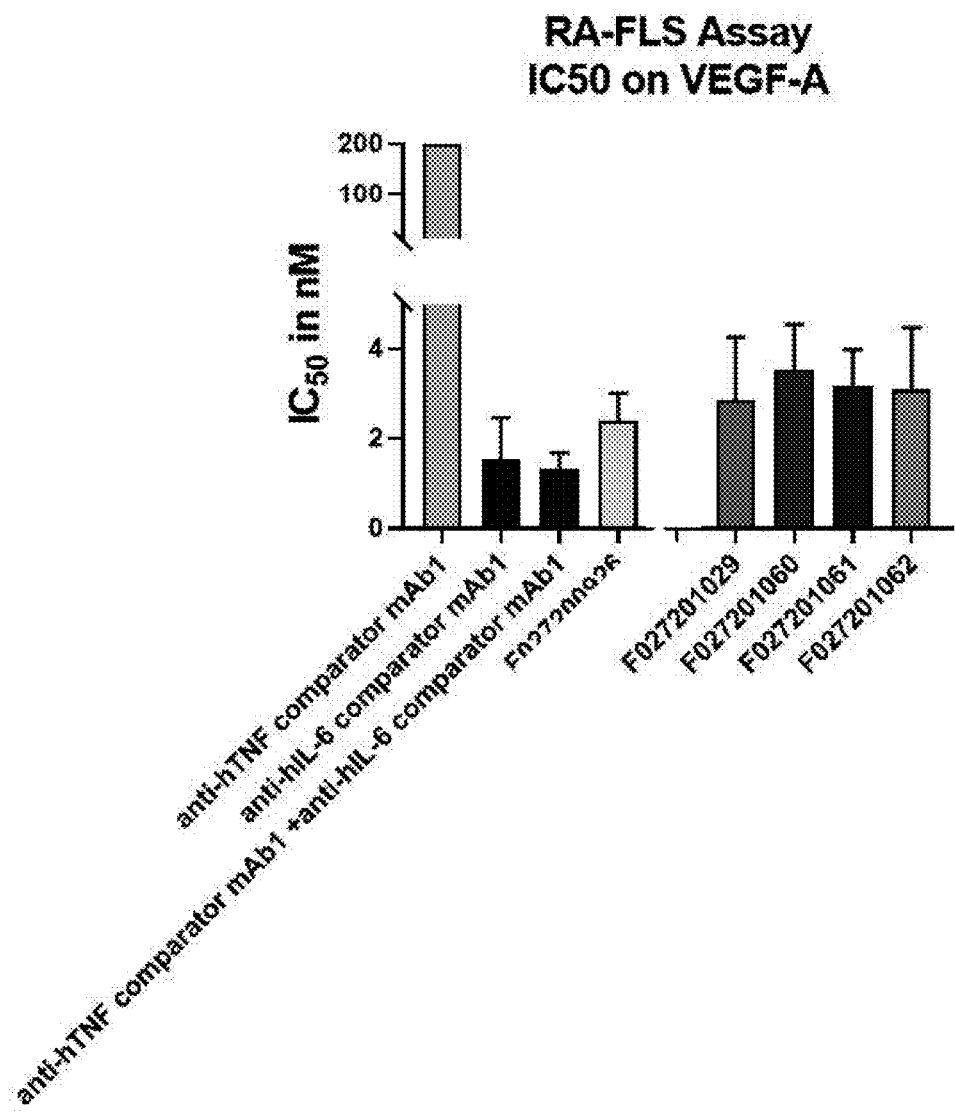

FIG. 20: IL-6 dependent efficacy of anti-TNF-α/IL-6 ISVD constructs in human RA-FLS (Fibroblast-like synoviocytes from rheumatoid arthritis patients). IgG1 isotype control serves as negative control for comparator antibodies. ISVD isotype control is the negative control for anti-TNF-α/IL-6 ISVD constructs. Anti-hIL-6 comparator antibody is used as positive control. IC50 of VEGF-A is shown for anti-hIL-6 comparator antibody (positive control) and the following anti-TNF-α/IL-6 ISVD: F027200926, F027201029, F027201060, F027201061, F027201062. Shown are Mean±SEM, 3 different rheumatoid arthritis donors, tested in two different passages.

Figure 21:
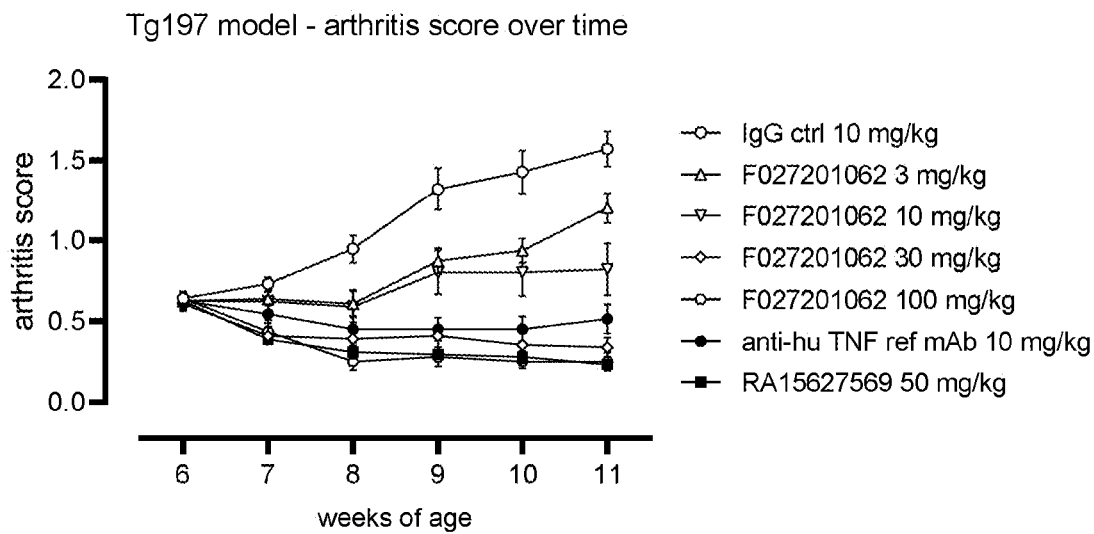

FIG. 21: Efficacy of F027201062 in Tg197 hTNF-α driven arthritis model. Arthritis score over time. Eight Tg197 mice (4 male and 4 female) were treated twice per week by intraperitoneal injection of the indicated compounds for 5 weeks. Arthritis score was monitored weekly. Shown are means±SEM. Statistical analysis is 2-way ANOVA with comparisons of treatments versus negative control for each week.

Figure 22:
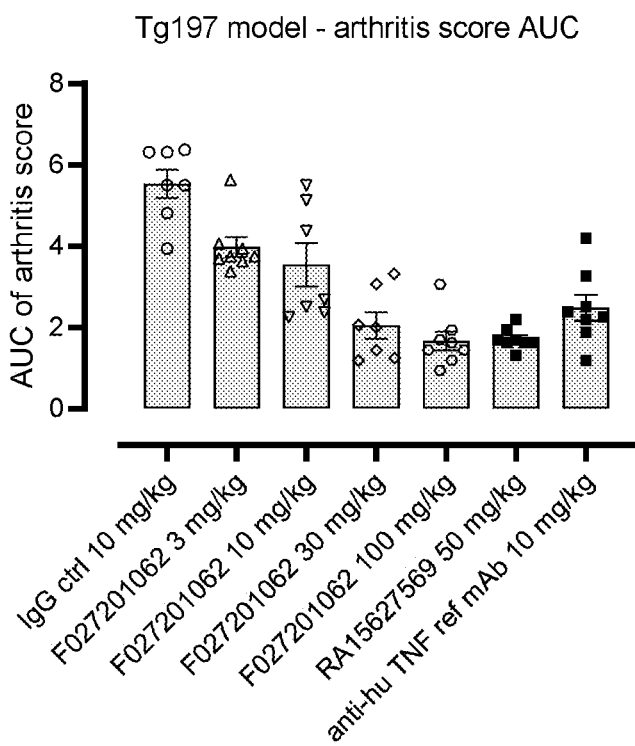

FIG. 22: Efficacy of F027201062 in Tg197 hTNF-α-driven arthritis model. Area under the arthritis score over time curve. Shown are individual values and means±SEM. Statistical analysis is 1-way ANOVA with comparisons of treatments versus negative control.

Figure 23:
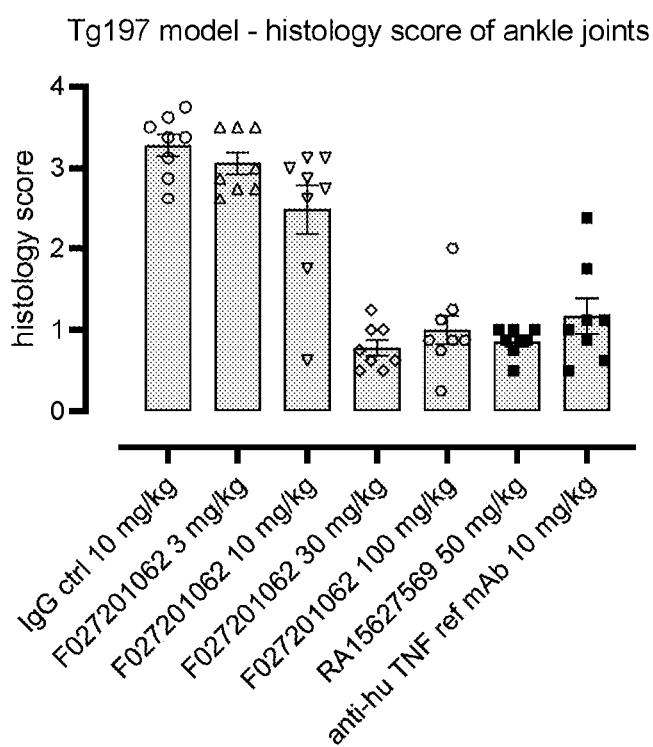

FIG. 23: Efficacy of F027201062 in Tg197 hTNF-α-driven arthritis model on histology score of ankle joints (n=2 per animal), Upon sacrifice at study completion, both hind paws were processed for histology and ankle joint sections were stained with hematoxylin and eosin. Section slides were read and scored in a blinded manner. Shown are individual values and means±SEM. Statistical analysis is 1-way ANOVA with comparisons of treatments versus negative control.

Figure 24:
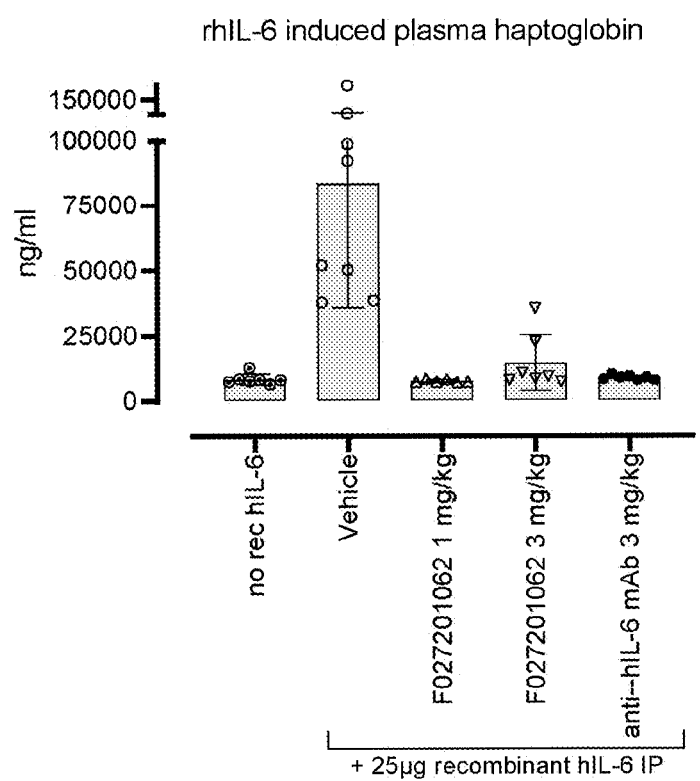

FIG. 24: IL-6-induced haptoglobin secretion. N=8 female BALB/C mice were injected with the indicated compounds. 8 hours later, mice were injected intraperitoneally with 25

µg/kg recombinant human IL-6 where indicated. 16 hours later mice were bled, and plasma was analyzed for haptoglobin using fluorometric bead assay. Shown are individual values and means±SEM. Statistical analysis is 1-way ANOVA with comparisons of treatments versus negative control.

Figure 25:
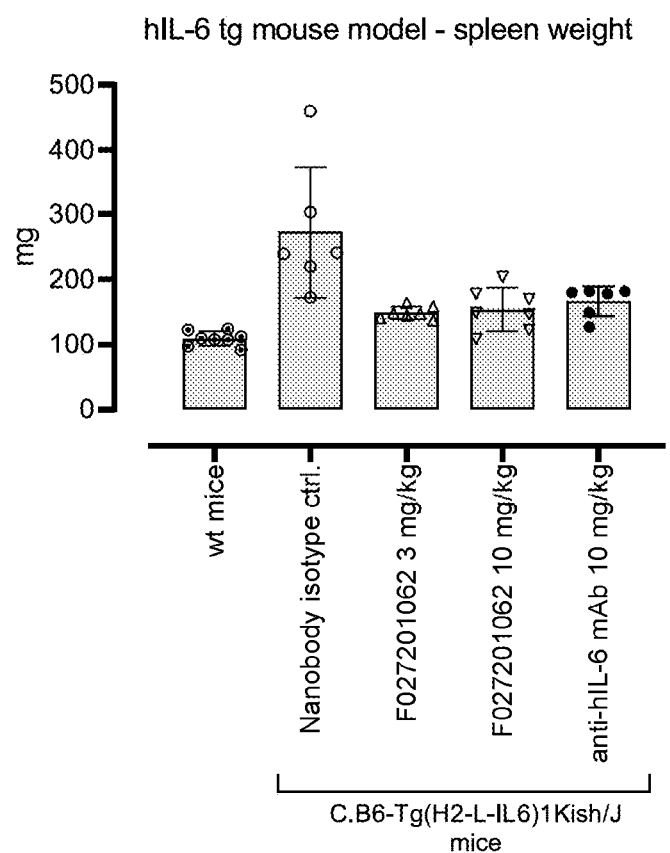

FIG. 25: Splenomegaly in hIL-6 transgenic mice. N=6-7 male and female hemizygous C.B6-Tg(H2-L-IL6)1$^{Kish/J}$ mice aged between 57 and 71 days were treated thrice per week with intraperitoneal injection with the indicated compounds for a duration of 2 weeks. Upon sacrifice, spleens were removed and weight was recorded. Wild type littermate animals served as control. Shown are individual values and means±SEM. Statistical analysis is 1-way ANOVA with comparisons of treatments versus negative control.

Figure 26:
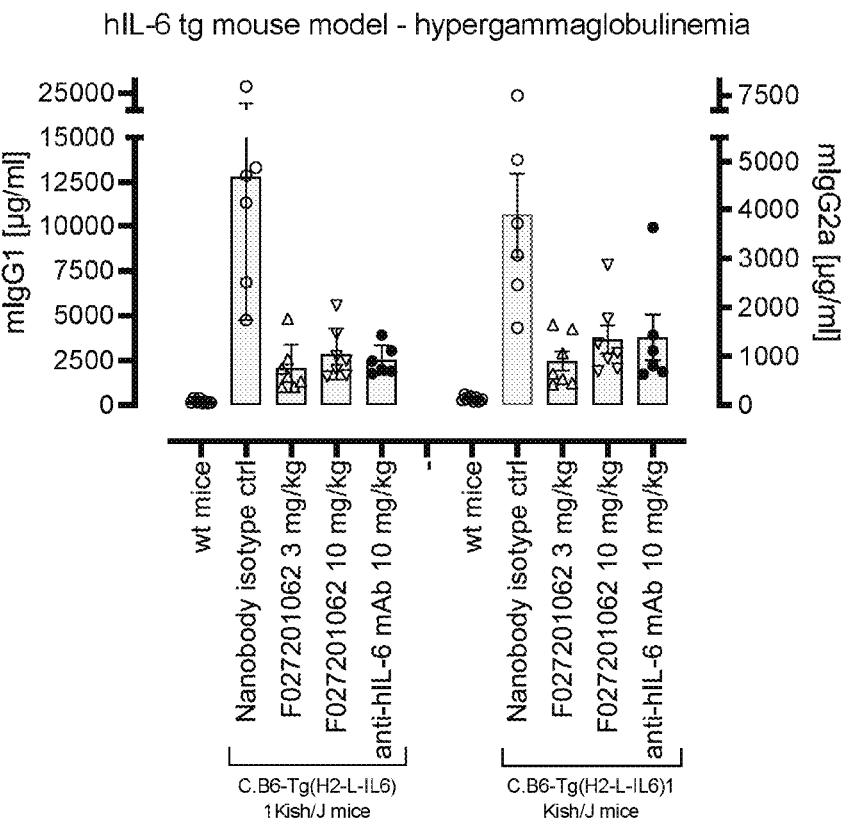

FIG. 26: Hypergammaglobulinemia in hIL-6 transgenic mice. N=6-7 male and female hemizygous C.B6-Tg(H2-L-IL6)1$^{Kish/J}$ mice aged between 57 and 71 days were treated thrice per week with intraperitoneal injection with the indicated compounds for a duration of 2 weeks. Upon sacrifice, mice were bled and both IgG1 and IgG2a isotype immunoglobulins were measured by chemiluminescence bead assay. Plasma from wt littermate animals served as control. Shown are individual values and means±SEM. Statistical analysis is 1-way ANOVA with comparisons of treatments versus negative control.

Figure 27:
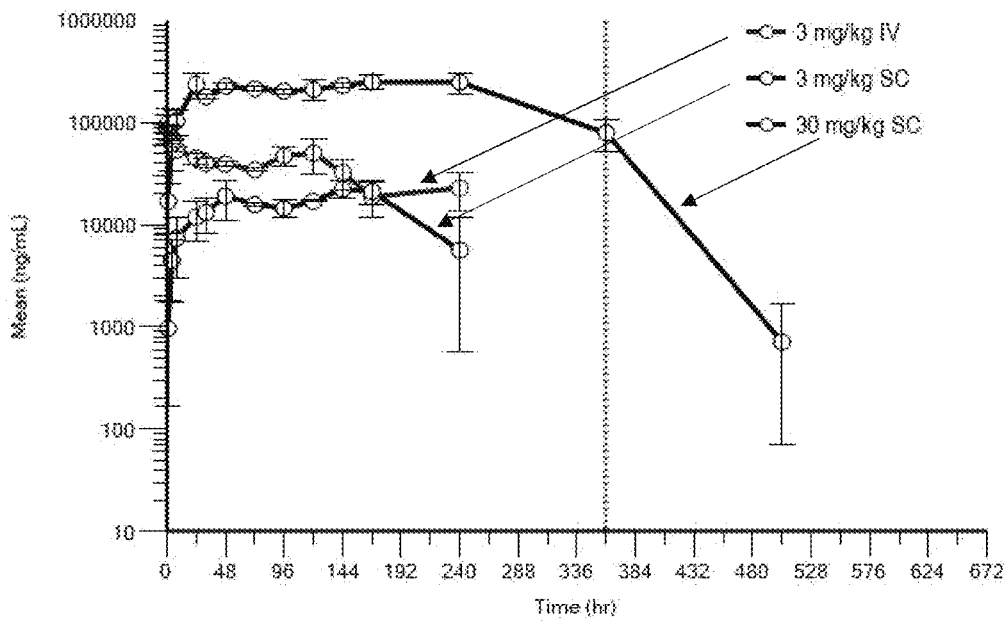

FIG. 27: Single dose pharmacokinetics of F027201062 in non-human primate. Serum concentration profiles of F027201062 after single dose administration in non-human primates at the indicated concentrations and administration routes (n=3 male, naïve cynomolgus monkeys (*Macaca fascicularis*) per group). The red, dashed line indicates the confirmed presence of ADA in all three arms.

Figure 28:
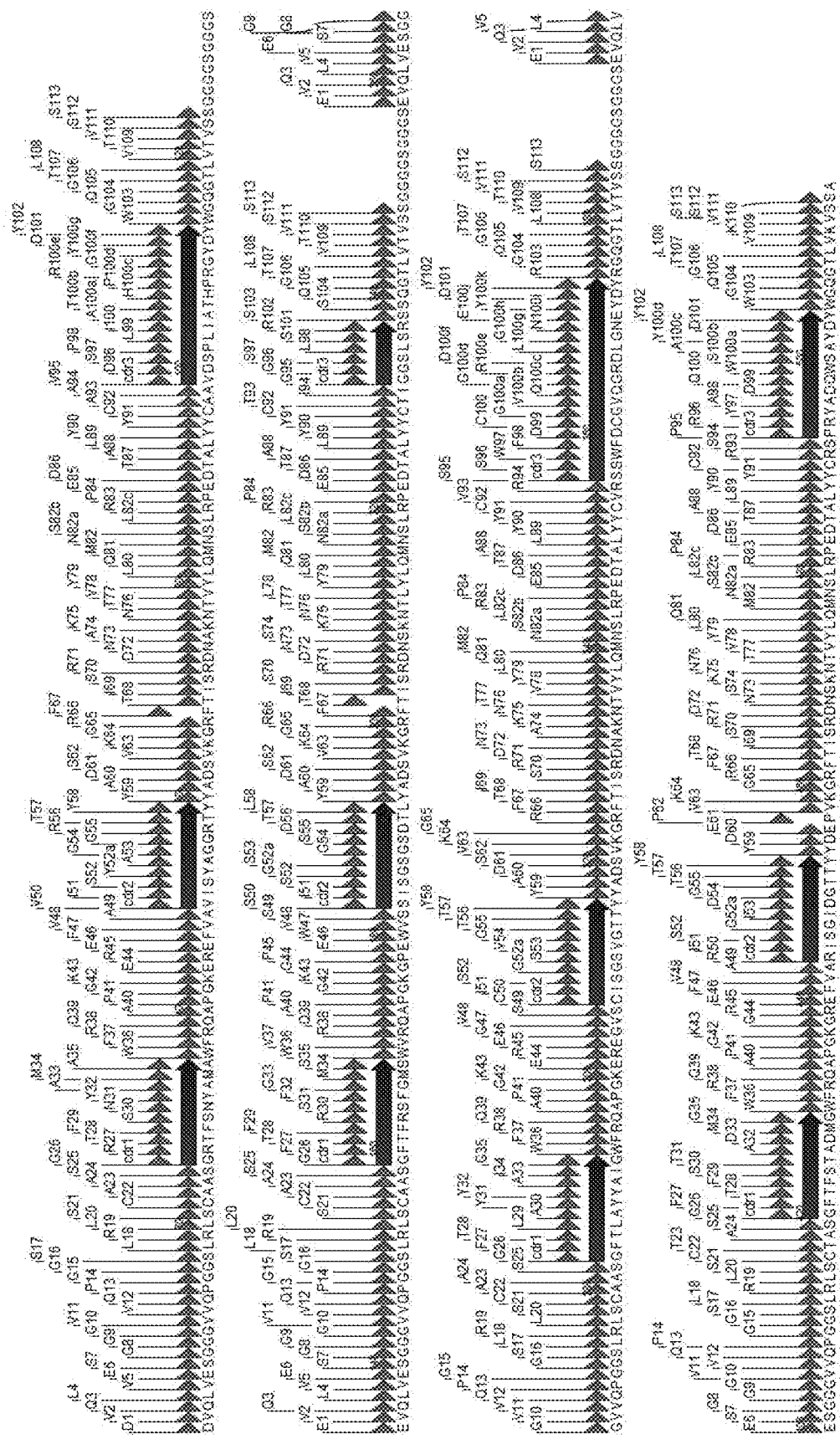

FIG. 28: F027201062 amino acid sequence (SEQ ID NO: 1),

5 DETAILED DESCRIPTION

The present disclosure provides a novel type of drug for treating inflammatory and/or autoimmune diseases, such as rheumatoid arthritis (RA).

The present inventors found that a polypeptide targeting TNF-α and IL-6 at the same time leads to an increased efficiency of modulating the symptoms of rheumatoid arthritis as compared to monospecific anti-TNF-α or anti-IL-6 polypeptides in vitro and/or in vivo. Said polypeptides could be efficiently produced (e.g. in microbial hosts). Furthermore, such polypeptides could be shown to have limited reactivity to pre-existing antibodies in the subject to be treated (i.e. antibodies present in the subject before the first treatment with the antibody construct). In some embodiments such polypeptides can be conveniently administered and exhibit a half-life in the subject to be treated that is long enough such that the number of consecutive treatments remains limited and thus these treatments can be conveniently spaced apart in time.

The polypeptide is at least bispecific, but can also be e.g., trispecific, tetraspecific or pentaspecific. Moreover, the polypeptide is at least trivalent, but can also be e.g. tetravalent, pentavalent or hexavalent, etc., preferably tetravalent.

The terms "bispecfic", "trispecific", "tetraspecific", or "pentaspecific" all fall under the term "multispecific" and refer to binding to two, three, four or five different target molecules, respectively. The terms "bivalent", "trivalent", "tetravalent", "pentavalent", or "hexavalent" all fall under the term "multivalent" and indicate the presence of two, three, four or five binding units (such as ISVDs), respectively. For example, the polypeptide may be trispecific-tetravalent, such as a polypeptide comprising or consisting of four ISVDs, wherein one ISVD binds to human TNF-α, two ISVDs bind to human IL-6 and one ISVD binds to human serum albumin (such as ISVD construct F027201062). Such a polypeptide may at the same time be biparatopic, for example if two ISVDs bind two different epitopes on human IL-6. The term "biparatopic" refers to binding to two different parts (e.g., epitopes) of the same target molecule.

The terms "first ISVD", "second ISVD", "third ISVD", etc., as used herein only indicate the presence of one, two or three, etc. ISVDs, but preferably also indicates the relative position of the ISVDs to each other, wherein the numbering is started from the N-terminus of the polypeptide of the present disclosure. The "first ISVD" is thus preferably closer to the N-terminus than the "second ISVD", whereas the "second ISVD" is closer to the N-terminus than the "third ISVD", etc. Accordingly, the ISVD arrangement is inverse when considered from the C-terminus. Since the numbering is not absolute and can only indicate the relative position of the at least three ISVDs it is not excluded that other binding units/building blocks such as additional ISVDs binding to TNF-α or IL-6, or ISVDs binding to another target may be present in the polypeptide. Moreover, it does not exclude the possibility that other binding units/building blocks such as ISVDs can be placed in between. For instance, as described further below (see in particular, section 5.3 "(In vivo) half-life extension"), the polypeptide can further comprise another ISVD binding to human serum albumin that can even be located, e.g., between the "first ISVD" and "second ISVD".

In light of the above, the disclosure provides a polypeptide comprising or consisting of at least three ISVDs, wherein at least one ISVD specifically binds to TNF-α and at least two ISVDs specifically bind to the IL-6.

The components, such as ISVDs, of the polypeptide may be linked to each other by one or more suitable linkers, such as peptidic linkers.

The use of linkers to connect two or more (poly)peptides is well known in the art. Exemplary peptidic linkers are shown in Table A-5. One often used class of peptidic linker are known as the "Gly-Ser" or "GS" linkers. These are linkers that essentially consist of glycine (G) and serine (5) residues, and usually comprise one or more repeats of a peptide motif such as the GGGGS (SEQ ID NO: 65) motif (for example, having the formula (Gly-Gly-Gly-Gly-Ser)$_n$ in which n may be 1, 2, 3, 4, 5, 6, 7 or more). Some often used examples of such GS linkers are 9GS linkers (GGGGSGGGS, SEQ ID NO: 68) 15GS linkers (n=3) and 35GS linkers (n=7). Reference is for example made to Chen et al., Adv. Drug Deliv. Rev. 2013 Oct. 15; 65(10): 1357-1369; and Klein et al., Protein Eng. Des. Set (2014) 27 (10): 325-330.

In the polypeptide of the present disclosure, in some embodiments, the use of 9GS linkers to link the components of the polypeptide to each other can be chosen.

In one embodiment, the ISVD specifically binding to TNF-α is positioned at the C-terminus of the polypeptide. The inventors surprisingly found that such a configuration can significantly increase the potency of the compound as well as improve several characteristics that are important for an optimal production of the compound, such as solubility and expression level.

Also, in one embodiment, one of the ISVDs specifically binding to IL-6 is positioned at the C-terminus or the N-terminus of the polypeptide, preferably at the N-terminus.

Accordingly, in some embodiments, the polypeptide comprises or consists of the following, in the order starting from the N-terminus of the polypeptide: a first ISVD specifically binding to IL-6, an optional binding unit providing the polypeptide with increased half-life as defined herein, a second ISVD specifically binding to IL-6, and a third ISVD specifically binding to TNF-α. In preferred embodiments, the binding unit providing the polypeptide with increased half-life is an ISVD.

It is provided that in some embodiments the polypeptide comprises or consists of the following, in the order starting from the N-terminus of the polypeptide: a first ISVD specifically binding to IL-6, a linker, an ISVD binding to human serum albumin (HSA), a linker, a second ISVD specifically binding to IL-6, a linker, and an ISVD specifically binding to TNF-α.

In some embodiments, the linker is a 9GS linker.

Such configurations of the polypeptide can provide for increased production yield, good CMC characteristics as well as optimized functionality and stronger potency with regard to modulation of an immune response.

Accordingly, in some embodiments, the polypeptide exhibits a solubility of at least 120 mg/ml, such as at least 130 mg/ml, such as at least 140 mg/ml, preferably at least 145 mg/ml.

In some embodiments, the polypeptide of the present disclosure exhibits reduced binding by pre-existing antibodies in human serum. To this end, in one embodiment, the polypeptide has a valine (V) at amino acid position 11 and a leucine (L) at amino acid position 89 (according to Kabat numbering) in at least one ISVD (preferably in at least the ISVD located at the C-terminus of the polypeptide), or in each ISVD. In another embodiment, the polypeptide has an extension of 1 to 5 amino acids, either naturally occurring, non-naturally occurring, or a mixture thereof, such as a single alanine (A) extension, at the C-terminus of the C-terminal ISVD. The C-terminus of an ISVD can be VTVSS (SEQ ID NO: 81). In another embodiment the polypeptide has a lysine (K) or glutamine (Q) at position 110 (according to Kabat numbering) in at least one ISVD (preferably in at least the ISVD located at the C-terminus of the polypeptide), or in each ISVD. In another embodiment, the ISVD has a lysine (K) or glutamine (Q) at position 112 (according to Kabat numbering) in at least one ISVD (preferably in at least the ISVD located at the C-terminus of the polypeptide), or in each ISVD. In some embodiments, the C-terminus of the ISVD is VKVSS (SEQ ID NO: 82), VQVSS (SEQ ID NO: 83), VTVKS (SEQ ID NO: 84), VTVQS (SEQ ID NO: 85), VKVKS (SEQ ID NO: 86), VKVQS (SEQ ID NO: 87), VQVKS (SEQ ID NO: 88), or VQVQS (SEQ ID NO: 89) such that after addition of a single alanine the C-terminus of the polypeptide for example has the sequence VTVSSA (SEQ ID NO: 90), VKVSSA (SEQ ID NO: 91), VQVSSA (SEQ ID NO: 92), VTVKSA (SEQ ID NO: 93), VTVQSA (SEQ ID NO: 94), VKVKSA (SEQ 10 NO: 95), VKVQSA (SEQ ID NO: 96), VQVKSA (SEQ 10 NO: 97), or VQVQSA (SEQ ID NO: 98). In one embodiment, the sequence is VKVSSA (SEQ ID NO: 91). In another embodiment, the polypeptide has a valine (V) at amino acid position 11 and a leucine (L) at amino acid position 89 (according to Kabat numbering) in each ISVD, optionally a lysine (K) or glutamine (Q), preferably K, at position 110 (according to Kabat numbering) in at least one ISVD (preferably in at least the ISVO located at the C-terminus of the polypeptide), and has an extension of 1 to 5 amino acids, either naturally occurring, non-naturally occurring, or a mixture thereof, such as a single alanine (A) extension, at the C-terminus of the C-terminal ISVD (such that the C-terminus of the polypeptide for example has the sequence VTVSSA (SEQ ID NO: 90), VKVSSA (SEQ ID NO: 91), or VQVSSA (SEQ ID NO: 92). See e.g. WO2012/175741 and WO2015/173325 for further information in this regard, each of which is hereby incorporated by reference in its entirety. The amino acid residues used for the extension are preferably independently selected from glycine, alanine, valine, leucine or isoleucine, more preferably from glycine and alanine, and most preferably alanine. Preferably, the extension consists of a single amino acid residue.

In one embodiment, the polypeptide of the present disclosure comprises or consists of an amino acid sequence having a sequence identity of more than 90%, such as more than 95% or more than 99%, with SEQ ID NO: 1, wherein the CDRs of the four ISVDs are as defined in items A to D (or A' to D' if using the Kabat definition) set forth in sections "0 immunoglobulin single variable domains" and "5.3 (in vivo) half-life extension" below, respectively, wherein in particular:

the first ISVD specifically binding to IL-6 has a CDR1 having the amino acid sequence of SEQ ID NO: 6, a CDR2 having the amino acid sequence of SEQ ID NO: 10 and a CDR3 having the amino acid sequence of SEQ ID NO: 14;

the second ISVD specifically binding to IL-6 has a CDR1 having the amino acid sequence of SEQ ID NO: 8, a CDR2 having the amino acid sequence of SEQ ID NO: 12 and a CDR3 having the amino acid sequence of SEQ ID NO: 16;

the ISVD specifically binding to TNF-α has a CDR1 having the amino acid sequence of SEQ ID NO: 9, a CDR2 having the amino acid sequence of SEQ ID NO: 13 and a CDR3 having the amino acid sequence of SEQ ID NO: 17; and the ISVD binding to human serum albumin has a CDR1 having the amino acid sequence of SEQ ID NO: 7, a CDR2 having the amino acid sequence of SEQ ID NO: 11 and a CDR3 having the amino acid sequence of SEQ ID NO: 15, or alternatively if using the Kabat definition:

the first ISVD specifically binding to IL-6 has a CDR1 having the amino acid sequence of SEQ ID NO: 33, a CDR2 having the amino acid sequence of SEQ ID NO: 37 and a CDR3 having the amino acid sequence of SEQ ID NO: 14;

the second ISVD specifically binding to IL-6 has a CDR1 having the amino acid sequence of SEQ ID NO: 35, a CDR2 having the amino acid sequence of SEQ ID NO: 39 and a CDR3 having the amino acid sequence of SEQ ID NO: 16;

the ISVD specifically binding to TNF-α has a CDR1 having the amino acid sequence of SEQ ID NO: 36, a CDR2 having the amino acid sequence of SEQ ID NO: 40 and a CDR3 having the amino acid sequence of SEQ ID NO: 17; and the ISVD binding to human serum albumin has a CDR1 having the amino acid sequence of SEQ ID NO: 34, a CDR2 having the amino acid sequence of SEQ ID NO: 38 and a CDR3 having the amino acid sequence of SEQ ID NO: 15.

In some embodiments, the polypeptide comprises or consists of the amino acid sequence of SEQ ID NO: 1. In one embodiment, the polypeptide consists of the amino acid sequence of SEQ ID NO: 1.

The polypeptide of the present disclosure in some embodiments has at least half the binding affinity, at least the same binding affinity, or even more binding affinity to human TNF-α and to human IL-6 as compared to a polypeptide consisting of the amino acid of SEQ ID NO: 1 wherein the binding affinity is measured using the same method, such as SPR.

5.1 Immunoglobulin Single Variable Domains

The term "immunoglobulin single variable domain" (ISVD), interchangeably used with "single variable domain", defines immunoglobulin molecules wherein the antigen binding site is present on, and formed by, a single immunoglobulin domain. This sets immunoglobulin single variable domains apart from "conventional" immunoglobulins (e.g. monoclonal antibodies) or their fragments (such as Fab, Fab', F(ab')$_2$, scFv, di-scFv), wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation. In view of the above definition, the antigen-binding domain of a conventional 4-chain antibody (such as an IgG, IgM, IgA, IgD or IgE molecule; known in the art) or of a Fab fragment, a F(ab')$_2$ fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single $V_H$, a single $V_{HH}$ or single $V_L$ domain.

As such, the single variable domain may be a light chain variable domain sequence (e.g., a $V_L$ sequence) or a suitable fragment thereof; or a heavy chain variable domain sequence (e.g., a $V_H$-sequence or $V_{HH}$ sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

An immunoglobulin single variable domain (ISVD) can for example be a heavy chain ISVD, such as a $V_H$, $V_{HH}$, including a camelized $V_H$ or humanized $V_{HH}$. According to some embodiments, an immunoglobulin single variable domain (ISVD) is a $V_{HH}$, including a camelized $V_H$ or humanized $V_{HH}$. Heavy chain ISVDs can be derived from a conventional four-chain antibody or from a heavy chain antibody.

For example, the immunoglobulin single variable domain may be a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$); other single variable domains, or any suitable fragment of any one thereof.

In particular, the immunoglobulin single variable domain may be a Nanobody® (such as a $V_{HH}$, including a humanized $V_{HH}$ or camelized $V_H$) or a suitable fragment thereof. Nanobody®, Nanobodies® and Nanoclone® are registered trademarks of Ablynx N.V.

"$V_{HH}$ domains", also known as $V_{HH}$s, $V_{HH}$ antibody fragments, and $V_{HH}$ antibodies, have originally been described as the antigen binding immunoglobulin variable domain of "heavy chain antibodies" (i.e., of "antibodies devoid of light chains"; Hamers-Casterman et al. Nature 363: 446-448, 1993). The term "Vim domain" has been chosen in order to distinguish these variable domains from the heavy chain variable domains that are present in conventional 4-chain antibodies (which are referred to herein as "$V_H$ domains") and from the light chain variable domains that are present in conventional 4-chain antibodies (which are referred to herein as "$V_L$ domains"). For a further description of $V_{HH}$'s, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V., each of which is hereby incorporated by reference in its entirety. Typically, the generation of immunoglobulins involves the immunization of experimental animals, fusion of immunoglobulin producing cells to create hybridomas and screening for the desired specificities. Alternatively, immunoglobulins can be generated by screening of naïve or synthetic libraries e.g. by phage display.

The generation of immunoglobulin sequences, such as Nanobodies®, has been described extensively in various publications, among which WO 94/04678, Hamers-Casterman et al. 1993 and Muyldermans et al. 2001 (Reviews in Molecular Biotechnology 74: 277-302, 2001) can be exemplified, each of which is hereby incorporated by reference in its entirety. In these methods, camelids are immunized with the target antigen in order to induce an immune response against said target antigen. The repertoire of Nanobodies obtained from said immunization is further screened for Nanobodies that bind the target antigen.

In these instances, the generation of antibodies requires purified antigen for immunization and/or screening. Antigens can be purified from natural sources, or in the course of recombinant production.

Immunization and/or screening for immunoglobulin sequences can be performed using peptide fragments of such antigens.

Immunoglobulin sequences of different origin may be used, comprising mouse, rat, rabbit, donkey, human and camelid immunoglobulin sequences. The disclosure also includes fully human, humanized or chimeric sequences. For example, the disclosure comprises camelid immunoglobulin sequences and humanized camelid immunoglobulin sequences, or camelized domain antibodies, e.g. camelized dAb as described by Ward et al (see for example WO 94/04678 and Riechmann, Febs Lett., 339:285-290, 1994 and Prot. Eng., 9:531-537, 1996, each of which is hereby incorporated by reference in its entirety). Moreover, the disclosure also uses fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221, each of which is hereby incorporated by reference in its entirety), and immunoglobulin sequences comprising tags or other functional moieties, e.g. toxins, labels, radiochemicals, etc., which are derivable from the immunoglobulin sequences of the present disclosure.

A "humanized $V_{HH}$" comprises an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and in the literature (e.g. WO 2008/020079, Incorporated by reference in its entirety). Again. It should be noted that such humanized $V_{HH}$s can be obtained in any suitable manner known per se and thus are not strictly limited to polypeptides that have been obtained using a polypeptide that comprises a naturally occurring VHH domain as a starting material.

A "camelized $V_H$" comprises an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein and the literature (e.g. WO 2008/020079). Such "camelizing" substitutions can be inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). In some embodiments, the $V_H$ sequence that is used as a starting material or starting point for generating or designing the camelized $V_H$ is a $V_H$ sequence from a mammal, or the $V_H$ sequence of a human being, such as a $V_H$3 sequence. However, it should be noted that such camelized $V_H$ can be obtained in any suitable manner known per se and thus are not strictly limited to polypeptides that have been obtained using a polypeptide that comprises a naturally occurring $V_H$ domain as a starting material.

It should be noted that one or more immunoglobulin sequences may be linked to each other and/or to other amino acid sequences (e.g. via disulphide bridges) to provide peptide constructs that may also be useful (for example Fab' fragments, F(ab')2 fragments, scFv constructs, "diabodies" and other multispecific constructs). Reference is for example made to the review by Holliger and Hudson, Nat Biotechnol. 2005 September; 23(9):1126-36)). Generally, when a polypeptide is intended for administration to a subject (for example for prophylactic, therapeutic and/or diagnostic purposes), it may comprise an immunoglobulin sequence that does not occur naturally in said subject.

A non-limiting example of structure of an immunoglobulin single variable domain sequence can be considered to be comprised of four framework regions ("FRs"), which are referred to in the art and herein as "Framework region 1" ("FR1"); as "Framework region 2" ("FR2"); as "Framework region 3" ("FR3"); and as "Framework region 4" ("FR4"), respectively; which framework regions are interrupted by three complementary determining regions ("CDRs"), which are referred to in the art and herein as "Complementarity Determining Region 1" ("CDR1"); as "Complementarity Determining Region 2" ("CDR2"); and as "Complementarity Determining Region 3" ("CDR3"), respectively.

As further described in paragraph q) on pages 58 and 59 of WO 08/020079 (incorporated herein by reference), the amino acid residues of an immunoglobulin single variable domain can be numbered according to the general numbering for $V_H$ domains given by Kabat et al. ("Sequence of proteins of immunological interest", US Public Health Services, NIH Bethesda, MD, Publication No. 91), as applied to $V_{HH}$ domains from Camelids in the article of Riechmann and Muyldermans, 2000 (J. Immunol. Methods 240 (1-2): 185-195; see for example FIG. 2 of this publication). It should be noted that—as is well known in the art for $V_H$ domains and for $V_{HH}$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a $V_H$ domain and a $V_{HH}$ domain will usually be in the range of from 110 to 120, often between 112 and 115. It should however be noted that smaller and longer sequences may also be suitable for the purposes described herein.

In the present application, unless indicated otherwise, CDR sequences were determined according to the AbM numbering as described in Kontermann and Dubel (Eds. 2010, Antibody Engineering. vol 2, Springer Verlag Heidelberg Berlin, Martin, Chapter 3, pp. 33-51). According to this method, FR1 comprises the amino acid residues at positions 1-25, CDR1 comprises the amino add residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Determination of CDR regions may also be done according to different methods. In the CDR determination according to Kabat, FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

In such an immunoglobulin sequence, the framework sequences may be any suitable framework sequences, and examples of suitable framework sequences will be clear to the skilled person, for example on the basis the standard handbooks and the further disclosure and prior art mentioned herein.

The framework sequences can be (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence or $V_{HH}$ sequence). In one embodiment, the framework sequences are either framework sequences that have been derived from a $V_{HH}$-sequence (in which said framework sequences may optionally have been partially or fully humanized) or are conventional $V_H$ sequences that have been camelized (as defined herein).

In particular, the framework sequences present in the ISVD sequence as disclosed herein may contain one or more of hallmark residues (as defined herein), such that the ISVD sequence is a Nanobody®, such as a $V_{HH}$, including a humanized $V_{HH}$ or camelized $V_H$. Some non-limiting examples of (suitable combinations of) such framework sequences will become dear from the further disclosure herein.

Again, as generally described herein for the immunoglobulin sequences, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived).

However, it should be noted that the disclosure is not limited as to the origin of the ISVD sequence (or of the nucleotide sequence used to express it), nor as to the way that the ISVD sequence or nucleotide sequence is (or has been) generated or obtained. Thus, the ISVD sequences may be naturally occurring sequences (from any suitable species) or synthetic or semi-synthetic sequences. In a specific but non-limiting aspect, the ISVD sequence is a naturally occurring sequence (from any suitable species) or a synthetic or semi-synthetic sequence, including but not limited to "humanized" (as defined herein) immunoglobulin sequences (such as partially or fully humanized mouse or rabbit immunoglobulin sequences, and in particular partially or fully humanized $V_{HH}$ sequences), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

Similarly, nucleotide sequences may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

As described above, an ISVD may be a Nanobody® or a suitable fragment thereof. For a general description of Nanobodies® (Nanobody® and Nanobodles® are registered trademarks of Ablynx N.V., a Sanofi Company), reference is made to the further description below, as well as to the prior art cited herein. In this respect, it should however be noted that this description and the prior art mainly described Nanobodies® of the so-called "$V_H3$ class" (i.e. Nanobodies® with a high degree of sequence homology to human germline sequences of the $V_H3$ class such as DP-47, DP-51 or DP-29). It should however be noted that the disclosure in its broadest sense can generally use any type of Nanobody®, and for example also uses the Nanobodies® belonging to the so-called "$V_H4$ class" (i.e. Nanobodies® with a high degree of sequence homology to human germline sequences of the $V_H4$ class such as DP-78), as for example described in WO 2007/118670, incorporated by reference in its entirety.

Generally, Nanobodies® (in particular $V_{HH}$ sequences, including (partially) humanized $V_{HH}$ sequences and camelized $V_H$ sequences) can be characterized by the presence of one or more "Hallmark residues" (as described herein) in one or more of the framework sequences (again as further described herein). Thus, generally, a Nanobody® can be defined as an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody® can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody® can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which: one or more of the amino acid residues at positions 11, 37, 44, 45, 47, 83, 84, 103, 104 and 108 according to the Kabat numbering are chosen from the Hallmark residues mentioned in Table X below.

The FRs indicated herein can suitably be selected from the FRs as indicated in Table A-2 (or Table A-2.1 for Kabat numbering), preferably from the same clone (i.e. FRs shown in the same line), optionally with amino acids at specific positions as described herein.

TABLE X

Hallmark Residues in Nanobodies ®

| Position | Human V$_H$3 | Hallmark Residues |
|---|---|---|
| 11 | L, V; predominantly L | L, S, V, M, W, F, T, Q, E, A, R, G, K, Y, N, P, I |
| 37 | V, I, F; usually V | F$^{(1)}$, Y, V, L, A, H, S, I, W, C, N, G, D, T, P |
| 44$^{(8)}$ | G | E$^{(3)}$, Q$^{(3)}$, G$^{(2)}$, D, A, K, R, L, P, S, V, H, T, N, W, M, I |
| 45$^{(8)}$ | L | L$^{(2)}$, R$^{(3)}$, P, H, F, G, Q, S, E, T, Y, C, I, D, V |
| 47$^{(8)}$ | W, Y | F$^{(1)}$, L$^{(1)}$ or W$^{(2)}$ G, I, S, A, V, M, R, Y, E, P, T, C, H, K, Q, N, D |
| 83 | R or K; usually R | R, K$^{(5)}$, T, E$^{(5)}$, Q, N, S, I, V, G, M, L, A, D, Y, H |
| 84 | A, T, D; predominantly A | P$^{(5)}$, S, H, L, A, V, I, T, F, D, R, Y, N, Q, G, E |
| 103 | W | W$^{(4)}$, R$^{(6)}$, G, S, K, A, M, Y, L, F, T, N, V, Q, P$^{(6)}$, E, C |
| 104 | G | G, A, S, T, D, P, N, E, C, L |
| 108 | L, M or T; predominantly L | Q, L$^{(7)}$, R, P, E, K, S, T, M, A, H |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible sequences include for example DECKL and NVCEL.
$^{(4)}$With both GLEW at positions 44-47 and KERE or KQRE at positions 43-46.
$^{(5)}$Often as KP or EP at positions 83-84 of naturally occurring V$_{HH}$ domains.
$^{(6)}$In particular, but not exclusively, in combination with GLEW at positions 44-47.
$^{(7)}$With the proviso that when positions 44-47 are GLEW, position 108 is always Q in (non-humanized) V$_{HH}$ sequences that also contain a W at 103.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

In some embodiments, the hallmark residue at position 11 is L. In some embodiments, the hallmark residue at position 37 is F$^{(1)}$ or Y. In some embodiments, the hallmark residue at position 44 is G$^{(2)}$ or Q$^{(3)}$. In some embodiments, the hallmark residue at position 45 is L$^{(2)}$ or R$^{(3)}$. In some embodiments, the hallmark residue at position 47 is F$^{(1)}$, L$^{(1)}$, or W$^{(2)}$. In some embodiments, the hallmark residue at position 83 is K. In some embodiments, the hallmark residue at position 84 is P. In some embodiments, the hallmark residue at position 103 is W. In some embodiments, the hallmark residue at position 104 is G. In some embodiments, the hallmark residue at position 108 is Q or L.

Moreover, when an ISVD having an N-terminal glutamic acid (E) at position 1 is located at the N-terminus of the polypeptide, the glutamic acid is preferably substituted by aspartic acid (D). Thus, for example, if SEQ ID NOs: 3, 4 or 5 are at the N-terminus of the polypeptide, E at position 1 can be changed to D. Conversely, if, for example, SEQ ID NO: 2 is not present at the N-terminus of the polypeptide, the D at position 1 can be changed into E.

The disclosure inter alia uses ISVDs that can specifically bind to TNF-α or IL-6. In the context of the present disclosure, "binding to" a certain target molecule has the usual meaning in the art as understood in the context of antibodies and their respective antigens.

The polypeptide of the present disclosure may comprise one or more ISVDs binding to TNF-α and two or more ISVDs binding to IL-6. For example, the polypeptide may comprise one ISVD that binds to TNF-α and two ISVDs that bind to IL-6.

In some embodiments, at least one ISVD can functionally block its target molecule. For example, targeting moieties can block the interaction between TNF-α and TNFR (TNF receptor), or can block the interaction between IL-6 and IL-6R (Interleukin 6 receptor). Accordingly, in one embodiment, the polypeptide of the present disclosure comprises at least one ISVD that specifically binds to TNF-α and inhibits its interaction with TNFR, and two ISVDs that specifically bind to IL-6 and functionally block its interaction with IL-6R. Accordingly, in a preferred embodiment, the polypeptide of the present disclosure comprises two ISVDs that specifically bind to IL-6, one of which functionally blocks the interaction of IL-6 with IL-6R.

The ISVDs used in the disclosure form part of a polypeptide of the present disclosure, which comprises or consists of at least three ISVDs, such that the polypeptide can specifically bind to TNF-α and IL-6.

Accordingly, the target molecules for the at least three ISVDs as used in the polypeptide of the present disclosure are TNF-α and IL-6. Examples are mammalian TNF-α and IL-6. While human TNF-α (Uniprot accession P01375) and human IL-6 (Uniprot accession P05231) can be used, the versions from other species are also amenable to the present disclosure, for example TNF-α and IL-6 from mice, rats, rabbits, cats, dogs, goats, sheep, horses, pigs, non-human primates, such as cynomolgus monkeys (also referred to herein as "cyno"), or camelids, such as llama or alpaca.

Specific examples of ISVDs specifically binding to TNF-α or IL-6 that can be used in the disclosure are as described in the following items A to C:

A. An ISVD that specifically binds to human IL-6 and comprises i. a CDR1 which has the amino acid sequence of SEQ ID NO: 6 amino acid difference with SEQ ID NO: 6;

ii. a CDR2 which has the amino acid sequence SEQ ID NO: 10 amino acid difference with SEQ ID NO: 10; and iii. a CDR3 which has the amino acid sequence of SEQ 10 NO: 14 amino acid difference with SEQ ID NO: 14, In some embodiments, the CDR1 has the amino acid sequence of SEQ ID NO: 6, the CDR2 has the amino acid sequence of SEQ ID NO: 10, and the CDR3 has the amino acid sequence of SEQ ID NO: 14.

Non-limiting examples of such an ISVD that specifically binds to human IL-6 have one or more, or all, framework regions as indicated for construct 17C04 in Table A-2 (in addition to the CDRs as defined in the preceding item A), such as an ISVD having the full amino acid sequence of construct 17C04 (SEQ ID NO: 2, see Table A-1 and A-2).

Also, in one embodiment, the amino acid sequence of the ISVD specifically binding to human IL-6 may have a sequence identity of more than 90%, such as more than 95% or more than 99%, with SEQ ID NO: 2, wherein optionally the CDRs are as defined in the preceding item A.

In some embodiments, the ISVD specifically binding to IL-6 has the amino acid sequence of SEQ ID NO: 2.

When such an ISVD specifically binding to IL-6 has 2 or 1 amino acid difference in at least one CDR relative to a corresponding reference CDR sequence (item A above), in some embodiments, the ISVD has at least half the binding affinity, preferably at least the same binding affinity, or even higher binding affinity to human IL-6 as construct 17C04, wherein the binding affinity is measured using the same method, such as SPR.

B. An ISVD that specifically binds to human IL-6 and comprises
- i. a CDR1 which has the amino add sequence SEQ ID NO: 8 amino acid difference with SEQ ID NO: 8;
- ii. a CDR2 which has the amino acid sequence SEQ ID NO: 12 amino acid difference with SEQ ID NO: 12; and
- iii. a CDR3 which has the amino acid sequence SEQ ID NO: 16 amino acid difference with SEQ ID NO: 16,
- In some embodiments, the CDR1 has the amino acid sequence of SEQ ID NO: 8, the CDR2 has the amino acid sequence of SEQ ID NO: 12 and the CDR3 has the amino acid sequence of SEQ ID NO: 16.

Non-limiting examples of such an ISVD that specifically binds to human IL-6 have one or more, or all, framework regions as indicated for construct 6812 in Table A-2 (in addition to the CDRs as defined in the preceding item B), such as an ISVD having the full amino acid sequence of construct 6112 (SEQ ID NO: 4, see Table A-1 and A-2).

Also, in one embodiment, the amino acid sequence of an ISVD specifically binding to human IL-6 may have a sequence identity of more than 90%, such as more than 95% or more than 99%, with SEQ ID NO: 4, wherein optionally the CDRs are as defined in the preceding item B. In some embodiments, the ISVD binding to IL-6 has the amino acid sequence of SEQ ID NO: 4.

When such an ISVD binding to IL-6 has 2 or 1 amino acid difference in at least one CDR relative to a corresponding reference CDR sequence (item 8 above), in some embodiments, the ISVD has at least half the binding affinity, at least the same binding affinity, or even higher binding affinity to human IL-6 as construct 6812, wherein the binding affinity is measured using the same method, such as SPR.

C. An ISVD that specifically binds to human TNF-α and comprises
- i. a CDR1 which has the amino acid sequence of SEQ ID NO: 9 amino acid difference with SEQ ID NO: 9;
- ii. a CDR2 which has the amino acid sequence of SEQ ID NO: 13 amino acid difference with SEQ ID NO: 13; and
- iii. a CDR3 which has the amino acid sequence of SEQ ID NO: 17 amino acid difference with SEQ ID NO: 17,
- In some embodiments, the CDR1 has the amino acid sequence of SEQ ID NO: 9, the CDR2 has the amino acid sequence of SEQ ID NO: 13 and the CDR3 has the amino acid sequence of SEQ ID NO: 17.

Non-limiting examples of such an ISVD that specifically binds to human TNF-α have one or more, or all, framework regions as indicated for construct 6C11 in Table A-2 (in addition to the CDRs as defined in the preceding item C), such as an ISVD having the full amino acid sequence of construct 6C11 (SEQ ID NO: 5, see Table A-1 and A-2).

Also, in one embodiment, the amino acid sequence of an ISVD specifically binding to human TNF-α may have a sequence identity of more than 90%, such as more than 95% or more than 99%, with SEQ ID NO: 5, wherein optionally the CDRs are as defined in the preceding item C.

In some embodiments, the ISVD binding to TNF-α has the amino acid sequence of SEQ ID NO: 5.

When such an ISVD specifically binding to TNF-α has 2 or 1 amino acid difference in at least one CDR relative to a corresponding reference CDR sequence (item C above), the ISVD has at least half the binding affinity, at least the same binding affinity, or even higher binding affinity to human TNF-α as construct 6C11, wherein the binding affinity is measured using the same method, such as SPR.

In some embodiments, each of the ISVDs as defined under items A to C above is comprised in the polypeptide of the present disclosure. In some embodiments, such a polypeptide of the present disclosure comprising each of the ISVDs as defined under items A to C above has at least half the binding affinity, at least the same binding affinity, or even more binding affinity to human TNF-α and to human IL-6 as a polypeptide consisting of the amino acid of SEQ ID NO: 1, wherein the binding affinity is measured using the same method, such as SPR. The SEQ ID NOs referred to in the above items A to C are based on the CDR definition according to the AbM definition (see Table A-2). It is noted that the SEQ ID NOs defining the same CDRs according to the Kabat definition (see Table A-2.1) can likewise be used in the above items A to C.

Accordingly, the specific ISVDs specifically binding to TNF-α or IL-6 that can be used in the disclosure as described above using the AbM definition can be also described using the Kabat definition asset forth in items A' to C' below:

A'. An ISVD that specifically binds to human IL-6 and comprises
- i. a CDR1 which has the amino acid sequence of SEQ ID NO: 33 amino acid difference with SEQ ID NO: 33;
- ii. a CDR2 which has the amino acid sequence SEQ ID NO: 37 amino acid difference with SEQ ID NO: 37; and
- iii. a CDR3 which has the amino acid sequence of SEQ ID NO: 14 amino acid difference with SEQ ID NO: 14,
- In some embodiments, the CDR1 has the amino acid sequence of SEQ 10 NO: 33, the CDR2 has the amino acid sequence of SEQ ID NO: 37 and the CDR3 has the amino acid sequence of SEQ ID NO: 14.

Non-limiting examples of such an ISVD that specifically binds to human IL-6 have one or more, or all, framework regions as indicated for construct 17C04 In Table A-2.1 (in addition to the CDRs as defined in the preceding item A'), such as an ISVD having the full amino acid sequence of construct 17C04 (SEQ ID NO: 2, see Table A-1 and A-2.1).

B'. An ISVD that specifically binds to human IL-6 and comprises
- i. a CDR1 which has the amino acid sequence SEQ ID NO: 35 amino acid difference with SEQ ID NO: 35;
- ii. a CDR2 which has the amino acid sequence SEQ ID NO: 39 amino acid difference with SEQ ID NO: 39; and
- iii. a CDR3 which has the amino acid sequence SEQ ID NO: 16 amino acid difference with SEQ ID NO: 16,
- In some embodiments, the CDR1 has the amino acid sequence of SEQ ID NO: 35, the CDR2 has the amino acid sequence of SEQ ID NO: 39 and the CDR3 has the amino acid sequence of SEQ ID NO: 16.

Non-limiting examples of such an ISVD that specifically binds to human IL-6 have one or more, or all, framework regions as indicated for construct 6812 in Table A-2.1 (in addition to the CDRs as defined in the preceding item B'), such as an ISVD having the full amino acid sequence of construct 6812 (SEQ ID NO: 4, see Table A-1 and A-2.1).

C'. An ISVD that specifically binds to human TNF-α and comprises
- i. a CDR1 which has the amino acid sequence of SEQ ID NO: 36 amino acid difference with SEQ ID NO: 36;
- ii. a CDR2 which has the amino acid sequence of SEQ ID NO: 40 amino acid difference with SEQ ID NO: 40; and
- iii. a CDR3 which has the amino acid sequence of SEQ ID NO: 17 amino acid difference with SEQ ID NO: 17, In some embodiments, the CDR1 has the amino acid sequence of SEQ ID NO: 36, the CDR2 has the amino acid sequence of SEQ ID NO: 40 and the CDR3 has the amino acid sequence of SEQ ID NO: 17.

Non-limiting examples of such an ISVD that specifically binds to human TNF-α have one or more, or all, framework regions as indicated for construct 6C11 in Table A-2.1 (in addition to the CDRs as defined in the preceding item C'), such as an ISVD having the full amino acid sequence of construct 6C11(SEQ ID NO: 5, see Table A-1 and A-2.1).

The percentage of "sequence identity" between a first amino acid sequence and a second amino acid sequence may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (i.e. at a single position).

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

An "amino acid difference" as used herein refers to a deletion, insertion or substitution of a single amino acid residue vis-4-vis a reference sequence. In some embodiments, the amino acid difference is a substitution. Fewer amino acid differences with a given reference sequence are generally preferred. For example, where a CDR has 2 or 1 amino acid difference with a given SEQ ID NO, 1 amino acid difference is preferred.

In some embodiments, the amino acid substitutions are conservative substitutions. In some embodiments, such conservative substitutions are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

In some embodiments, the conservative substitutions are as follows: Ala into Gly or into Ser; Arg into Lys; Asn into Gin or into His; Asp into Glu; Cys into Ser; Gin into Asn; Glu into Asp; Gly into Ala or into Pro; His into Asn or into Gin; lie into Leu or into Val; Leu into lie or into Val; Lys into Arg, into Gin or into Glu; Met into Leu, into Tyr or into lie; Phe into Met, into Leu or into Tyr; Ser into Thr; Thr into Ser; Trp into Tyr; Tyr into Trp; and/or Phe into Val, into lie or into Leu.

5.2 Specificity

The terms "specificty", "binding specifically" or "specific binding" refer to the number of different target molecules, such as antigens, from the same organism to which a particular binding unit, such as an ISVD, can bind with sufficiently high affinity (see below). "Specificity", "binding specifically" or "specific binding" are used interchangeably herein with "selectivity", "binding selectively" or "selective binding". According to some embodiments, binding units, such as ISVDs, specifically bind to their designated targets.

The specificity/selectivity of a binding unit can be determined based on affinity. The affinity denotes the strength or stability of a molecular interaction. The affinity is commonly given as by the KD, or dissociation constant, which has units of mol/liter (or M). The affinity can also be expressed as an association constant, KA, which equals 1/KD and has units of (mol/liter)$^{-1}$ (or M$^{-1}$).

The affinity is a measure for the binding strength between a moiety and a binding site on the target molecule: the lesser the value of the KD, the stronger the binding strength between a target molecule and a targeting moiety.

Typically, binding units used in the present disclosure (such as ISVDs) will bind to their targets (at room temperature) with a dissociation constant (KD) of $10^{-5}$ to $10^{-12}$ moles/liter or less, such as $10^{-7}$ to $10^{-12}$ moles/liter or less, more particularly such as $10^{-8}$ to $10^{-12}$ moles/liter (i.e. with an association constant (KA) of $10^5$ to $10^{12}$ liter/moles or more, such as $10^7$ to $10^{12}$ liter/moles or more and more particularly such as $10^8$ to $10^{12}$ liter/moles).

Any KD value greater than $10^{-4}$ mol/liter (or any KA value lower than $10^4$ liters/mol) is generally considered to indicate non-specific binding.

The KD for biological interactions, such as the binding of immunoglobulin sequences to an antigen, which are considered specific are typically in the range of $10^{-5}$ moles/liter (10000 nM or 10 μM) to $10^{-12}$ moles/liter (0.001 nM or 1 pM) or less.

Accordingly, specific/selective binding may mean that—using the same measurement method, e.g. SPR—a binding unit (or polypeptide comprising the same) binds to TNF-α and/or IL-6 with a KD value of $10^{-5}$ to $10^{-12}$ moles/liter or less and binds to related cytokines with a KD value greater than $10^{-4}$ moles/liter. Examples of related cytokines for TNF-α are TNF superfamily members FASL, TNFβ, LIGHT, TL-1A, RANKL. Examples of related cytokines for IL-6 are IL-6-family members IL-11, ciliary neurotrophic factor (CNTF), leukemia inhibitory factor (LIF), oncostatin M (OSM), cardiotrophin 1 (CT-1), cardiotrophin-like cytokine (CLC), and IL-27. Thus, in an embodiment, at least one ISVD comprised in the polypeptide binds to TNF-α with a KD value of $10^{-5}$ to $10^{-12}$ moles/liter or less and binds to FASL, TNFβ, LIGHT, TL-1A, RANKL of the same species with a KD value greater than $10^{-4}$ moles/liter, and at least two ISVDs comprised in the polypeptide bind to IL-6 with a KD value of $10^{-5}$ to $10^{-12}$ moles/liter or less and binds to IL-11, ciliary neurotrophic factor (CNTF), leukemia inhibitory factor (LIF), oncostatin M (OSM), cardiotrophin 1 (CT-1), cardiotrophin-like cytokine (CLC), It-27 of the same species with a KD value greater than $10^{-4}$ moles/liter.

Thus, in some embodiments, the polypeptide of the present disclosure has at least half the binding affinity, at least the same binding affinity, or even higher binding affinity to human TNF-α and to human IL-6 as compared to a polypeptide consisting of the amino acid of SEQ ID NO: 1, wherein the binding affinity is measured using the same method, such as SPR.

Specific binding to a certain target from a certain species does not exclude that the binding unit can also specifically bind to the analogous target from a different species. For example, specific binding to human TNF-α does not exclude that the binding unit (or a polypeptide comprising the same) can also specifically bind to TNF-α from cynomolgus monkeys. Likewise, for example, specific binding to human IL-6 does not exclude that the binding unit (or a polypeptide comprising the same) can also specifically bind to IL-6 from cynomolgus monkeys ("cyno").

Specific binding of a binding unit to its designated target can be determined in any suitable manner known per se, Including, but not limited to, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned below. In this respect, it will also be clear that it may not be possible to measure dissociation constants of more than $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant (KA), by means of the relationship (KD=1/KA).

The affinity of a molecular interaction between two molecules can be measured via different techniques known per se, such as the well-known surface plasmon resonance (SPR) biosensor technique (see for example Ober et al. 2001, Intern. Immunology 13: 1551-1559). The term "surface plasmon resonance", as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIAcore® system (BIAcore International AB, a GE Healthcare company, Uppsala, Sweden and Piscataway, NJ). For further descriptions, see Jonsson et al. (1993, Ann. Biol. Clin. 51: 19-26), Jonsson et al. (1991 Biotechniques 11: 620-627), Johnsson et al. (1995, J. Mol. Recognit. 8: 125-131), and Johnsson et al. (1991, Anal. Biochem. 198: 268-277).

Another well-known biosensor technique to determine affinities of biomolecular interactions is bio-layer interferometry (BLU) (see for example Abdiche et al. 2008, Anal. Biochem. 377: 209-217). The term "bio-layer interferometry" or "BLI", as used herein, refers to a label-free optical technique that analyzes the interference pattern of light reflected from two surfaces: an internal reference layer (reference beam) and a layer of immobilized protein on the biosensor tip (signal beam). A change in the number of molecules bound to the tip of the biosensor causes a shift in the interference pattern, reported as a wavelength shift (nm), the magnitude of which is a direct measure of the number of molecules bound to the biosensor tip surface. Since the interactions can be measured in real-time, association and dissociation rates and affinities can be determined. BLI can for example be performed using the well-known Octet® Systems (ForteBio, a division of Pall Life Sciences, Menlo Park, USA).

Alternatively, affinities can be measured in Kinetic Exclusion Assay (KinExA) (see for example Drake et al. 2004, Anal. Biochem., 328: 35-43), using the KinExA® platform (Sapidyne Instruments Inc, Boise, USA). The term "KinExA", as used herein, refers to a solution-based method to measure true equilibrium binding affinity and kinetics of unmodified molecules. Equilibrated solutions of an antibody/antigen complex are passed over a column with beads precoated with antigen (or antibody), allowing the free antibody (or antigen) to bind to the coated molecule. Detection of the antibody (or antigen) thus captured is accomplished with a fluorescently labeled protein binding the antibody (or antigen).

The GYROLAB® immunoassay system provides a platform for automated bioanalysis and rapid sample turnaround (Fraley et al. 2013, Bioanalysis 5: 1765-74).

5.3 (In Vivo) Half-Life Extension

The polypeptide may further comprise one or more other groups, residues, moieties or binding units, optionally linked via one or more peptidic linkers, in which said one or more other groups, residues, moieties or binding units provide the polypeptide with increased (in vivo) half-life, compared to the corresponding polypeptide without said one or more other groups, residues, moieties or binding units. In vivo half-life extension means, for example, that the polypeptide has an increased half-life in a mammal, such as a human subject, after administration. Half-life can be expressed for example as t1/2beta.

The type of groups, residues, moieties or binding units is not generally restricted and may for example be chosen from the group consisting of a polyethylene glycol molecule, serum proteins or fragments thereof, binding units that can bind to serum proteins, an Fc portion, and small proteins or peptides that can bind to serum proteins.

More specifically, said one or more other groups, residues, moieties or binding units that provide the polypeptide with increased half-life can be chosen from the group consisting of binding units that can bind to serum albumin, such as human serum albumin, or a serum immunoglobulin, such as IgG. In some embodiments, the binding unit can bind to human serum albumin. In some embodiments, the binding unit is an ISVD.

For example, WO 04/041865 (incorporated by reference in its entirety) describes Nanobodies® binding to serum albumin (and in particular against human serum albumin) that can be linked to other proteins (such as one or more other Nanobodies® binding to a desired target) in order to increase the half-life of said protein.

The International application WO 06/122787 (incorporated by reference in its entirety) describes a number of Nanobodies® against (human) serum albumin. These Nanobodies® include the Nanobody® called Alb-1 (SEQ ID NO: 52 in WO 06/122787, incorporated by reference in its entirety) and humanized variants thereof, such as Alb-8 (SEQ ID NO: 62 In WO 06/122787, incorporated by reference in its entirety). Again, these can be used to extend the half-life of therapeutic proteins and polypeptide and other therapeutic entities or moieties.

Moreover, WO2012/175400 (incorporated by reference in its entirety) describes a further improved version of Alb-1, called Alb-23.

In one embodiment, the polypeptide comprises a serum albumin binding moiety selected from Alb-1, Alb-3, Alb-4, Alb-5, Alb-6, Alb-7, Alb-8, Alb-9, Alb-10 and Alb-23. In some embodiments, the polypeptide comprises Alb-8 or Alb-23, or its variants, as shown on pages 7-9 of WO2012/175400 and the albumin binders described in WO2012/175741, WO2015/173325, WO2017/080850, WO2017/085172, WO2018/104444, WO2018/134235, WO2018/134234, each of which is herein incorporated by reference in its entirety. Some non-limiting examples of serum albumin binders are also shown in Table A-4. In some embodiments, the polypeptide of the present disclosure comprises a further component as described in item D:

D. An ISVD that binds to human serum albumin and comprises
   i. a CDR1 which has the amino acid sequence of SEQ ID NO: 7 amino acid difference with SEQ ID NO: 7;
   ii. a CDR2 which has the amino acid sequence of SEQ ID NO: 11 amino acid difference with SEQ ID NO: 11; and
   iii. a CDR3 which has the amino acid sequence of SEQ 10 NO: 15 amino acid difference with SEQ ID NO: 15;

In some embodiments, the CDR1 has the amino acid sequence of SEQ ID NO: 7, the CDR2 has the amino acid sequence of SEQ ID NO: 11 and the CDR3 has the amino acid sequence of SEQ ID NO: 15.

Non-limiting examples of such an ISVD that binds to human serum albumin have one or more, or all, framework regions as indicated for construct ALB23002 in Table A-2 (in addition to the CDRs as defined in the preceding item D), such as an ISVD having the full amino acid sequence of construct ALB23002 (SEQ ID NO: 3, see Table A-1 and A-2).

Item D can be also described using the Kabat definition as:

D'. An ISVD that binds to human serum albumin and comprises
   i. a CDR1 which has the amino acid sequence of SEQ ID NO: 34 amino acid difference with SEQ ID NO: 34;
   ii. a CDR2 which has the amino acid sequence of SEQ 10 NO: 38 amino acid difference with SEQ ID NO: 38; and
   iii. a CDR3 which has the amino acid sequence of SEQ ID NO: 15 amino acid difference with SEQ ID NO: 15;

In some embodiments, the CDR1 has the amino acid sequence of SEQ ID NO: 34, the CDR2 has the amino acid sequence of SEQ ID NO: 38 and the CDR3 has the amino acid sequence of SEQ ID NO: 15.

Non-limiting examples of such an ISVD that binds to human serum albumin have one or more, or all, framework regions as indicated for construct ALB23002 in Table A-2.1 (in addition to the CDRs as defined in the preceding item D'), such as an ISVD having the full amino acid sequence of construct ALB23002 (SEQ ID NO: 3, see Table A-1 and A-2.1).

Also in one embodiment, the amino acid sequence of an ISVD binding to human serum albumin may have a sequence identity of more than 90%, such as more than 95% or more than 99%, with SEQ ID NO: 3, wherein optionally the CDRs are as defined in the preceding item D. In some embodiments, the ISVD binding to human serum albumin has the amino acid sequence of SEQ ID NO: 3.

When such an ISVD binding to human serum albumin has 2 or 1 amino acid difference in at least one CDR relative to a corresponding reference CDR sequence (item D above), the ISVD has at least half the binding affinity, at least the same binding affinity, or even higher binding affinity to human serum albumin as construct ALB23002, wherein the binding affinity is measured using the same method, such as SPR.

When such an ISVD binding to human serum albumin has a C-terminal position it exhibits a C-terminal alanine (A) or glycine (G) extension and can be selected from SEQ ID NOs: 52, 53, 55, 57, 58, 59, 60, 61, 62, and 63 (see table A-4 below). In one embodiment, the ISVD binding to human serum albumin has another position than the C-terminal position (i.e. is not the C-terminal ISVD of the polypeptide of the present disclosure) and is selected from SEQ ID NOs: 3, 50, 51, 54, and 56 (see table A-4 below).

5.4 Nucleic Acid Molecules

Also provided is a nucleic acid molecule encoding the polypeptide of the present disclosure. A "nucleic acid molecule" (used interchangeably with "nucleic acid") is a chain of nucleotide monomers linked to each other via a phosphate backbone to form a nucleotide sequence. A nucleic acid may be used to transform/transfect a host cell or host organism, e.g. for expression and/or production of a polypeptide. Suitable hosts or host cells for production purposes will be clear to the skilled person, and may for example be any suitable fungal, prokaryotic or eukaryotic cell or cell line or any suitable fungal, prokaryotic or eukaryotic organism. A host or host cell comprising a nucleic acid encoding the polypeptide of the present disclosure is also encompassed by the disclosure.

A nucleic acid may be for example DNA, RNA, or a hybrid thereof, and may also comprise (e.g. chemically) modified nucleotides, like PNA. It can be single- or double-stranded DNA. For example, the nucleotide sequences of the present disclosure may be genomic DNA, cDNA.

The nucleic acids of the present disclosure can be prepared or obtained in a manner known per se, and/or can be isolated from a suitable natural source. Nucleotide sequences encoding naturally occurring (poly)peptides can for example be subjected to site-directed mutagenesis, so as to provide a nucleic acid molecule encoding polypeptide with sequence variation. Also, as will be clear to the skilled person, to prepare a nucleic acid, also several nucleotide sequences, such as at least one nucleotide sequence encoding a targeting moiety and for example nucleic acids encoding one or more linkers can be linked together in a suitable manner.

Techniques for generating nucleic acids will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers.

5.5 Vectors

Also provided is a vector comprising the nucleic acid molecule encoding the polypeptide of the present disclosure. A vector as used herein is a vehicle suitable for carrying genetic material into a cell. A vector includes naked nucleic acids, such as plasmids or mRNAs, or nucleic acids embedded into a bigger structure, such as liposomes or viral vectors.

Vectors generally comprise at least one nucleic acid that is optionally linked to one or more regulatory elements, such as for example one or more suitable promoter(s), enhancer(s), terminator(s), etc.). The vector can is an expression vector, i.e. a vector suitable for expressing an encoded polypeptide or construct under suitable conditions, e.g. when the vector is introduced into a (e.g. human) cell. For DNA-based vectors, this usually includes the presence of elements for transcription (e.g. a promoter and a polyA signal) and translation (e.g. Kozak sequence).

In some embodiments, in the vector, said at least one nucleic acid and said regulatory elements are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

In some embodiments, any regulatory elements of the vector are such that they are capable of providing their intended biological function in the intended host cell or host organism.

For instance, a promoter, enhancer or terminator should be "operable" in the intended host cell or host organism, by which is meant that for example said promoter should be capable of initiating or otherwise controlling/regulating the transcription and/or the expression of a nucleotide sequence—e.g. a coding sequence—to which it is operably linked.

5.6 Compositions

The present disclosure also provides a composition comprising at least one polypeptide of the present disclosure, at least one nucleic acid molecule encoding a polypeptide of the present disclosure or at least one vector comprising such a nucleic acid molecule. The composition may be a pharmaceutical composition. The composition may further comprise at least one pharmaceutically acceptable carrier, diluent or excipient and/or adjuvant, and optionally comprise one or more further pharmaceutically active polypeptides and/or compounds.

5.7 Host Organisms

The disclosure also pertains to host cells or host organisms comprising the polypeptide of the present disclosure, the nucleic acid encoding the polypeptide of the present disclosure, and/or the vector comprising the nucleic acid molecule encoding the polypeptide of the present disclosure.

Suitable host cells or host organisms are clear to the skilled person, and are for example any suitable fungal, prokaryotic or eukaryotic cell or cell line or any suitable fungal, prokaryotic or eukaryotic organism. Specific examples include HEK293 cells, CHO cells, *Escherichia* col or *Pichia pastoris*. In some embodiments, the host is *Pichia pastoris*.

5.8 Methods and Uses of the Polypeptide

The disclosure also provides a method for producing the polypeptide of the present disclosure. The method may comprise transforming/transfecting a host cell or host organism with a nucleic acid encoding the polypeptide, expressing the polypeptide in the host, optionally followed by one or more isolation and/or purification steps. Specifically, the method may comprise:
a) expressing, in a suitable expression system (e.g., a suitable host cell or host organism or in another expression system), a nucleic acid sequence encoding the polypeptide; optionally followed by:
b) isolating and/or purifying the polypeptide.

Suitable host cells or host organisms for production purposes will be clear to the skilled person, and may for example be any suitable fungal, prokaryotic or eukaryotic cell or cell line or any suitable fungal, prokaryotic or eukaryotic organism. Specific examples include HEK293 cells, CHO cells, *Escherichia coli* or *Pichia pastoris*. In some embodiments, the host is *Pichia pastoris*.

The polypeptide of the present disclosure, a nucleic acid molecule or vector as described, or a composition comprising the polypeptide of the present disclosure, nucleic acid molecule or vector—such as the polypeptide or a composition comprising the same—are useful as a medicament.

Accordingly, the disclosure provides the polypeptide of the present disclosure, a nucleic acid molecule or vector as described, or a composition comprising the polypeptide of the present disclosure, nucleic acid molecule or vector for use as a medicament.

Also provided is the polypeptide of the present disclosure, a nucleic acid molecule or vector as described, or a composition comprising the polypeptide of the present disclosure, nucleic acid molecule or vector for use in the (prophylactic or therapeutic) treatment of an inflammatory and/or autoimmune disease.

Further provided is a (prophylactic and/or therapeutic) method of treating an inflammatory and/or autoimmune disease, wherein said method comprises administering, to a subject in need thereof, a pharmaceutically active amount of the polypeptide of the present disclosure, a nucleic acid molecule or vector as described, or a composition comprising the polypeptide of the present disclosure, nucleic acid molecule or vector.

Further provided is the use of the polypeptide of the present disclosure, a nucleic acid molecule or vector as described, or a composition comprising the polypeptide of the present disclosure, nucleic acid molecule or vector in the preparation of a pharmaceutical composition, such as a pharmaceutical composition for treating an inflammatory and/or autoimmune disease.

The inflammatory and/or autoimmune disease may for example be rheumatoid arthritis, Hidradenitis suppurativa and sarcoidosis. Preferably, the inflammatory and/or autoimmune disease is rheumatoid arthritis.

A "subject" as referred to in the context of the present disclosure can be any animal, such as a mammal. Among mammals, a distinction can be made between humans and non-human animals. Non-human animals may be for example companion animals (e.g. dogs, cats), livestock (e.g. bovine, equine, ovine, caprine, or porcine animals), or animals used generally for research purposes and/or for producing antibodies (e.g. mice, rats, rabbits, cats, dogs, goats, sheep, horses, pigs, non-human primates, such as cynomolgus monkeys, or camelids, such as llama or alpaca).

In the context of prophylactic and/or therapeutic purposes, the subject can be any animal, and more specifically any mammal, such as a human subject.

Substances (including polypeptides, nucleic acid molecules and vectors) or compositions may be administered to a subject by any suitable route of administration, for example by enteral (such as oral or rectal) or parenteral (such as epicutaneous, sublingual, buccal, nasal, intra-articular, intradermal, intramuscular, intraperitoneal, intravenous, subcutaneous, transdermal, or transmucosal) administration. Parenteral administration, such as intramuscular, subcutaneous or intradermal, administration can be used. In some embodiments, subcutaneous administration is used.

An effective amount of a polypeptide, a nucleic acid molecule or vector as described, or a composition comprising the polypeptide, nucleic acid molecule or vector can be administered to a subject in order to provide the intended treatment results.

One or more doses can be administered. If more than one dose is administered, the doses can be administered in suitable intervals in order to maximize the effect of the polypeptide, composition, nucleic acid molecule or vector.

TABLE A-0

F027201062 configuration

| Name | Building block 1 | Linker | Building block 2 | Linker | Building block 3 | Linker | Building block 4 |
|---|---|---|---|---|---|---|---|
| F027201062 | 17C04 | 9GS | ALB23002 | 9GS | 6B12 | 9GS | 6C11 + A* |

*C-terminal extension of a single alanine

TABLE A-1

Amino acid sequences of the different monovalent $V_{HH}$ building blocks identified within the tetravalent polypeptide F027201062 ("ID" refers to the SEQ ID NO as used herein)

| Name | ID | Amino acid sequence |
|---|---|---|
| 17C04 (anti-hIL-6) | 2 | DVQLVESGGGVVQPGGSLRLSCAASGRTFSNYAMAWFRQAPGKERE FVAVISYAGGRTYYADSVKGRFTISRDNAKNTVYLQMNSLRPEDTALY YCAAVDSPLIATHPRGYDYWGQGTLVTVSS |
| ALB23002 (anti-HSA) | 3 | EVQLVESGGGVVQPGGSLRLSCAASGFTFRSFGMSWVRQAPGKGPE WVSSISGSGSDTLYADSVKGRFTISRDNSKNTLYLQMNSLRPEDTALYY CTIGGSLSRSSQGTLVTVSS |
| 6B12 (anti-hIL-6) | 4 | EVQLVESGGGVVQPGGSLRLSCAASGFTLAYYAIGWFRQAPGKEREG VSCISGSVGTTYYADSVKGRFTISRDNAKNTVYLQMNSLRPEDTALYYC VRSSWFDCGVQGRDLGNEYDYRGQGTLVTVSS |
| 6C11 (anti-hTNF-α) | 5 | EVQLVESGGGVVQPGGSLRLSCTASGFTFSTADMGWFRQAPGKGRE FVARISGIDGTTYYDEPVKGRFTISRDNSKNTVYLQMNSLRPEDTALYY CRSPRYADQWSAYDYWGQGTLVKVSS |

TABLE A-2

Sequences for CDRs according to AbM numbering and frameworks ("ID" refers to the given SEQ ID NO)

| Building block | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 17C04 | 2 | DVQLVESGGGVVQ PGGSLRLSCAAS | 18 | GRTFS NYAMA | 6 | WFRQAPG KEREFVA | 21 | VISYA GGRTY | 10 | YADSVKGRFTISRD NAKNTVYLQMNSL RPEDTALYYCAA | 25 | VDSPLI ATHPRG YDY | 14 | WGQGTL VTVSS | 29 |
| ALB23002 | 3 | EVQLVESGGGVVQ PGGSLRLSCAAS | 19 | GFTFR SFGMS | | WVRQAPG KGPEWVS | 22 | SISGS GSDTL | 11 | YADSVKGRFTISRD NSKNTLYLQMNSLR PEDTALYYCTI | 25 | GGSLSR | 15 | SSQGTL VTVSS | 30 |
| 6B12 | 4 | EVQLVESGGGVVQ PGGSLRLSCAAS | 19 | GFTLA YYAIG | 8 | WFRQAPG KEREGVS | 23 | CISGS VGTTY | 12 | YADSVKGRFTISRD NAKNTVYLQMNSL RPEDTALYYCVR | 27 | SSWFDC GVQGRD LGNEYDY | 16 | RGQGTL VTVSS | 31 |
| 6C11 | 5 | EVQLVESGGGVVQ PGGSLRLSCTAS | 20 | GFTFS TADMG | 9 | WFRQAPG KGREFVA | 24 | RISGID GTTY | 13 | YDEPVKGRFTISRD NSKNTVYLQMNSL RPEDTALYYCRS | 28 | PRYADQ WSAYDY | 17 | WSQGTL VKVSS | 32 |

TABLE A-2

Sequences for CDRs according to Kabat numbering and frameworks ("ID" refers to the given SEQ ID NO)

| Building block | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 17C04 | 2 | DVQLVESGGGVV QPGGSLRLSCAAS GRTFS | 41 | NYAMA | 33 | WFRQAPG KEREFVA | 21 | VISYAGG RTYYADS VKG | 37 | RFTISRDNAKN TVYLQMNSLRP EDTALYYCAA | 45 | VDSPLIAT HPRGYDY | 14 | WGQGTL VTVSS | 29 |
| ALB23002 | 3 | EVQLVESGGGVVQ PGGSLRLSCAASGP TFR | 42 | SFGMS | 34 | WVRQAPG KGPEWVS | 22 | SISGSGS DTLYADS VKG | 38 | RFTISRDNSKN TLYLQMNSLRP EDTALYYCTI | 46 | GGSLSR | 15 | SSQGTL VTVSS | 30 |

TABLE A-2-continued

Sequences for CDRs according to Kabat numbering and frameworks
("ID" refers to the given SEQ ID NO)

| Building block | ID | FR1 | ID | CDR1 | ID | FB2 | ID | CDR2 | ID | FR3 | ID | CDR3 | ID | FR4 | ID |
|---|---|---|---|---|---|---|---|---|---|---|---|---|---|---|---|
| 6B12 | 4 | EVQLVESGGGVVQPGGSLRLSCAASGFTA | 43 | YYAIG | 35 | WFRQAPGKEREGVS | 23 | CISGSVGTTYYADSVKG | 39 | RFTISRDNAKNTVYLQMNSLRPEDTALYYCVR | 47 | SSWFDCGVQGRDLGNEYDY | 16 | RGQGTLVTVSS | 31 |
| 6C11 | 5 | EVQLVESGGGVVQPGGSLRLSCTASGFTFS | 44 | TADMG | 36 | WFRQAPGKGREFVA | 24 | RISGIDGTTYYDEPVKG | 40 | RFTISRDNSKNTVYLQMNSLRPEDTALYYCRS | 48 | PRYADQWSAYDY | 17 | WGQGTLVKVSS | 32 |

TABLE A-3

Amino acid sequences of selected multivalent polypeptide
("ID" refers to the given SEQ ID NO)

| Name | ID | Amino acid sequence |
|---|---|---|
| F027201062 | 1 | DVQLVESGGGVVQPGGSLRLSCAASGRTFSNYAMAWFRQAPGKEREFVAVISYAGGRTYYADSVKGRFTISRDNAKNTVYLGMNSLRPEDTALYYCAAVDSPLIATHPRGYDYWGQGTLVTVSSGGGGSGGGSEVQLVESGGGVVQPGGSLRLSCAASGFTFRSFGMSWVRQAPGKGPEWVSSISGSGSDTLYADSVKGRFTISRDNKNTLYLQMNSLRPEDTALYYCTIGGSLSRSSQGTLVTVSSGGGGSGGGSEVQLVESGGGVVQPGGSLRLSCAASGFTLAYYAIGWFRQAPGKEREGVSCISGSVGTTYYADSVKGRFTISRDNAKNTWYLQMNSLRPEDTALYYCVRSSWFDCGVQGRDLGNEYDYRGQGTLVTVSSGGGGSGGGSEVQLVESGGGWQPGGSLRLSCTASGFTFSTADMGWFRQAPGKGREFVARISGIDGTTYYDEPVKGRFTISRDNSKNTVYLOMNSLRPEDTALYYCRSPRYADQWSAYDYWGQGTLVKVSSA |

TABLE A-4

Serum albumin binding ISVD sequences
("ID" refers to the SEQ ID NO as used herein)

| Name | ID | Amino acid sequence |
|---|---|---|
| Alb8 | 50 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb23 | 51 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb129 | 52 | EVQLVESGGGVVQPGNSLRLSCAASGFTFSSFGMSWVRQAPGKGLEWVSSISGSGSDTLYADSVKGRFTISRDNAKTTLYLQMNSLRPEDTATYYCTIGGSLSRSSQGTLVTVSSA |
| Alb132 | 53 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSSA |
| Alb11 | 54 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb11 (S112K)-A | 55 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSSA |
| Alb82 | 56 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSS |
| Alb82-A | 57 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| Alb82-AA | 58 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAA |

TABLE A-4-continued

Serum albumin binding ISVD sequences
("ID" refers to the SEQ ID NO as used herein)

| Name | ID | Amino acid sequence |
|---|---|---|
| Alb-AAA | 59 | EVQLVESGGGVVQPGNSLRLSCAASGFTFSSFGMSWVRQAPGKGLEW VSSISGSGSDTLYADSVKGRFTISRDNAKTTLYLQMNSLRPEDTALYYCTIG GSLSRSSQGTLVTVSSAAA |
| Alb82-G | 60 | EVQLVESGGGVVQPGNSLRLSCAASGFTFSSFGMSWVRQAPGKGLEW VSSISGSGSDTLYADSVKGRFTISRDNAKTTLYLOMNSLRPEDTALYYCTIG GSLSRSSQGTLVTVSSG |
| Alb82-GG | 61 | EVQLVESGGGVVQPGNSLRLSCAASGFTFSSFGMSWVRQAPGKGLEW VSSISGSGSDTLYADSVKGRFTISRDNAKTTLYLOMNSLRPEDTALYYCTIG GSLSRSSQGTLVTVSSGG |
| Alb82-GGG | 62 | EVQLVESGGGVVQPGNSLRLSCAASGFTFSSFGMSWVRQAPGKGLEW VSSISGSGSDTLYADSVKGRFTISRDNAKTTLYLQMNSLRPEDTALYYCTIG GSLSRSSQGTLVTVSSGGG |
| Alb23002 | 3 | EVQLVESGGGVVQPGGSLRLSCAASGFTFRSFGMSWVRQAPGKGPEW VSSISGSGSDTLYADSVKGRFTISRDNSKNTLYLQMNSLRPEDTALYYCTIG GSLSRSSQGTLVTVSS |
| Alb223 | 63 | EVQLVESGGGVVQPGGSLRLSCAASGFTFRSFGMSWVRQAPGKGPEW VSSISGSGSDTLYADSVKGRFTISRDNSKNTLYLQMNSLRPEDTALYYCTIG GSLSRSSQGTLVTVSSA |

TABLE A-5

Linker sequences ("ID" refers to the SEQ ID NO as used herein)

| Name | ID | Amine acid sequence |
|---|---|---|
| 3A linker | 64 | AAA |
| 5GS linker | 65 | GGGGS |
| 7GS linker | 66 | SGGSGGS |
| 8GS linker | 67 | GGGGSGGS |
| 9GS linker | 68 | GGGGSGGGS |
| 10GS linker | 69 | GGGGSGGGGS |
| 15GS linker | 70 | GGGGSGGGGSGGGGS |
| 18GS linker | 71 | GGGGSGGGGSGGGGSGGS |
| 20GS linker | 72 | GGGGSGGGGSGGGGSGGGGS |
| 25GS linker | 73 | GGGGSGGGGSGGGGSGGGGSGGGGS |
| 30GS linker | 74 | GGGGSGGGGSGGGGSGGGGSGGGGSGGGGS |
| 35GS linker | 75 | GGGGSGGGGSGGGGSGGGGSGGGGSGGGGSGGGGS |
| 40GS linker | 76 | GGGGSGGGGSGGGGSGGGGSGGGGSGGGGSGGGGSGGGGS |
| G1 hinge | 77 | EPKSCDKTHTCPPCP |
| 9GS-G1 binge | 78 | GGGGSGGGSEPKSCDKTHTCPPCP |
| Llama upper long hinge region | 79 | EPKTPKPQPAAA |
| G3 hinge | 80 | ELKTPLGDTTHTCPRCPEPKSCDTPPPCPRCPEPK SCDTPPPCPRCPEPKSCDTPPPCPRCP |

6 EXAMPLES

6.1 Example 1: Generation and in Vitro Characterization of Wild-Type Anti-IL6 Bivalent or Biparatopic ISVD Constructs Monovalent anti-IL-6 ISVDs IL6006B06, IL006812, IL6007G04, IL6007G05, IL6007G09, IL6010A06, IL6013F12 and IL6017C04 (described in WO2007104529) did not show sufficient IL-6 blocking capacity when examined in the TF-1 proliferation assay, compared to anti-IL-6 reference mAb 1 (benchmark monoclonal antibody directed against IL-6). In an attempt to improve on potency, the anti-IL-6 ISVDs were formatted into biparatopic ISVD constructs. The building blocks in the constructs are genetically linked by a flexible 35GS or 9GS (GlySer) linker. ISVDs were expressed as FLAG3-HIS6-tagged protein in *E. coli*. Expression was performed via auto-induction and allowed to continue for ON at 30° C. After spinning the cell cultures, periplasmic extracts were prepared by freeze-thawing the pellets and resuspension in dPBS. These extracts were used as starting material for immobilized metal affinity chromatography (IMAC) using Nickel IDA/NTA columns (Genscript—Atoll). ISVDs were eluted from the column with 200 mM Na-acetate pH4, neutralized with TrisHCl pH8 and subsequently desalted towards dPBS.

The inhibitory potency of the anti-IL-6 ISVDs was determined in a cell-based assay monitoring IL-6 mediated proliferation of TF-1 cells. To this end, TF-1 cells were cultured in RPMI 1640, glutamax, HEPES medium (Gibco) supplemented with 10% FBS and 1% Na-Pyruvate. TF-1 cells were seeded at 12.500 cells per well in growth medium. A dilution series of the purified anti-IL-6 ISVDs or reference compounds was added. After 30 min incubation at 37° C., 75 pM of human IL-6 (R&D systems cat nr 200-IL-2001206-IL) was added. After 72 hours, proliferation of the TF-1 cells was determined with CellTiter-Glo (Promega #G7571) on an EnVision Multilabel Reader (Perkin Elmer).

Several biparatopic constructs displayed improved potencies against human IL-6 and reached potencies similar to the potency of anti-hIL-6 reference mAb 1 (Table 1).

In addition, bivalent anti-IL-6 ISVDs, genetically linked by a flexible 35GS (GlySer) linker were generated and their potency was evaluated in a second cell-based assay, monitoring IL-6 induced pSTAT3 generation in THP-1 cells. To this end THP-1 cells were cultured in RPMI1640 medium supplemented with Glutamax+ and 10% heat-Inactivated FBS. Before seeding into a white 96 well plate, the medium was exchanged to HBSS, cells were seeded at a density of 100.000 cells/well. A dilution series of purified anti-IL-6 ISVDs or reference anti-IL-6 mAb1 was added together with 300 pM hIL-6 (R&D systems cat nr 200-IL-200|206-IL) and incubated or 20 minutes at 37° C. Subsequently, cells were spun down and lysed. 16 μl of the lysed cell supernatant was mixed with a HTRF detection antibody mix for pSTAT3 and total STAT3 (PHOSPHO-STAT3 (TYR705) KIT, Cisbio #62AT3PE). Using this kit pSTAT3 (Tyr705) is detected in a sandwich assay format using 2 different specific antibodies, one labelled with Eu3+-Cryptate (donor) and the second with d2 (acceptor). When the dyes are in close proximity, the excitation of the donor with a light source triggers a Fluorescence Resonance Energy Transfer (FRET) towards the acceptor, which in turn fluoresces at a specific wavelength (665 nm). The specific signal modulates positively in proportion to pSTAT3. pSTAT was quantified with on an EnVision Multilabel Reader (Perkin Elmer) by measuring absorption at 665 nm and total STAT3 by measuring absorption at 620 nm.

While the bivalent constructs did not significantly increase in potency compared to the monovalent anti-IL-6 ISDVs, the biparotopic anti-IL-6 ISVDs showed a significant potency increase compared to monovalent or bivalent constructs (Table 2).

From this exercise, 11 biparatopic anti-IL-6 ISVDs were selected to be coupled to anti-TNF-α ISVDs: IL6013F12-IL6006B06, 116006806-IL6017C04, IL6013F12-IL6007G09, IL6006B06-IL6006B12, IL6006B06-IL6010A06, IL6017C04-IL6007G09, IL6006812-IL6013F12, IL6010A06-IL6007G09, IL6006812-IL007G09, IL6007G09-IL6006812 or IL6017C04-IL6006B12.

TABLE 1

Fold difference in IC50 of monovalent and biparatopic anti-IL-6 ISVDs compared to reference anti-IL-6 mAb 1 in the TF1 proliferation assay.

| ISVD ID | BB1 | linker | BB2 | Ratio IC50 anti IL-6 ISVD/IC50 reference anti-IL-6 mAb1 |
|---|---|---|---|---|
| A007100001 | 10A06 | | | 2909 |
| A007100002 | 13F12 | | | 70 |
| A007100003 | 17C04 | | | 107 |
| A007100005 | 6B12 | | | 77 |
| A007100008 | 7G09 | | | 1489 |
| A007100009 | 6B06 | | | 7 |
| F027200055 | 7G04 | 35GS | 13F12 | 5-7 |
| F027200062 | 6B12 | 35GS | 6B06 | 5-9 |
| F027200064 | 17C04 | 35GS | 7G09 | 1-3 |
| F027200066 | 10A06 | 35GS | 6B12 | 2 |
| F027200067 | 13F12 | 35GS | 6B06 | 1-3 |
| F027200069 | 10A06 | 35GS | 6B06 | 2-4 |
| F027200070 | 13F12 | 35GS | 6B12 | 1-2 |
| F027200071 | 17C04 | 35GS | 6B12 | 2 |
| F027200072 | 6B12 | 35GS | 17C04 | 2 |
| F027200073 | 6B12 | 35GS | 13F12 | 2 |

TABLE 1-continued

Fold difference in IC50 of monovalent and biparatopic anti-IL-6 ISVDs compared to reference anti-IL-6 mAb 1 in the TF1 proliferation assay.

| ISVD ID | BB1 | linker | BB2 | Ratio IC50 anti IL-6 ISVD/IC50 reference anti-IL-6 mAb1 |
|---|---|---|---|---|
| F027200075 | 10A06 | 35GS | 7G09 | 2 |
| F027200076 | 13F12 | 35GS | 7G09 | 5 |
| F027200077 | 13F12 | 35GS | 7G05 | 6-7 |
| F027200078 | 17C04 | 35GS | 6B06 | 1-2 |
| F027200079 | 17C04 | 35GS | 7G05 | 4-9 |
| F027200080 | 6B06 | 35GS | 13F12 | 2-3 |
| F027200081 | 6B06 | 35GS | 6B12 | 4-6 |
| F027200082 | 7G05 | 35GS | 17C04 | 4-7 |
| F027200084 | 7G09 | 35GS | 6B12 | 2 |
| F027200085 | 6B06 | 35GS | 17C04 | 3-8 |
| F027200113 | 6B06 | 9GS | 10A06 | 2-3 |

BB = building block

TABLE 2

Fold difference in IC50 of monovalent, bivalent and biparatopic anti-IL-6 ISVDs compared to reference anti-IL-6 mAb 1 in the THP1 pSTAT3 assay.

| ISVD ID | BB1 | linker | BB2 | Ratio IC50 anti-IL-6 ISVD/IC50 reference anti-IL-6 mAb1 |
|---|---|---|---|---|
| A007100001 | 10A06 | | | 27 |
| A007100002 | 13F12 | | | 86 |
| A007100003 | 17C04 | | | 14 |
| A007100005 | 6B12 | | | 14 |
| A007100008 | 7G09 | | | 8 |
| A007100009 | 6B06 | | | 22 |
| F027200029 | 13F12 | 35GS | 13F12 | 49 |
| F027200030 | 17C04 | 35GS | 17C04 | 14 |
| F027200031 | 6B06 | 35GS | 6B06 | 25 |
| F027200032 | 6B12 | 35GS | 6B12 | 46 |
| F027200035 | 7G09 | 35GS | 7G09 | 6 |
| F027200036 | 10A06 | 35GS | 10A06 | 13 |
| F027200062 | 6B12 | 35GS | 6B06 | 4 |
| F027200064 | 17C04 | 35GS | 7G09 | 2 |
| F027200064 | 17C04 | 35GS | 7G09 | 2 |
| F027200067 | 13F12 | 35GS | 6B06 | 7 |
| F027200069 | 10A06 | 35GS | 6B06 | 3 |
| F027200073 | 6B12 | 35GS | 13F12 | 6 |
| F027200082 | 7G05 | 35GS | 17C04 | 4 |
| F027200084 | 7G09 | 35GS | 6B12 | 1 |
| F027200089 | 7G09 | 35GS | 13F12 | 6 |

BB = building block

6.2 Example 2: Sequence Optimization of Anti-IL-6 Monovalent ISVDs

Anti-IL-6 ISVDs IL6006812 and IL6017C04 were further sequence optimized. Sequence optimization involves replacing one or more specific amino acid residues in the sequence in order to improve one or more (desired) properties of the ISVDs.

Some examples of such sequence optimization are mentioned in the further description herein and for example include, without limitation:

Substitutions in parental wild type Nanobody® sequences to yield Nanobody® sequences that are more identical to the human $V_H3$-JH germline consensus sequences, a process called humanization. To this end, specific amino acids, with the exception of the so-called hallmark residues, in the FRs that differ between the Nanobody® and the human VH3-JH germline consensus are altered to the human counterpart in such a way that the protein structure, activity and stability are kept intact.

Substitutions towards the llama germline to increase the stability of the ISVD, which is defined as camelisation. To this end, the parental wild type Nanobody® amino acid sequence is aligned to the llama IGHV germline amino acid sequence of the Nanobody® (identified as the top hit from a BlastP analysis of the Nanobody® against the llama IGHV germlines).

Substitutions that improve long-term stability or properties under storage, substitutions that increase expression levels in a desired host cell or host organism, and/or substitutions that remove or reduce (undesired) post-translational modification(s) (such as glycosylation or phosphorylation), again depending on the desired host cell or host organism. To avoid N-terminal pyroglutamate formation, standardly an E1D mutation is introduced in the N-terminal building block of a multivalent Nanobody, without impact on potency or stability. During sequence optimization of the building blocks, the E1D mutation is therefore not consistently introduced.

Mutations on position 11 towards Val and on position 89 towards Leu to minimize the binding of any naturally occurring pre-existing antibody activity.

Sequence optimisation of anti-IL-6 ISVD IL6006B12 resulted in a final sequence optimised variant F027201040, which comprises 5 amino acid substitutions (i.e. L11V, S52aG, S60A, K83R, V89L) compared to the parental ISVD IL6006B12. Sequence optimisation of anti-IL-6 ISVD I16017C04 resulted in a final sequence optimised variant F027200921, which comprises 6 amino acid substitutions (i.e. E1D, L11V, A14P, D16G, K83R, V89L) compared to the parental ISVD IL6017C04.

The sequence optimised variants were assembled from oligonucleotides using a PCR overlap extension method. The variants were expressed in *E. coli* and purified by IMAC and desalting. F027201040 was evaluated for its hIL-6 binding capacity by surface plasmon resonance, F027200921 for its neutralizing activity in the TF1 proliferation assay. Monomeric behavior of both variants was monitored by Size Exclusion-HPLC (SE-HPLC). Thermal stability of the variants was tested in a thermal shift assay (TSA) using the Lightcycler (Roche). In this assay, the parental ISVDs and their variants are incubated at different pH's in the presence of spyro orange and a temperature gradient is applied. When the ISVDs start denaturing, spyro orange binds and the measured fluorescence increases suddenly, as such a melting temperature can be determined for a certain pH. Results are summarized in Table 3 and Table 4.

TABLE 3 results of the analysis of the sequence optimization variant F027201040 of anti-IL-6 ISVD IL6006B12

| ISVD ID | Mutation(s) | $k_{off}$ hIL-6 (1/s) | Tm (° C.) at pH 7 TSA | SE-HPLC % main peak |
| --- | --- | --- | --- | --- |
| IL6006B12 | — | 6.5E−05 | 72 | 100 |
| F027201040 | L11V, S52aG, S60A, K83R, V89L | 5.9E−05 | 79 | 100 |

F027201040 showed a similar off-rate for binding to IL-6 in SPR compared to the parental ISVD IL006B12. The Tm of F027201040 is 7° C. higher than for the parental ISVD IL006B12. The % framework identity in the framework regions for F027201040 is 88% based on the AbM definition (see Antibody Engineering, Vol2 by Kontermann & Dubel (Eds), Springer Verlag Heidelberg Berlin, 2010) and 86% based on the Kabat definition.

TABLE 4

Results of the analysis of the sequence optimization variant of anti-IL-6 ISVD IL6017C04

| ISVD ID | Mutation(s) | TF-1 proliferation assay hIL-6 IC50 (M) | Tm (° C.) at pH 7 TSA | SE-HPLC % main peak |
| --- | --- | --- | --- | --- |
| IL6017C04 | — | 3.8E−08 | 85 | 99 |
| F027200921 | E1D, L11V, A14P, D16G, K83R, V89L | 5.5E−08 | 84 | 95 |

Potency of F027200921 in the TF1 proliferation assay is similar compared to the WT sequence. The Tm of F027200921 is 1° C. lower than for the parental ISVD F027200921. The % framework identity in the framework regions for F027200921 Is 88% based on the AbM definition and 86% based on the Kabat definition.

TABLE 5

Amino acid sequences of sequence optimized version of ISVD's IL6006B12 and IL017C04

| ISVD ID | ISVD description | Sequence |
| --- | --- | --- |
| F027200921 | IL6017C04 (E1D, L11V, A14P, D16G, K83R, V89L) | DVQLVESGGGVQPGGSLRLSCAASGR TFSNYAMAWFRQAPGKEREFVAVIS YAGGRTYYADSVKGRFTISRDNAKNT VYLOMNSLRPEDTALYYCAAVDSPLI ATHPRGYDYWGQGTLVTVSS |
| F027201040 | IL6006812 (L11V, S52aG, S60A, K83R, V89L) | EVQLVESGGGWVOPGGSLRLSCAASG FTLAYYAIGWFRQAPGKEREGVSCIS GSVGTTYYADSVKGRFTISRONAKNT VYLOMNSLRPEDTALYYCVRSSWFDC GVQGRDLGNEYDYRGQGTLVTVSS |

6.3 Example 3: Multispecific ISVD Construct Generation

Identification of ISVD-containing polypeptide F027201062 (SEQ ID NO: 1) binding to TNFα and IL-6 resulted from a data-driven multispecific engineering and formatting campaign in which three anti-TNFα VHH building blocks (TNF06C11 (WO2017081320), TNF01C02 (WO2015173325, SEQ ID NO: 327) and VHH #3 (WO2004041862)), and six anti-IL-6 VHH building blocks (IL6006806, IL006812, IL6007G04, 1L6007G05, IL6007G09, IL6010A06, IL6013F12 and IL6017C04, WO2007104529) and the anti-HSA VHH building block ALB23002 (see WO2017134234, SEQ ID NO:10/ WO2018131234) were included. Different positions/orientations of the building blocks were applied and proved to be critical for different parameters (potency, cross-reactivity, expression, etc.). The linker between the building blocks was kept to 9GS for all constructs, to minimize as much as possible binding of pre-existing antibodies.

A panel comprising 87 constructs (Table 6) was transformed in *Pichia pastoris* for small scale productions. Induction of ISVD expression occurred by stepwise addition of methanol. Clarified medium with secreted ISVD was used as starting material for purification via Protein A affinity chromatography followed by desalting. The purified samples were used for expression evaluation and functional characterisation. For the latter potency was determined by assaying inhibition of TNFα-induced NFκB activation and inhibition of IL-6 induced proliferation of TF-1 cells in vitro (as described in Examples 8 and 9).

In addition, the ISVD expression levels were monitored in the clarified medium. Constructs were classified according to the following expression level criteria:low=<50 μg/ml, medium=51-100 μg/ml, high=>101 μg/ml (Table 6).

TABLE 6

Listing of the 87 different multispecific ISVD formats evaluated, with their respective expression level, IC50 in the Nfkb-reporter assay, IC50 in the TF1 proliferation assay and the difference in potencies between human and cyno TNF-alpha and IL-6 respectively.

| ISVD construct ID | Anti-IL-6 biparatopic ISDV in construct | BB1 | linker 1 | BB2 | linker 2 | BB3 | linker 3 | BB4 |
|---|---|---|---|---|---|---|---|---|
| F027200926 | 10A06-7G09 | 1C02 | 9GS | 10A06 | 9GS | ALB | 9GS | 7G09 |
| F027200927 | 10A06-7G09 | 6C11 | 9GS | 10A06 | 9GS | ALB | 9GS | 7G09 |
| F027200928 | 10A06-7G09 | 10A06 | 9GS | ALB | 9GS | 7G09 | 9GS | 1C02 |
| F027200929 | 10A06-7G09 | 10A06 | 9GS | ALB | 9GS | 7G09 | 9GS | 6C11 |
| F027200930 | 10A06-7G09 | 10A06 | 9GS | 1C02 | 9GS | 7G09 | 9GS | 1C02 |
| F027200158 | 13F12-6B06 | 1C02 | 9GS | ALB | 9GS | 13F12 | 9GS | 6B06 |
| F027200159 | 13F12-6B06 | 6C11 | 9GS | ALB | 9GS | 13F12 | 9GS | 6B06 |
| F027200162 | 13F12-6B06 | 13F12 | 9GS | 6B06 | 9GS | ALB | 9GS | 1C02 |
| F027200163 | 13F12-6B06 | 13F12 | 9GS | 6B06 | 9GS | ALB | 9GS | 6C11 |
| F027200178 | 13F12-6B06 | 13F12 | 9GS | 6B06 | 9GS | 1C02 | 9GS | ALB |
| F027200181 | 13F12-6B06 | 13F12 | 9GS | 6B06 | 9GS | VHH#3E | 9GS | ALB |
| F027200202 | 13F12-6B06 | 1C02 | 9GS | ALB | 9GS | 1C02 | 9GS | 13F12 |
| F027200205 | 13F12-6B06 | VHH#3E | 9GS | ALB | 9GS | VHH#3E | 9GS | 13F12 |
| F027200160 | 13F12-7G09 | 6C11 | 9GS | ALB | 9GS | 13F12 | 9GS | 7G09 |
| F027200161 | 13F12-7G09 | 1C02 | 9GS | ALB | 9GS | 13F12 | 9GS | 7G09 |
| F027200191 | 13F12-7G09 | 1C02 | 9GS | ALB | 9GS | 1C02 | 9GS | 13F12 |
| F027200195 | 13F12-7G09 | VHH#3E | 9GS | ALB | 9GS | VHH#3E | 9GS | 13F12 |
| F027200208 | 13F12-7G09 | 13F12 | 9GS | 7G09 | 9GS | 1C02 | 9GS | ALB |
| F027200209 | 13F12-7G09 | 13F12 | 9GS | 7G09 | 9GS | VHH#3E | 9GS | ALB |
| F027200214 | 13F12-7G09 | 13F12 | 9GS | 7G09 | 9GS | ALB | 9GS | 6C11 |
| F027200771 | 13F12-7G09 | 13F12 | 9GS | 7G09 | 9GS | ALB | 9GS | 1C02 |
| F027201024 | 17C04-6B06 | 17C04 | 9GS | 6B06 | 9GS | 1C02 | 9GS | ALB |
| F027201025 | 17C04-6B06 | 1C02 | 9GS | ALB | 9GS | 1C02 | 9GS | 17C04 |
| F027201026 | 17C04-6B06 | 6C11 | 9GS | ALB | 9GS | 17C04 | 9GS | 6B06 |
| F027201027 | 17C04-6B06 | 17C04 | 9GS | ALB | 9GS | 6B06 | 9GS | 6C11 |
| F027201028 | 17C04-6B06 | 17C04 | 9GS | 6B06 | 9GS | ALB | 9GS | 6C11 |
| F027201029 | 17C04-6B06 | 6C11 | 9GS | 17C04 | 9GS | ALB | 9GS | 6B06 |
| F027201030 | 17C04-6B06 | 17C04 | 9GS | 1C02 | 9GS | 6B06 | 9GS | 1C02 |
| F027201031 | 17C04-6B06 | 1C02 | 9GS | 17C04 | 9GS | 1C02 | 9GS | 6B06 |
| F027201058 | 17C04-6B12 | 17C04 | 9GS | 1C02 | 9GS | 6B12 | 9GS | 1C02 |
| F027201059 | 17C04-6B12 | 1C02 | 9GS | 17C04 | 9GS | 1C02 | 9GS | 6B12 |
| F027201062 | 17C04-6B12 | 17C04 | 9GS | ALB | 9GS | 6B12 | 9GS | 6C11 |
| F027200204 | 17C04-7G09 | VHH#3E | 9GS | 17C04 | 9GS | VHH#3E | 9GS | 7G09 |
| F027200212 | 17C04-7G09 | 17C04 | 9GS | VHH#3E | 9GS | 7G09 | 9GS | VHH#3E |
| F027200216 | 17C04-7G09 | 17C04 | 9GS | ALB | 9GS | 7G09 | 9GS | 1C02 |
| F027200809 | 17C04-7G09 | 6C11 | 9GS | 17C04 | 9GS | ALB | 9GS | 7G09 |
| F027200812 | 17C04-7G09 | 17C04 | 9GS | ALB | 9GS | 7G09 | 9GS | 6C11 |
| F027200817 | 17C04-7G09 | 1C02 | 9GS | 17C04 | 9GS | 1C02 | 9GS | 7G09 |
| F027200818 | 17C04-7G09 | 17C04 | 9GS | 1C02 | 9GS | 7G09 | 9GS | 1C02 |
| F027200823 | 17C04-7G09 | 1C02 | 9GS | 17C04 | 9GS | ALB | 9GS | 7G09 |
| F027200153 | 6B06-10A06 | 6C11 | 9GS | ALB | 9GS | 6B06 | 9GS | 10A06 |
| F027200165 | 6B06-10A06 | 6B06 | 9GS | 10A06 | 9GS | ALB | 9GS | 1C02 |
| F027200167 | 6B06-10A06 | 6B06 | 9GS | 10A06 | 9GS | ALB | 9GS | 6C11 |
| F027200168 | 6B06-10A06 | 6B06 | 9GS | ALB | 9GS | 10A06 | 9GS | 6C11 |
| F027200169 | 6B06-10A06 | 6B06 | 9GS | ALB | 9GS | 10A06 | 9GS | 1C02 |
| F027200179 | 6B06-10A06 | 6B06 | 9GS | 10A06 | 9GS | 1C02 | 9GS | ALB |
| F027200183 | 6B06-10A06 | 6B06 | 9GS | 1C02 | 9GS | 10A06 | 9GS | 1C02 |
| F027200185 | 6B06-10A06 | 6B06 | 9GS | VHH#3E | 9GS | 10A06 | 9GS | VHH#3E |
| F027200192 | 6B06-10A06 | VHH#3E | 9GS | ALB | 9GS | VHH#3E | 9GS | 6B06 |
| F027200196 | 6B06-10A06 | VHH#3E | 9GS | 6B06 | 9GS | VHH#3E | 9GS | 10A06 |
| F027200201 | 6B06-10A06 | 1C02 | 9GS | ALB | 9GS | 1C02 | 9GS | 6B06 |
| F027200218 | 6B06-10A06 | 1C02 | 9GS | 6B06 | 9GS | 1C02 | 9GS | 10A06 |
| F027200219 | 6B06-10A06 | 6B06 | 9GS | 10A06 | 9GS | VHH#3E | 9GS | ALB |
| F027200782 | 6B06-10A06 | 1C02 | 9GS | 6B06 | 9GS | ALB | 9GS | 10A06 |
| F027200925 | 6B06-10A06 | 6C11 | 9GS | 6B06 | 9GS | ALB | 9GS | 10A06 |
| F027200154 | 6B06-17C04 | 6C11 | 9GS | ALB | 9GS | 6B06 | 9GS | 17C04 |
| F027200155 | 6B06-17C04 | 1C02 | 9GS | ALB | 9GS | 6B06 | 9GS | 17C04 |
| F027200187 | 6B06-17C04 | 6B06 | 9GS | 17C04 | 9GS | 1C02 | 9GS | ALB |
| F027200189 | 6B06-17C04 | 1C02 | 9GS | ALB | 9GS | 1C02 | 9GS | 6B06 |
| F027200193 | 6B06-17C04 | VHH#3E | 9GS | ALB | 9GS | VHH#3E | 9GS | 6B06 |
| F027200210 | 6B06-17C04 | 6B06 | 9GS | 17C04 | 9GS | VHH#3E | 9GS | ALB |
| F027200213 | 6B06-17C04 | 6B06 | 9GS | 17C04 | 9GS | ALB | 9GS | 1C02 |
| F027200215 | 6B06-17C04 | 6B06 | 9GS | 17C04 | 9GS | ALB | 9GS | 6C11 |

TABLE 6-continued

Listing of the 87 different multispecific ISVD formats evaluated, with their respective expression level, IC50 in the Nfkb-reporter assay, IC50 in the TF1 proliferation assay and the difference in potencies between human and cyno TNF-alpha and IL-6 respectively.

| | | | | | | | | |
|---|---|---|---|---|---|---|---|---|
| F027200156 | 6B06-6B12 | 1C02 | 9GS | ALB | 9GS | 6B06 | 9GS | 6B12 |
| F027200157 | 6B06-6B12 | 6C11 | 9GS | ALB | 9GS | 6B06 | 9GS | 6B12 |
| F027200164 | 6B06-6B12 | 6B06 | 9GS | 6B12 | 9GS | ALB | 9GS | 1C02 |
| F027200166 | 6B06-6B12 | 6B06 | 9GS | 6B12 | 9GS | ALB | 9GS | 6C11 |
| F027200180 | 6B06-6B12 | 6B06 | 9GS | 6B12 | 9GS | 1C02 | 9GS | ALB |
| F027200188 | 6B06-6B12 | 6B06 | 9GS | 6B12 | 9GS | VHH#3E | 9GS | ALB |
| F027200190 | 6B06-6B12 | 1C02 | 9GS | ALB | 9GS | 1C02 | 9GS | 6B06 |
| F027200194 | 6B06-6B12 | VHH#3E | 9GS | ALB | 9GS | VHH#3E | 9GS | 6B06 |
| F027200170 | 6B12-13F12 | 6B12 | 9GS | ALB | 9GS | 13F12 | 9GS | 6C11 |
| F027200171 | 6B12-13F12 | 6B12 | 9GS | ALB | 9GS | 13F12 | 9GS | 1C02 |
| F027200172 | 6B12-13F12 | 6C11 | 9GS | 6B12 | 9GS | ALB | 9GS | 13F12 |
| F027200173 | 6B12-13F12 | 1C02 | 9GS | 6B12 | 9GS | ALB | 9GS | 13F12 |
| F027200184 | 6B12-13F12 | 6B12 | 9GS | 1C02 | 9GS | 13F12 | 9GS | 1C02 |
| F027200186 | 6B12-13F12 | 6B12 | 9GS | VHH#3E | 9GS | 13F12 | 9GS | VHH#3E |
| F027200197 | 6B12-13F12 | VHH#3E | 9GS | 6B12 | 9GS | VHH#3E | 9GS | 13F12 |
| F027200198 | 6B12-13F12 | 1C02 | 9GS | 6B12 | 9GS | 1C02 | 9GS | 13F12 |
| F027201056 | 6B12-7G09 | 1C02 | 9GS | 6B12 | 9GS | 1C02 | 9GS | 7G09 |
| F027201057 | 6B12-7G09 | 6B12 | 9GS | 1C02 | 9GS | 7G09 | 9GS | 1C02 |
| F027201060 | 6B12-7G09 | 6B12 | 9GS | ALB | 9GS | 7G09 | 9GS | 6C11 |
| F027201061 | 6B12-7G09 | 6C11 | 9GS | 6B12 | 9GS | ALB | 9GS | 7G09 |
| F027200981 | 7G09-6B12 | 1C02 | 9GS | 7G09 | 9GS | 1C02 | 9GS | 6B12 |
| F027200983 | 7G09-6B12 | 7G09 | 9GS | 1C02 | 9GS | 6B12 | 9GS | 1C02 |
| F027200987 | 7G09-6B12 | 7G09 | 9GS | ALB | 9GS | 6B12 | 9GS | 6C11 |
| F027200989 | 7G09-6B12 | 6C11 | 9GS | 7G09 | 9GS | ALB | 9GS | 6B12 |

| ISVD construct ID | linker 4 | BB5 | expression level | hTNF-α Nfkb assay (IC50, M) | Ratio IC50 cyno TNFα/ hTNFα | hIL-6 TF1 proliferation assay (IC50, M) | IC50 cyno IL-6/hIL-6 |
|---|---|---|---|---|---|---|---|
| F027200926 | | | high | 4.53E−10 | 5.9 | 5.86E−11 | 1.2 |
| F027200927 | | | high | 5.93E−11 | 4.3 | 7.12E−11 | 1.0 |
| F027200928 | | | high | 7.88E−10 | 4.2 | 6.89E−11 | 1.0 |
| F027200929 | | | high | 8.58E−11 | 3.2 | 7.38E−11 | 1.0 |
| F027200930 | 9GS | ALB | medium | 2.98E−11 | 3.4 | 7.23E−11 | 1.0 |
| F027200158 | | | high | 1.02E−09 | 3.3 | | |
| F027200159 | | | medium | 1.30E−10 | 3.9 | 3.73E−10 | 2.4 |
| F027200152 | | | medium | 1.04E−09 | 4.0 | 2.87E−10 | 2.5 |
| F027200163 | | | low | 1.31E−10 | 3.6 | 3.02E−10 | 2.4 |
| F027200178 | 9GS | 1C02 | medium | 7.8E−11 | 2.1 | 4.37E−10 | 2.2 |
| F027200181 | 9GS | VHH#3E | low | 7.01E−11 | 3.6 | 3.14E−10 | 1.9 |
| F027200202 | 9GS | 6B06 | medium | 8.55E−11 | 3.2 | 5.52E−10 | 2.7 |
| F027200205 | 9GS | 6B06 | medium | 8.75E−11 | 4.6 | 9.43E−10 | 2.9 |
| F027200160 | | | high | 1.21E−10 | 3.2 | 3.41E−10 | 0.9 |
| F027200161 | | | high | 6.34E−10 | 3.7 | 2.68E−10 | 0.8 |
| F027200191 | 9GS | 7G09 | medium | 5.47E−11 | 3.4 | 3.05E−10 | 1.0 |
| F027200195 | 9GS | 7G09 | low | 6.46E−11 | 4.1 | 3.30E−10 | 1.0 |
| F027200208 | 9GS | 1C02 | medium | 8.02E−11 | 3.4 | 3.80E−10 | 1 |
| F027200209 | 9GS | VHH#3E | low | 7.24E−11 | 5.5 | 3.19E−10 | 1 |
| F027200214 | | | medium | 2.02E−10 | 2.6 | 3.68E−10 | 1 |
| F027200771 | | | high | 7.88E−10 | 7.2 | 3.57E−10 | 0.7 |
| F027201024 | 9GS | 1C02 | high | 1.71E−11 | 3.8 | 2.86E−10 | 1.3 |
| F027201025 | 9GS | 6B06 | high | 1.64E−11 | 4.5 | 2.85E−10 | 1.3 |
| F027201026 | | | medium | 8.52E−11 | 2.2 | 3.03E−10 | 1.2 |
| F027201027 | | | medium | 6.03E−11 | 2.5 | 3.17E−10 | 0.6 |
| F027201028 | | | low | 6.10E−11 | 3.1 | 2.93E−10 | 1.1 |
| F027201029 | | | medium | 6.85E−11 | 2.0 | 3.47E−10 | 0.6 |
| F027201030 | 9GS | ALB | medium | 1.91E−11 | 4.2 | 3.08E−10 | 0.6 |
| F027201031 | 9GS | ALB | medium | 2.08E−11 | 3.3 | 3.08E−10 | 0.9 |
| F027201058 | 9GS | ALB | high | 4.029E−11 | 2.3 | 1.55E−10 | 0.6 |
| F027201059 | 9GS | ALB | medium | 4.155E−11 | 2.2 | 1.35E−10 | 0.7 |
| F027201062 | | | medium | 9.784E−11 | 2.0 | 1.34E−10 | 0.5 |
| F027200204 | 9GS | ALB | medium | 6.37E−11 | 5.9 | 7.71E−11 | 0.7 |
| F027200212 | 9GS | ALB | low | 8.10E−11 | 5.5 | 8.21E−11 | 1 |
| F027200216 | | | medium | 1.44E−09 | 6.9 | 8.90E−11 | 1 |
| F027200809 | | | high | 1.41E−10 | 2.3 | 6.82E−11 | 0.9 |
| F027200812 | | | medium | 2.06E−10 | 1.7 | 7.2E−11 | 0.7 |
| F027200817 | 9GS | ALB | high | 6.80E−11 | 1.6 | 6.44E−11 | 1.1 |
| F027200818 | 9GS | ALB | high | 8.91E−11 | 2.1 | 8.29E−11 | 0.9 |
| F027200823 | | | high | 1.55E−09 | 4.5 | 7.81E−11 | 0.8 |
| F027200153 | | | high | 1.39E−10 | 2.7 | 1.03E−09 | 2.5 |
| F027200165 | | | medium | 9.94E−10 | 5.2 | 5.98E−10 | 3.9 |
| F027200167 | | | medium | 1.71E−10 | 3.1 | 1.27E−09 | 2.5 |
| F027200168 | | | medium | 1.40E−10 | 3.3 | 9.66E−10 | 1.6 |
| F027200169 | | | medium | 1.18E−09 | 3.7 | 3.82E−10 | 2.1 |

TABLE 6-continued

Listing of the 87 different multispecific ISVD formats evaluated, with their respective expression level, IC50 in the Nfkb-reporter assay, IC50 in the TF1 proliferation assay and the difference in potencies between human and cyno TNF-alpha and IL-6 respectively.

| | | | | | | | |
|---|---|---|---|---|---|---|---|
| F027200179 | 9GS | 1C02 | medium | 7.59E−11 | 2.0 | 5.83E−10 | 2.5 |
| F027200183 | 9GS | ALB | medium | 1.03E−10 | 2.4 | 4.61E−10 | 1.6 |
| F027200185 | 9GS | ALB | low | 7.43E−11 | 4.1 | 5.98E−10 | 1.8 |
| F027200192 | 9GS | 10A06 | low | 6.85E−11 | 4.3 | 8.16E−10 | 1.9 |
| F027200196 | 9GS | ALB | low | 7.31E−11 | 5.8 | 5.50E−10 | 1.5 |
| F027200201 | 9GS | 10A06 | medium | 6.80E−11 | 3.5 | 6.98E−10 | 3.0 |
| F027200218 | 9GS | ALB | low | 1.02E−10 | 3.4 | 7.41E−10 | 2 |
| F027200219 | 9GS | VHH#3E | low | 7.30E−11 | 9.6 | 5.85E−10 | 2.5 |
| F027200782 | | | medium | 9.53E−10 | 3.32 | 3.27E−10 | 3.0 |
| F027200925 | | | high | 6.43E−11 | 4.1 | 6.1E−10 | 2.8 |
| F027200154 | | | low | 1.64E−10 | 2.8 | 4.15E−10 | 2.1 |
| F027200155 | | | high | 1.15E−09 | 3.1 | 4.05E−10 | 2.2 |
| F027200187 | 9GS | 1C02 | medium | 5.64E−11 | 2.7 | 3.43E−10 | 2.6 |
| F027200189 | 9GS | 17C04 | medium | 5.31E−11 | 3.1 | 4.91E−10 | 2.2 |
| F027200193 | 9GS | 17C04 | low | 5.95E−11 | 4.7 | 4.23E−10 | 1.8 |
| F027200210 | 9GS | VHH#3E | low | 7.20E−11 | 4.8 | 3.23E−10 | 2 |
| F027200213 | | | medium | 1.53E−09 | 9.5 | 2.94E−10 | 2 |
| F027200215 | | | medium | 2.39E−10 | 2.7 | 3.02E−10 | 2 |
| F027200156 | | | medium | 1.10E−09 | 3.5 | 3.05E−09 | 9.9 |
| F027200157 | | | medium | 1.24E−10 | 4.0 | 3.33E−09 | 7.1 |
| F027200164 | | | medium | 1.12E−09 | 5.4 | 2.40E−09 | 10.3 |
| F027200166 | | | medium | 1.60E−10 | 3.3 | 2.25E−09 | 10.0 |
| F027200180 | 9GS | 1C02 | medium | 7.13E−11 | 2.9 | 3.55E−09 | 2.4 |
| F027200188 | 9GS | VHH#3E | low | 5.58E−11 | 4.4 | 2.68E−09 | 2.7 |
| F027200190 | 9GS | 6B12 | low | 7.93E−11 | 3.2 | 2.77E−09 | 2.9 |
| F027200194 | 9GS | 6B12 | low | 6.47E−11 | 4.3 | 2.36E−09 | 4.4 |
| F027200170 | | | medium | 1.09E−10 | 4.1 | 9.04E−11 | 1.2 |
| F027200171 | | | medium | 8.42E−10 | 4.5 | 1.02E−10 | 1.0 |
| F027200172 | | | medium | 8.64E−11 | 4.5 | 1.12E−10 | 1.7 |
| F027200173 | | | medium | 6.27E−10 | 4.4 | 1.15E−10 | 1.7 |
| F027200184 | 9GS | ALB | medium | 1.04E−10 | 2.1 | 1.06E−10 | 2.6 |
| F027200186 | 9GS | ALB | low | 6.51E−11 | 4.8 | 2.05E−10 | 3.0 |
| F027200197 | 9GS | ALB | low | 7.72E−11 | 5.9 | 2.56E−10 | 2.8 |
| F027200198 | 9GS | ALB | low | 7.77E−11 | 2.6 | 2.51E−10 | 3.2 |
| F027201056 | 9GS | ALB | low | 3.426E−11 | 2.2 | 1.44E−10 | 0.5 |
| F027201057 | 9GS | ALB | medium | 1.9E−10 | 2.0 | 5.77E−10 | 0.4 |
| F027201060 | | | medium | 9.995E−11 | 1.8 | 1.27E−10 | 0.4 |
| F027201061 | | | high | 7.125E−11 | 2.5 | 1.47E−10 | 0.7 |
| F027200981 | 9GS | ALB | nd | nd | | 1.86E−10 | 59.7 |
| F027200983 | 9GS | ALB | nd | nd | | 1.38E−10 | 42.7 |
| F027200987 | | | medium | nd | | 1.43E−10 | 29.4 |
| F027200989 | | | medium | nd | | 1.27E−10 | 38.3 |

BB = building block, ALB = ALB23002. nd = not determined.
Expression level criteria: low = <50 μg/ml,
medium = 51-100 μg/ml,
high = >101 μg/ml Some constructs showed impaired potencies and expression depending on valency, the ISVD building block used, and the relative position of ISVD building blocks. Bispecific ISVDs comprising antd-TNFa ISVDs TNF006C11, bivalent TNF001C02 and bivalent VHH #3E showed potencies similar to the reference anti-TNFa mAb (benchmark monoclonal antibody directed against TNF-alpha), whereas ISVDs comprising monovalent TNF001C02 were 5 to 25 fold less potent than the reference anti-TNFa mAb. All ISVDs comprising bivalent VHH #3E showed low expression levels and were hence deselected.

All bispecific ISVDs comprising anti-IL-6 ISVD IL6006806 showed impaired potency, with the 6B06-6B12 combination performing least. All bispecific ISDVs comprising the anti-IL-6 ISVD IL6013F12 showed degradation upon expression in *Pichia pastoris* and were hence not manufacturable. The remaining bispecific ISVDs comprising the biparatopic anti-IL-6 ISVDs 10A06-7G09,17C04-7G09,17C04-6B12,6B12-7G09 and 7G09-6B12 showed in general potencies similar to anti-IL-6 reference mAb 1, however for 7G09-6B12 the cross-reactivity towards cyno IL-6 was largely impaired.

Subsequently, the large panel was trimmed down to a smaller panel of multispecific constructs, consisting of seven ISVD constructs: F027200809, F027200812, F027200817, F027200927, F027201060, F027201061 and F027201062, proven to be potent on both targets (human and cyno) and having the potential of high expression levels, based on preliminary yield estimates. Three additional ISVD constructs, F027200925, F027200926, F027201029 were selected, mainly based on their potential of high expression levels. However, the latter three constructs showed high potency to one target, while being only medium potent on the other target (Table 7a).

The configuration of ISVD constructs F027200927 and F027200925 is given in Table 7b.

Tables 7c and 7d provide the sequences of each of the individual building blocks of ISVD constructs F027200927 and F027200925, respectively.

Tables 7e, 7f, 7g and 7 h provide the sequences of the three CDR regions and four framework regions present in each of the individual building blocks of ISVD constructs F027200927 and F027200925 (both according to AbM and Kabat numbering). Finally, Table 7l provides the full amino acid sequence of ISVD constructs F027200927 and F027200925.

TABLE 7a

IC50 values for neutralization of human and cyno TNFa in the Nfkb assay and of human and cyno IL-6 in the TF1 proliferation assay for a selected panel of 10 anti-TNFa/anti IL-6 bispecific ISVDs versus the reference compounds.

| ISVD construct ID | BB1 | linker 1 | BB2 | linker 2 | BB3 | linker 3 | BB4 | linker 4 | BB5 | hTNF-α Nfkb assay (IC50, pM) |
|---|---|---|---|---|---|---|---|---|---|---|
| F027200809 | 6C11 | 9GS | 17C04 | 9GS | ALB | 9GS | 7G09 | | | 141 |
| F027200812 | 17C04 | 9GS | ALB | 9GS | 7G09 | 9GS | 6C11 | | | 206 |
| F027200817 | 1C02 | 9GS | 17C04 | 9GS | 1C02 | 9GS | 7G09 | 9GS | ALB | 68 |
| F027200925 | 6C11 | 9GS | 6B06 | 9GS | ALB | 9GS | 10A06 | | | 64 |
| F027200926 | 1C02 | 9GS | 10A06 | 9GS | ALB | 9GS | 7G09 | | | 453 |
| F027200927 | 6C11 | 9GS | 10A06 | 9GS | ALB | 9GS | 7G09 | | | 59 |
| F027201029 | 6C11 | 9GS | 17C04 | 9GS | ALB | 9GS | 6B06 | | | 69 |
| F027201060 | 06B12 | 9GS | ALB | 9GS | 7G09 | 9GS | 6C11 | | | 100 |
| F027201061 | 6C11 | 9GS | 06B12 | 9GS | ALB | 9GS | 7G09 | | | 71 |
| F027201062 | 17C04 | 9GS | ALB | 9GS | 06B12 | 9GS | 6C11 | | | 98 |

| ISVD construct ID | Ratio IC50 reference anti-TNF-α mAb/Nb | cyno TNF-α NFkb assay (IC50, pM) | hIL-6 TF1 proliferation assay (IC50, pM) | Ratio IC50 reference anti-IL-6 mAb1/Nb | cyno IL-6 TF1 proliferation assay (IC50, pM) |
|---|---|---|---|---|---|
| F027200809 | 0.91 | 329 | 68 | 1.7 | 61 |
| F027200812 | 0.62 | 360 | 72 | 1.7 | 54 |
| F027200817 | 0.50 | 108 | 64 | 1.6 | 69 |
| F027200925 | 1.43 | 265 | 610 | 14.8 | 1710 |
| F027200926 | 5.20 | 2670 | 59 | 1.5 | 72 |
| F027200927 | 4.20 | 254 | 71 | 1.8 | 72 |
| F027201029 | 0.83 | 139 | 347 | 5.3 | 209 |
| F027201060 | 0.67 | 176 | 127 | 2.3 | 49 |
| F027201061 | 0.91 | 176 | 147 | 2.7 | 101 |
| F027201062 | 0.67 | 193 | 134 | 2.4 | 65 |

ALB = ALB23002, BB = building block

Table 7b: F027200927 end F027200925 Configurations
*C-Terminal Extension of a Single Alanine TABLE 7c Amino acid sequences of the different monovalent Van building blocks identified within

| Name | Building block 1 | Linker | Building block 2 | Linker | Building block 3 | Linker | Building block 4 |
|---|---|---|---|---|---|---|---|
| F027200927 | 6C11 | 9GS | 10A06 | 9GS | ALB23002 | 9GS | 7G09+A* |
| F027200925 | 6C11 | 9GS | 6B06 | 9G5 | ALB23002 | 9GS | 10A06+A* | the tetravalant polypeptide F027200927 ("ID" refers to the SEQ ID NO as used herein)

| Name | ID | Amino acid sequence |
|---|---|---|
| 6C11 (ant-HTNF-α) | 5 | EVQLVESGGGVVQPGGSLRLSCTASGFTFSTADMGWFRQAPGKGRE FVARISGIDTTYYDEPVKGRFTISRDNSKNTVYLQMNSLRPEDTALYY CRSPRYADQWSAYDYWGQGTLVKVSS |
| 10A06 (anti-hIL-6) | 148 | EVQLVESGGGVVQPGGSLRLSCAASGRTFSSYVMGWFRQAPGKERE FVSTINWAGSRGYYADSVKGRFTISRDNAKNTVYLQMNSLRPEDTAL YYCAASAGGFLVPRVGQGYDYWGQGTLVTVSS |
| ALB23002 (anti-HSA) | 3 | EVQLVESGGGVVQPGGSLRLSCAASGFTFRSFGMSWVRQAPGKGPE WVSSISGSGSDTLYADSVKGRFTISRDNSKNTLYLQMNSLRPEDTALYY CTIGGSLSRSSQGTLVTVSS |
| 7G09 (anti-hIL-6) | 149 | EVQLVESGGGVVQPGGSLRLSCAASGFSLDYYGVGWPRQAPGKERE GVSCISSSEGDTYYADSVKGRFTISRDNAKNTVYLQMNSLRPEDTALYY CATDLSDYGVCSRWPSPYDYWGQGTLVKVSS |

TABLE 7d

Amino add sequences of the different monovalent V_{HH} building blocks identified within the tetravalent polypeptide F027200925 ("ID" refers to the SEQ ID NO as used herein)

| Name | ID | Amino acid sequence |
|---|---|---|
| 6C11 (ati-hTNF-α) | 5 | EVQLVESGGGVVQPGGSLRLSCTASGFTFSTADMGWFRQAPGKGREFVARISGIDGTTYYDEPVKGRFTISRDNSKNTVYLQMNSLRPEDTALYYCRSPRYADQWSAYDYWGQGTLVKVSS |
| 6B06 (ati-hIL-6) | 159 | EVQLVESGGGVVQPGGSLRLSCAASGIIFSINAMGWYRQAPGKQRELVADIFPFGSTEYADSVKGRFTISRDNAKNTVYLQMNSLRPEDTALYYCHSYDPRGDDYWGQGTLVTVSS |
| ALB23002 (anti-HSA) | 3 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| 10A06 (anti-hIL-6) | 148 | EVQLVESGGGVVQPGGSLRLSCAASGRTFSSYVMGWFRQAPGKEREFVSTINWAGSRGYYADSVKGRFTISRDNAKNTVYLQMNSLRPEDTALYYCAASAGGFLVPRVGQGYDYWGQGTLVTVSS |

TABLE 7e

Sequences for CDRs of individual V_{HH} building blocks of tetravalent polypeptide F027200927 according to AbM numbering and frameworks ("ID" refers to the given SEQ ID NO)

| Building block | ID | F81 | ID | CDR1 | ID | FR2 | ID | CDR2 | ID | FR3 | ID | CDR3 | ID | FRA | ID |
|---|---|---|---|---|---|---|---|---|---|---|---|---|---|---|---|
| 6C11 | 5 | EVQLVESGGGVVQPGGSLRLSCTAS | 20 | GFTFSTADMG | 9 | WFRQAPGKGREFVA | 24 | RISGIDGTTY | 13 | YDEPVKGRFTISRDNSKNTVYLQMNSLRPEDTALYYCRS | 28 | PRYADQWSAYDY | 17 | WGQGTLVKVSS | 32 |
| 10A06 | 148 | EVQLVESGGGVVQPGGSLRLSCAAS | 19 | GRTFSSYVMG | 150 | WFRQAPGKEREFVS | 156 | TINWAGSRGY | 151 | YADSVKGRFTISRDNAKNTVYLQMNSLRPEDTALYYCAA | 25 | SAGGPLVPRVGQGYDY | 152 | WGQGTLVTVSS | 29 |
| ALB23002 | 3 | EVQLVESGGGVVQPGGSLRLSCAAS | 19 | GFTFRSFGMS | 7 | WVRQAPGKGPEWVS | 22 | SISGSGSDTL | 11 | YADSVKGRFTISRDNSKNTLYLQMNSLRPEDTALYYCTI | 26 | GGSLSR | 15 | SSQGTLVTVSS | 30 |
| 7G09 | 149 | EVQLVESGGGVVQPGGSLRLSCAAS | 19 | GFSLDYYGVG | 153 | WFRQAPGKEREGVS | 23 | CISSSEGDTY | 154 | YADSVKGRFTISRDNAKNTVYLQMNSLRPEDTALYYCAT | 157 | DLSDYGVCSRWPSPYDY | 155 | WGQGTLVKVSS | 32 |

TABLE 7

Sequences for CDRs of individual VaM building blocks of tetravalent polypeptide F027200925 according to AbM numbering and frameworks ("ID" refers to the given SEQ ID NO)

| Building block | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 6C11 | 5 | EVQLVESGGGVVQPGGSLRLSCTAS | 20 | GFTFSTADMG | 9 | WFRQAPGKGREFVA | 24 | RISGIDGTTY | 13 | YDEPVKGRFTISRDNSKNTVYLQMNSLRPEDTALYYCRS | 28 | PRYADQWSAYDY | 17 | WGQGTLVKVSS | 32 |
| 6B06 | 159 | EVQLVESGGGVVQPGGSLRLSCAAS | 19 | GIIFSINAMG | 160 | WYRQAPGKGREILVA | 163 | DIFPFGSTE | 161 | YADSVKGRFTISRDNAKNTVYLQMNSLRPEDTALYYCHS | 164 | YDPRGDDY | 162 | WGQGTLVTVSS | 29 |
| AL823002 | 3 | EVQLVESGGGVVQPGGSLRLSCAAS | 19 | GFTFRSFGMS | 7 | WVRQAPGKGPEWVS | 22 | SISGSGSDTL | 11 | YADSVKGRFTISRDNSKNTLYLQMNSLRPEDTALYYCTI | 26 | SGSLSR | 15 | SSQGTLVTVSS | 30 |
| 10A06 | 148 | EVQLVESGGGVVQPGGSLRLSCAAS | 19 | GRTFSSYVMG | 150 | WFRQAPGKEREFVS | 156 | TINWAGSRGY | 151 | YADSVKGRFTISRDNAKNTVYLQMNSLRPEDTALYYCAA | 25 | SAGGFLVPRVGQSYDY | 152 | WGQGTLVTVSS | 29 |

TABLE 7g

Sequences for CDRs of individual V_HH building blocks of tetravalent polypeptide F027200927 according to Kabat numbering and frameworks ("ID" refers to the given SEQ ID NO)

| Building block | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 6C11 | 5 | EVQLVESGGGVVQPGGSLRLSCTASGFTFS | 44 | TADMG | 36 | WFRQAPGKGREFVA | 24 | RISGIDGTTYYDEPVKG | 40 | RFTISRDNSKNTVYLQMNSLRPEDTALYYCRS | 48 | PRYADQWSAYDY | 17 | WGQGTLVKVSS | 32 |
| 10A06 | 148 | EVQLVESGGGVVQPGGSLRLSCAASGRTFS | 169 | SYVMG | 165 | WFRQAPGKEREFVS | 156 | TINWAGSRGYYADSVKG | 166 | RFTISRDNAKNTVYLQMNSLRPEDTALYYCAA | 45 | SAGGFLVPRVGQGYDY | 152 | WGQGTLVTVSS | 29 |
| AL823002 | 3 | EVQLVESGGGVVQPGGSLRLSCAASGFTFR | 42 | SFGMS | 34 | WVRQAPGKGPEWVS | 22 | SISGSGSDTLYADSVKG | 38 | RFTISRDNSKNTLYLQMNSLRPEDTALYYCTI | 46 | GGSLSR | 15 | SSQGTLVTVSS | 30 |
| 7G09 | 149 | EVQLVESGGGVVQPGGSLRLSCAASGFSLD | 175 | YYGVG | 167 | WFRQAPGKEREGVS | 23 | CISSSEGDTYADSVKG | 168 | RFTISRDNAKNTVYLQMNSLRPEDTALYYCAT | 170 | DLSDYGVCSRWPSPYDY | 155 | WGQGTLVKVSS | 32 |

TABLE 7h

Sequences for CDRs of individual V_HH building blocks of tetravalent polypeptide F027200925 according to Kabat numbering and frameworks ("ID" refers to the given SEQ ID NO)

| Building block | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 6C11 | 5 | EVQLVESGGGVVQPGGSLRLSCTASGFTFS | 44 | TADMG | 36 | WFRQAPGKGREFVA | 24 | RISGIDGTTYYDEPVKG | 40 | RFTISRDNSKNTVYLQMNSLRPEDTALYYCRS | 48 | PRYADQWSAYDY | 17 | WGQGTLVKVSS | 32 |
| 6B06 | 159 | EVQLVESGGGVVQPGGSLRLSCAASGIIFS | 173 | INAMG | 171 | WYRQAPGKGRELVA | 163 | DIFPFGSTEYADSVKG | 172 | RFTISRDNAKNTVYLQMNSLRPEDTALYYCHS | 174 | YDPRGDDY | 162 | WGQGTLVTVSS | 29 |
| AL823002 | 3 | EVQLVESGGGVVQPGGSLRLSCAASGFTFR | 42 | SFGMS | 34 | WVRQAPGKGPEWVS | 22 | SISGSGSDTLYADSVKG | 38 | RFTISRDNSKNTLYLQMNSLRPEDTALYYCTI | 46 | SGSLSR | 15 | SSQGTLVTVSS | 30 |
| 10A06 | 148 | EVQLVESGGGVVQPGGSLRLSCAASGRTFS | 169 | SYVMG | 165 | WFRQAPGKEREFVS | 156 | TINWAGSRGYYADSVKG | 166 | BFTISRDNAKNTVYLQMNSLRPEDTALYYCAA | 45 | SAGGFLVPRVGQGYDY | 152 | WGQGTLVTVSS | 29 |

TABLE 7i

Amino acid sequences of selected multivalent polypeptides F027200927 and F027200925 ("ID" refers to the given SEQ ID NO)

| Name | ID | Amino acid sequence |
|---|---|---|
| F027200927 | 147 | DVQLVESGGGVVQPGGSLRLSCTASGFTFSTADMGWFRQAPGKGREFVARISGIDGTTYYDEPVKGRFTISRDNSKNTVYLQMNSLRPEDTALYYCRSPRYADQWSAYDYWGQGTLVTVSSGGGGSGGGSEVQLVESGGGVVQPGGSLRLSCAASGRTFSSYVMGWFRQAPGKEREFVSTINWAGSRGYYADSVKGRFTISRDNAKNTVYLQMNSLRPEDTALYYCAASAGGFLVPRVGQGYDYWGQGTLVTVSSGGGGSGGGSEVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSGGGGSGGGSEVQLVESGGGVVQPGGSLRLSCAASGFSLDYYGVGWFRQAPGKEREGVSCISSSEGDTYYADSVKGRFTISRDNAKNTVYLQMNSLRPEDTALYYCATDLSDYGVCSRWPSPYDYWGQGTLVKVSSA |
| F027200925 | 158 | DVQLVESGGGVVQPGGSLRLSCTASGFTFSTADMGWFRQAPGKGREFVARISGIDGTTYYDEPVKGRFTISRDNSKNTVYLQMNSLRPEDTALYYCRSPRYADQWSAYDYWGQGTLVTVSSGGGGSGGGSEVQLVESGGGVVQPGGSLRLSCAASGIIFSINAMGWYRQAPGKQRELVADIFPPFGSTEYADSVKGRFTISRDNAKNTVYLQMNSLRPEDTALYYCHSYDPRGDDYWGQGTLVTVSSGGGGSGGGSEVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSGGGGSGGGSEVQLVESGGGVVQPGGSLRLSCAASGRTFSSYVMGWFRQAPGKEREFVSTINWAGSRGYYADSVKGRFTISRDNAKNTVYLQMNSLRPEDTALYYCAASAGGFLVPRVGQGYDYWGQGTLVKVSSA |

Larger scale 2L and 5L productions in *Pichia pastoris* of the panel comprising the 11 ISVD constructs were done for expression yield determination, assessment of biophysical properties. It was demonstrated that a specific combination of the anti-IL-6 building blocks and anti-TNF-α building blocks was required to obtain high expression yields as well as sufficient solubility and biophysical stability. This is exemplified in Table 8. For instance, constructs F027201062 and F027200812 which are very similar in composition except for one building block on the third position, display significantly different expression and solubility profiles.

mouse SA) were mixed to allow interaction and incubated for either 48 or 72 hours (in case of IL-6 and TNFα) or 2 hours (in case of SA) to reach equilibrium.

Biotinylated human TNF-α/IL-6/serum albumin was captured in the microstructures of a Gyrolab Bioaffy 1000 CD, which contains columns of beads and is used as a molecular probe to capture free F027201062 from the equilibrated solution. The mixture of TNF-α/IL-6/serum albumin and F027201062 (containing free TNF-α/IL-6/serum albumin, free F027201062 and TNF-α/IL-6/serum albumin—F027201062 complexes) was allowed to flow through the

TABLE 8

Expression yields, solubility and biophysical properties at highest concentration for a selected panel of 10 anti-TNFa/anti IL-6 bispecific ISVDs.

| ISVD construct ID | BB1 | linker 1 | BB2 | linker 2 | BB3 | linker 3 | BB4 | linker 4 | BB5 | Expression yield 2 L fermentor (g/L) | solubility (mg/ml) |
|---|---|---|---|---|---|---|---|---|---|---|---|
| F027200809 | 6C11 | 9GS | 17C04 | 9GS | ALB | 9GS | 7G09 | | | 3.6 | <50 |
| F027200812 | 17C04 | 9GS | ALB | 9GS | 7G09 | 9GS | 6C11 | | | 2.5 | <50 |
| F027200817 | 1C02 | 9GS | 17C04 | 9GS | 1C02 | 9GS | 7G09 | 9GS | ALB | 3.5 | 132 |
| F027200925 | 6C11 | 9GS | 6B06 | 9GS | ALB | 9GS | 10A06 | | | 6.7 | 124 |
| F027200926 | 1C02 | 9GS | 10A06 | 9GS | ALB | 9GS | 7G09 | | | 5.4 | 141 HMW formation 5° C. |
| F027200927 | 6C11 | 9GS | 10A06 | 9GS | ALB | 9GS | 7G09 | | | 5.1 | 112 Phase separation and gelformation |
| F027201029 | 6C11 | 9GS | 17C04 | 9GS | ALB | 9GS | 6B06 | | | 6.4 | 152 Gel formation |
| F027201060 | 06B12 | 9GS | ALB | 9GS | 7G09 | 9GS | 6C11 | | | 6.5 | 153 Gel formation |
| F027201061 | 6C11 | 9GS | 06B12 | 9GS | ALB | 9GS | 7G09 | | | 4.9 | 152 Gel formation |
| F027201062 | 17C04 | 9GS | ALB | 9GS | 06B12 | 9GS | 6C11 | | | 5.1 | 149 |

ALB = ALB23002, BB = building block, SVP subvisible particles, HMW = high molecular weight, nd = not determined Finally, ISVD construct F027201062 was selected for further characterization because of its combined good performance on potency and CMC characteristics (e.g. solubility and expression).

Example 4: Multispecific ISVD Construct: Binding Affinity to TNF-α, IL-6 and Serum Albumin The affinity, expressed as the equilibrium dissociation constant (KD), of F027201062 towards human and cynomolgus monkey TNF-α and IL-6 and human, cyno and mouse serum albumin (SA) was quantified by means of in-solution affinity measurements on a Gyrolab xP Workstation (Gyros).

Under KD-controlled measurements a serial dilution of TNF-α or IL-6 (ranging from 1.3 μM-0.1 pM) or human or cyno SA (ranging from 13 μM-1 pM) or mouse SA (ranging from 133 μM-30 pM) and a fixed amount of F027201062 (80 pM in case of TNF-α, 20 pM in case of IL-6, 300 pM in case of human and cyno SA and 600 pM in case of mouse SA) were mixed to allow interaction and incubated for either 48 or 72 hours (in case of IL-6 and TNF-α) or 2 hours (in case of SA) to reach equilibrium.

Under receptor-controlled measurements a serial dilution of TNF-α or IL-6 (ranging from 1.3 μM-0.1 pM) or human and cyno SA (ranging from 13 μM-1 pM) or mouse SA (ranging from 133 μM-30 pM) and a fixed amount of F027201062 (30 nM in case of TNFα, 5 nM in case of IL-6, 1 μM in case of human and cyno SA and 2 μM in case of beads, and a small percentage of free F027201062 was captured, which is proportional to the free ISVD construct concentration. A fluorescently labeled anti-VHH antibody, ABH0086-Alexa647, was then injected to label any captured F027201062 and after rinsing away excess of fluorescent probe, the change in fluorescence was determined. Fitting of the dilution series was done using Gyrolab Analysis software, where KD- and receptor-controlled curves were analyzed to determine the KD value. The results (Table 9) demonstrate that the multispecific ISVD construct binds human/cyno IL-6 and human/cyno TNF-α with high affinity.

TABLE 9

Binding affinities of F027201062 to human and cyno TNF-α and IL-6 and human, cyno and mouse serum albumin (SA).

| Antigen | | Human $K_D$ (pM) | Cyno $K_D$ (pM) | Mouse $K_D$ (pM) |
|---|---|---|---|---|
| TNF-α | n = 1 | 5.7 | 53.8 | / |
| | n = 2 | 5.2 | 23.7 | |
| | n = 3 | 9.9 | 25.9 | |
| IL-6 | n = 1 | 7.3 | 13.7 | / |
| | n = 2 | 5.3 | 3.0 | |
| | n = 3 | 3.0 | 6.2 | |
| SA | n = 1 | 7600 | 6700 | 58500 |
| | n = 2 | 6400 | 4900 | 62200 |
| | n = 3 | 6200 | 6100 | 56000 |

6.4 Example 5: Multispecific ISVD Construct Binding to Membrane Bound TNFα

Binding of F027201062 to membrane bound TNFα was demonstrated using flow cytometry on human membrane TNFα expressing HEK293H cells. Briefly, cells were fixed with 4% paraformaldehyde and 0.1% glutaraldehyde in PBS (to increase detection of membrane bound TNFα). Subsequently, cells were seeded at a density of $1 \times 10^4$ cells/well and incubated with a dilution series of F027201062 or the anti-TNFα reference mAb, starting from 100 nM up to 0.5 pM, in absence or in the presence of 30 μM HSA, for 24 hours at room temperature. Cells were washed 3 times and subsequently incubated with an anti-VHH mAb (ABH00119) for 30 min at 4'C, washed again, and incubated for 30 min at 4'C with a goat anti-mouse or anti-human PE labeled antibody. Samples were washed and resuspended in FACS Buffer (D-PBS with 10% FBS and 0.05% sodium azide supplemented with 5 nM TOPRO3). Cell suspensions were then analyzed on an iQuescreener. EC50 values were calculated using GraphPad Prism. EC50 values for F027201062 and the anti-TNFα reference mAb are comparable (Table 10).

TABLE 10

Binding affinity of F027201062 to membrane expressed TNFα after incubation of 24 hours, compared to the anti-hTNFα reference mAb.

| | Condition | | | | | |
|---|---|---|---|---|---|---|
| | +HSA | | | −HSA | | |
| n= | 1 | 2 | 3 | 1 | 2 | 3 |
| Sample ID | F027201062 | | | | | |
| EC50 (M) | 3.10E−10 | 2.90E−10 | 3.60E−10 | 1.20E−10 | 1.80E−10 | 1.70E−10 |
| Sample ID | reference anti-TNFa mAb | | | | | |
| EC50 (M) | 3.3E−11 | 2.93E−11 | 1.95E−11 | 3.8E−11 | nd | 9.80E−12 |

6.5 Example 6: Multispecific ISVD Construct Binds Selectively to TNF-α and IL-6

Absence of binding to TNF-α and IL-6 related human targets was assessed via SPR (Proteon XPR36). As IL-6 related cytokines or cytokines sharing the gp130 receptor, human IL23, IL27, CNTF, oncostatin M (OSM) and IL11 were assessed. TNF superfamily members human FASL, TNFβ, LIGHT, TL-1A, RANKL were tested as related cytokines for TNFα.

To this end, the targets were immobilized on a proteon GLC sensor chip at 25 μg/mL for 200 s using amine coupling, with 80 seconds injection of EDC/NHS for activation and a 150 seconds injection of 1 M ethanolamine HCl for deactivation (ProteOn Amine Coupling Kit. cat. 176-2410). Flow rate during activation, deactivation and ligand injection was set to 30 μl/min. The pH of the 10 mM acetate immobilization buffer was chosen by subtracting ~1.5 from the pI of each ligand. Next, 300 nM of F027201062 was injected for 2 minutes and allowed to dissociate for 600 s at a flow rate of 45 μl/min. As running buffer PBS (pH7.4)+ 0.005% Tween 20 was used. As positive controls 0.3 μM α-IL11 Ab, α-OSM Ab, α-CNTF Ab, α-IL27 Ab, α-IL27A Ab, α-IL23 p19 Ab, α-hFASL Ab, 0.3 μM α-hTNFβ Ab, 0.5 μM α-hLIGHT Ab, 0.3 μM α-hTL-1A Ab and 0.5 μM α-hRANKL VHH were injected.

Interaction between F027201062 and the positive controls with the immobilized targets was measured by detection of increases in refractory index which occurs as a result of mass changes on the chip upon binding.

All positive controls did bind to their respective target. No binding was detected of ISVD construct F027201062 to human TRAIL, CD30L, CD40L, FASL, TNF, LIGHT, TL-1A, RANKL, 1L23, IL27, CNTF, oncostatin M and IL11.

6.6 Example 7: Simultaneous Binding of Multispecific ISVD Construct to hIL-6, hTNFa and HSA A Biacore 8K+ instalment was used to determine whether ISVD construct F027201062 can bind simultaneously to recombinant soluble hTNF-α and hIL-6. To this end HSA was immobilized on a CM5 sensor chip via amine coupling to a level of ~1600 RU. 100 nM of F027201062 was injected for 2 min at 10 μl/min over the HSA surface in order to capture the ISVD construct via the ALB23002 building block. Subsequently either 100 nM of hIL-6, hTNF-α or hOX40L were injected or mixtures of 100 nM IL-6+100 nM TNFα, 100 nM IL-6+100 nM OX40L or 100 nM TNF-α+ 100 nM OX40L at a flow rate of 45 μl/min for 2 min followed by a subsequent 600 seconds dissociation step. The HSA surfaces are regenerated with a 2-minute injection of HCl (100 mM) at 45 μl/min. The sensorgram (FIG. 1) demonstrates that ISVD construct F027201062 can bind hIL-6 and hTNF-α simultaneously as shown by the increase in response units after capture on HSA: ~150 RU increase from hTNF-α only, ~120 RU increase from hIL-6 only and ~340 RU increase for the IL-6 and TNF-α mixture.

6.7 Example 8: Multispecific ISVD Construct Inhibition of TNF-α-Induced NFκB Activation in Vitro HEK293_NFκB-NLucP cells are TNF receptor expressing cells that were stably transfected with a reporter construct encoding Nano luciferase under control of a NFκB dependent promoter. Incubation of the cells with soluble human and cyno TNF-α resulted in NFκB mediated Nano luciferase gene expression. Nano luciferase luminescence was measured using Nano-Glo Luciferase substrate mixed with lysing buffer at the ratio of 1:50 added onto cells. Samples were mixed 5 min on a shaker to obtain complete lysis. Glo Response™ HEK293_NFκB-NLucP cells were seeded at 20000 cells/well in normal growth medium in white tissue culture (TC) treated 96-well plates with transparent bottom. Dilution series of F027201062 or the anti-TNF-α reference mAb were added to 25 μM human or 70 μM cyno TNF-α and incubated with the cells for 5 hours at 37° C. in the presence of 30 μM HSA. F027201062 inhibited human and cyno TNF-α-induced NFκB activation in a concentration dependent manner with an average IC50 of 53 μM (for human TNF-α) and 158 μM (for cyno TNF-α) comparable to the reference compound anti-hTNF-α mAb (Table 11, FIG. 2). The negative control ISVD, IRR00096, did not show inhibition.

TABLE 11

IC50 and IC90 values of F027201062 mediated neutralization of human and cyno TNFα in the Glo response ™ HEK293_NFκB-NLucP reporter assay versus the anti-TNFα reference mAb.

| | human TNF-α | | | cyno TNF-α | | |
|---|---|---|---|---|---|---|
| | n = 1 | n = 2 | n = 3 | n = 1 | n = 2 | n = 3 |
| | F027201062 | | | | | |
| IC50 (M) | 7.57E−11 | 2.57E−11 | 5.86E−11 | 1.60E−10 | 8.37E−11 | 2.30E−10 |
| IC90 (M) | 3.51E−10 | 2.70E−10 | 4.60E−10 | 6.98E−10 | 7.50E−10 | 1.45E−09 |
| | anti-TNF-α reference mAb | | | | | |
| IC50 (M) | 5.54E−11 | 5.92E−11 | 5.90E−11 | 8.45E−11 | 1.05E−10 | 1.28E−10 |
| IC90 (M) | 2.97E−10 | 4.09E−10 | 3.42E−10 | 4.38E−10 | 8.85E−10 | 8.40E−10 |

6.8 Example 9: Multispecific ISVD Construct Inhibition of IL-6 Induced Proliferation of TF-1 Cells The inhibitory potency of F027201062 was determined in a cell-based assay monitoring IL-6 mediated proliferation of TF-1 cells. To this end, TF-1 cells were cultured in RPMI 1640, glutamax, HEPES medium (Gibco) with the addition of 10% FBS and 1% Na-Pyruvate. TF-1 cells were seeded at 12.500 cells per well in growth medium. A dilution series of the purified anti-IL-6 ISVDs or reference compounds was added. After 30 min incubation at 37° C., 75 pM of human IL-6 (R&D systems cat nr 200-IL-200|206-IL) or cyno IL-6 (Evotek, cat nr APP-7634) was added. After 72 hours, proliferation of the TF-1 cells was determined with CellTiter-Glo (Promega #G7571) on an EnVision Multilabel Reader (Perkin Elmer).

F027201062 Inhibited human and cyno IL-6 induced proliferation of TF-1 cells in a concentration-dependent manner with an average IC50 of 34 pM (for human IL-6) and 56 pM (for cyno IL-6), comparable to the anti-IL-6 reference mAb 1 and better than anti-IL-6 reference mAb 2 (Table 12, FIG. 3).

6.9 Example 10: Multispecific ISVD Construct Binding to Pre-Existing Antibodies The pre-existing antibody reactivity of ISVD construct F027201062 was assessed in normal human serum (n=96) using the ProteOn XPR36 (Bio-Rad Laboratories, Inc.). PBS/Tween (phosphate buffered saline, pH7.4, 0.005% Tween20) was used as running buffer and the experiments were performed at 25° C.

ISVDs are captured on the chip via binding of the AL823002 building block to HSA, which is immobilized on the chip. To immobilize HSA, the ligand lanes of a ProteOn GLC Sensor Chip are activated with EDC/NHS (flow rate 30 μl/min) and HSA is injected at 100 μl/ml in ProteOn Acetate buffer pH4.5 to render immobilization levels of approximately 2500 RU. After immobilization, surfaces are deactivated with ethanolamine HCl (flow rate 30 μl/min).

Subsequently, ISVD constructs are injected for 2 min at 45 μl/min over the HSA surface to render an ISVD capture level of approximately 800 RU. The samples containing pre-existing antibodies are centrifuged for 2 minutes at 14,000 rpm and supernatant is diluted 1:10 in PBS-Tween20 (0.005%) before being injected for 2 minutes at 45 μl/min followed by a subsequent 400 seconds dissociation step. After each cycle (i.e. before a new ISVD capture and blood sample injection step) the HSA surfaces are regenerated with a 2 minute injection of HCl (100 mM) at 45 μl/min. Sensorgrams showing pre-existing antibody binding are obtained after double referencing by subtracting 1) ISVD-

TABLE 12

IC50 and IC90 values of F027201062 mediated inhibition of human and cyno IL-6 induced proliferation of TF-1 cells compared to anti-IL-6 reference compounds

| | human IL-6 | | | cyno IL-6 | | |
|---|---|---|---|---|---|---|
| | n = 1 | n = 2 | n = 3 | n = 1 | n = 2 | n = 3 |
| | F027201062 | | | | | |
| IC50 (M) | 1.36E−10 | 4.62E−11 | 4.23E−11 | 6.46E−11 | 5.92E−11 | 4.34E−11 |
| IC90 (M) | 3.75E−10 | 9.63E−11 | 8.10E−11 | 2.15E−10 | 1.97E−10 | 1.68E−10 |
| | Reference anti-IL-6 mAb1 | | | | | |
| IC50 (M) | ambiguous | 2.78E−11 | 3.30E−11 | 3.19E−11 | 3.06E−11 | 3.18E−11 |
| IC90 (M) | ambiguous | 4.48E−11 | 5.70E−11 | 7.50E−11 | 7.45E−11 | 7.08E−11 |
| | Reference anti-IL-6 mAb2 | | | | | |
| IC50 (M) | 1.55E−10 | 5.51E−11 | 5.73E−11 | 7.86E−11 | 5.85E−11 | 5.47E−11 |
| IC90 (M) | 1.54E−09 | 7.35E−10 | 3.80E−10 | 5.06E−10 | 4.58E−10 | 3.48E−10 |

HSA dissociation and 2) non-specific binding to reference ligand lane. Binding levels of pre-existing antibodies are determined by setting report points at 125 seconds (5 seconds after end of association). Percentage reduction in pre-existing antibody binding is calculated relative to the binding levels at 125 seconds of a reference ISVD.

The tetravalent ISVD construct F027201062, optimized for reduced pre-existing antibody binding by introduction of mutations L11V and V89I in each building block and a C-terminal alanine, shows substantially less binding to pre-existing antibodies compared to a control non-optimized pentavalent ISVD construct F027301186 (FIG. 4).

6.10 Example 11: Sustained Long-Term Remission of Murine Collagen-Induced Arthritis with Combination of Murine Anti-TNF-α and Anti-6 Surrogate Antibodies Rheumatoid arthritis is a destructive autoimmune disease attacking peripheral joints. The Collagen-induced Arthritis (CIA) mouse model is recapitulating the erosive disease. To elicit an immune response against components of the joints, susceptible DBA/1 mice were immunized twice with 100 μg adjuvanted chick collagen II. The immune response mounted against the collagen II will spread to endogenous joint cartilage and lead to clinically overt arthritis. After the second immunization on day 21, progressive arthritis became evident by ankle and paw swelling, erythema, and sometimes ankylosis. Arthritis severity was clinically assessed for each of the four paws by a scoring system as detailed in Table 13 below.

TABLE 13

Arthritis scoring system for determining arthritis phenotype severity

| ARTHRITIS SCORE[1] | CHARACTERISTICS |
|---|---|
| 0 | No clinical signs detectable |
| 1 mild | Swelling of ankle or paw |
| 2 moderate | Swelling of ankle and paw, mild erythema |
| 3 severe | Severe swelling of ankle and paw, severe erythema, ankylosis |

[1]arthritis score on the y-axis in FIG. 5: sum of individual paw scores. Max sum score 4 × 3 = 12.

To assess the impact of combined TNF and IL-6 blockade on disease severity and progression, N=13 immunized male DBA/1 mice were treated with blocking antibodies against murine TNF, murine IL-6, or a combination of both. Mice were treated by intraperitoneal injection twice per week, starting at day 22 after the first immunization and commencing until day 55. As depicted in FIG. 5, clinical arthritis progressively develops from day 21 onwards. Mice treated with either anti-muTNF or the combination of anti-muTNF and anti-muIL-6 had a delayed and less severe arthritis progression than mice treated with isotype control antibody or anti-muIL-6 alone. With treatment cessation on day 55, a disease rebound was observable in mice treated with anti-muTNF alone, quickly reaching severity levels comparable to isotype control or anti-muIL-6. However, mice treated with a combination of both anti-muTNF and anti-muIL-6 did not rebound into arthritis progression and maintained response despite stop of treatment. FIG. 6 shows the analysis of the area under the arthritis score over time curve for the whole study duration, for the treatment period, and for the off-treatment period. The latter was significantly suppressed by the combination treatment, indicating a sustained impact on disease progression.

Arthritis in this model is initiated by an antibody response to the collagen II vaccination. At d91, plasma level of anti-collagen II antibodies was determined by ELISA. As depicted in FIG. 7, all treatments reduced anti-collagen II antibody titers, with the greatest numerical reduction in mice treated with both anti-muTNF and anti-muIL-6.

Hind paws were collected after sacrifice of the mice on day 91 and metatarsal joints were processed for histological evaluation of arthritis. Scoring of hematoxylin and eosin as well as safranin-O stained sections was performed across 4 dimensions on a scale from 0-5 in a blinded fashion (Table 14).

TABLE 14

Arthritis histology scoring system

| HISTOLOGY SCORE* | | CHARACTERISTICS |
|---|---|---|
| Inflammation | 1 | Minimal immune cell infiltration into synovium and/or adjacent regions |
| | 2 | Mild infiltration, less than 3 joints affected |
| | 3 | Moderate infiltration, 3-4 joints affected, connective tissue swelling |
| | 4 | Severe infiltration in most joints |
| | 5 | Very severe infiltration in all joints |
| Pannus formation | 1 | Minimal pannus formation in peripheral area, only 1 joint affected |
| | 2 | Mild pannus formation, 1-3 joints |
| | 3 | Moderate pannus formation, 1-3 joints |
| | 4 | Severe pannus formation in most joints, joint deformation |
| | 5 | Very severe pannus formation in all joints, joint deformation |
| Cartilage destruction | 1 | Minimal proteoglycan loss (safranin-O stain) only 1 joint affected |
| | 2 | Proteoglycan loss, up to 3 joints affected |
| | 3 | Majority of proteoglycan lost at many joints |
| | 4 | Severe proteoglycan loss, rough surfaces, dead chondrocytes |
| | 5 | No cartilage left |
| Bone destruction | 1 | Minimal bone resorption visible only at high magnification |
| | 2 | Mild bone resorptions, visible with lower magnification |
| | 3 | Moderate bone resorption, on some cortical surfaces |

TABLE 14-continued Arthritis histology scoring system

| HISTOLOGY SCORE* | CHARACTERISTICS |
|---|---|
| 4 | Severe bone resorption on all cortical surfaces |
| 5 | Bone deformation |

*arthritis score on the y-axis in FIG. 8.

As shown in FIG. 8 statistically significant improvements over isotype control antibody in histology scores for pannus formation and bone destruction were achieved in mice treated with the combination of anti-muTNF and anti-muIL-6.

Taken together, these data suggest highest therapeutic potency of combination treatment blocking both TNF as well as IL-6 inflammatory pathways. Importantly, the combination treatment led to sustained responses even in the absence of active treatment.

6.11 Example 12: RNA-Seq Data Analysis from CA (Collagen Induced Arthritis) Model Treated with Anti-TNF-Alpha, Anti-IL6 and Combined Anti-TNF-Alpha/IL6

Total RNA from mouse front paw tissue samples of CIA was purified using the RNAeasy kit (Qiagen) and paired-end sequencing of 2×51-66 million reads was performed on a NovaSeq platform (Illumina) at ATLAS Biolabs GmbH, Berlin. Bioinformatics analysis of RNA-seq raw data was performed using the OmicsSoft studio software package version 10.01.118 (Qiagen). Mapping of RNA-seq reads (fastq files) to the mouse genome was done using OmicSoft-GenCode.V19 as gene model with mouse B.38 as reference genome and OSA4 as aligner.

Venn Analysis of Differentially Expressed Genes (DEGs)

The Venn diagram in FIG. 9 (A) shows the overlap of DEGs identified from anti-TNF-alpha, anti-IL6 and combined anti-TNF-alpha/IL6 treatment in the CIA model. DEGs were determined by comparing RNA-seq sample groups from treatment with a standard conventional anti-TNF-alpha antibody (n=13 samples), standard conventional anti-1L6 antibody (MPS-20F3; n=13) and combined anti-TNF-alpha/anti-IL-6 antibody (n=13) treatment to samples from isotype treatment (IgG control; n=13) using the DESeq2 statistical test (Love, M. I., Huber, W., Anders, S. Moderated estimation of fold change and dispersion for RNA-seq data with DESeq2. Genome Biol 2014; 15(12): 550). DEGs with log 2 fold changes>1.2 and adjusted p-values<0.05 according to Benjamini-Hochberg (SH-FDR) were considered significant. From number of DEGs, venn analysis indicates additive effects of combined anti-TNF-alpha/IL-6 treatment over mono-treatment with anti-TNF-alpha or anti-IL-6.

Pathway Mapping of Differentially Expressed Genes (DEGs)

Pathway maps in FIG. 9 (B) show the top 20 canonical pathways from gene set enrichment analysis of DEGs using combined curated biological knowledgebases from Ingenuity (Qiagen) and MetaCore (Clarivate). DEGs from collagen induced arthritis (CIA) were determined by comparing samples from isotype treatment (IgG control group, n=13) to untreated samples with no collagen induced arthritis (none group, n=4) using DESeq2. DEGs from combined anti-TNF-alpha/IL6 treatment were determined by comparing samples from anti-TNF-alpha/IL-6 (XT.3+MP5-20F3; n=13) to samples from isotype treatment (IgG control group, n=13) using DESeq2. Metabolic and immune signaling pathways in both maps show inverse scores from collagen induced arthritis and combined anti-TNF-alpha/IL6 treatment at different False Discovery Rates (FDR).

6.12 Example 13: Quantitative Systems Pharmacology (QSP) Model for Rheumatoid Arthritis Predicts Increased Remission at Lower Doses for F027201062 (Compared to Anti-hTNF-α and Anti-hIL-6 Reference mAbs)

Applicant developed a proprietary Quantitative Systems Pharmacology model of rheumatoid arthritis (RA), which considers the relevant tissues, cells and mediators in blood and synovium. The included mechanistic details of biological interactions were parameterized with a broad range of in vitro data, both from in-house and published external sources. Afterwards, the model was tested and validated with clinical data from various studies with methotrexate, JAK-inhibitor, anti-IL-6R, anti-IL-6, anti-TNF treatments.

Based on this model, the reduction in DAS28-CRP, as a result of a reduction in disease activity in the synovium, was simulated for an average patient with moderate to severe rheumatoid arthritis over a treatment time of 52 weeks. The Nanobody F027201062 was able to bind TNF-α and IL-6 simultaneously and achieved a higher reduction in DAS28-CRP compared to the monotherapies with a dose of 20 mg every 2 weeks and predicted the reference patient to achieve DAS28-CRP remission after 24 weeks. The Nanobody simulation considered the human pharmacokinetics predicted from animal and in vitro data. For target binding, the in vitro IC50 data from cellular assays together with published target binding parameters for anti-hTNF and anti-hIL-6 comparator mAbs were used to calculate the target binding parameters of the Nanobody (FIG. 10).

6.13 Example 14: Additive Efficacy of Anti-TNF-α and Anti-IL-6 in Human RA-RS/T Cell Coculture Model on MMP-1 and G-CSF An in vitro model for Rheumatoid Arthritis was developed, mimicking the concentrations of TNF-α and IL-6 in the joints of patients. In brief, fibroblast-like synoviocytes were co-cultured from rheumatoid arthritis patients (RA-FLS) with CD4+ T cells from healthy human donors. Additional stimulation induced endogenous secretion of TNF-α and IL-6. Treatment with anti-hTNF-α and anti-hIL-6 reference mAbs partially reduced secretion of MMP-1 and G-CSF, while combination as well as F027201062 achieved stronger maximal inhibition.

Below a detailed protocol of the assay, which reflects IL-6 trans-signaling, is described:

RA-FLS were seeded at a density of 10.000 cells/well in 96 well format in Synoviocyte Basal Medium with growth supplements (Pelobiotech). On the following day PBMC's were isolated from blood of healthy human donors using Ficoll gradient centrifugation. CD4+ T cells were isolated from PBMC's using magnetic separation (negative selection).

RA-FLS medium was replaced by medium with isotype controls, comparator antibodies and ISVDs in the respective concentrations (1:10 dilution, from 200 nM, 6 concentrations, triplicates). IgG1 isotype control was used as negative control for comparator antibodies, while VHH IRR00119 was used as ISVD isotype negative control. Anti-human TNF-α and anti-human IL-6 reference antibodies were used as comparators. Furthermore, the combination of full dose of both comparators was used as additional positive control and to show additive efficacy. The following ISVD constructs were evaluated in this model: F027200926 and F027201062. Intraplate position of all constructs was varied between the triplicates to avoid plate effects.

Afterwards 100.000 CD4+ T cells (in synoviocyte basal medium with growth supplements) are added to FLS. Finally, this coculture was stimulated with 100 ng/ml human recombinant IL-17A, 100 ng/ml sIL-6R and 100 ng/mi soluble anti-CD3 for 48 h. After 48 h cells were centrifuged and supernatant was collected and stored at −20T. MMP-1 and G-CSF level were measured using Luminex technology. Donors that did not react to the anti-hTNF-α comparator mAb were excluded (no possibility to prove additive efficacy and dual targeting of ISVD constructs).

The endogenous secretion of TNF-α and IL-6 was measured after 48 h stimulation with IL-17A, sIL-6R and anti-CD3. The stimulated coculture induced increased secretion of TNF-α (without stimulation below detection limit) and IL-6. Stimulated coculture secreted 4.4 pg/ml IL-6 and 7977 pg/ml TNF-α (Mean value of 8 donors, FIG. 11). These values are comparable to the median values from human rheumatoid arthritis joints collected from different publications: 24±21 pg/ml TNF-α and 13400±12700 pg/ml IL-6.

For the evaluation of ISVD efficacy on MMP-1 and G-CSF, RA-FLS from one donor were incubated with 8 different human donor T cells. We did not observe a dose-dependent effect of both isotype controls on MMP-1 secretion. Anti-hTNF-α reference mAb partially reduced MMP-1 secretion. Anti-hIL-6 reference mAb was more efficacious than anti-hTNF-α comparator mAb, while the combination of both antibodies showed highest efficacy. Both ISVD constructs were similar efficacious as comparator antibody combination (dosed 200 nM Ab1+200 nM Ab2) and showed dose-dependent effects (FIG. 12, 8 donors). Similar results were obtained for G-CSF (FIG. 13, 8 donors).

6.14 Example 15: Additive Efficacy of Anti-TNF-α and Anti-IL-6 in Human Adenoid Model on CXCL13

We evaluated additive efficacy of F027201062 in a human pharyngeal tonsils (adenoid) model consisting of follicular helper T cells (Tfh) and germinal center B cells. In brief, we performed a high density lymphoid aggregate culture with cryopreserved lymphocytes. This culture was stimulated with mutated pertussis toxin to induce an AIM (activation induced marker) response (Schmidt, A. et al. 2020 Complex human adenoid tissue-based ex vivo culture systems reveal anti-inflammatory drug effects on germinal center T and B cells. EBioMedicine 53, 102684, doi:10.1016/j.ebiom.2020.102684). Treatment with anti-hTNF-α and anti-hIL-6 reference mAbs partially reduced secretion of CXCL13, while combination as well as F027201062 achieved stronger maximal inhibition.

Below a detailed protocol is described:

Adenoid tissue from surgeries was collected in RPMI medium (without supplements) at 4° C. Tissue was further processed after surgery as follows. Adenoid-derived tissues and cells were cultured in RPMI medium (with I-glutamine) containing 15% (v/v) FBS (Gibco Fetal Bovine Serum, qualified, heat inactivated) and supplements (0.1 mM MEM-nonessential amino acids, 1 mM MEM sodium-pyruvate, 50 μg/ml gentamicin, 2.5 μg/ml amphotericin B, 0.3 μg/ml ticarciilin, 0.01 μg/ml clavulanate). Tissue was washed twice with PBS and dissected in a dish with CMT medium (RPMI medium (with 1-glutamine) containing 15% (v/v) FBS (Gibco Fetal Bovine Serum, qualified, heat inactivated) and supplements (0.1 mM MEM-nonessential amino acids, 1 mM MEM sodium-pyruvate, 50 μg/ml gentamicin, 2.5 μg/ml amphotericin B, 0.3 μg/ml ticarcillin, 0.01 μg/ml clavulanate). Bloody, cauterized tissue was discarded. Remaining tissue and cutting medium were routinely strained while mechanically disrupting with syringe plungers through 40 μm cell strainers immersed in CMT medium. Suspension cells were then washed in CMT medium (500×g, 5 min), counted and taken up in 10% DMSO/90% FCS at 12.5-100 Mio cells/ml for cryopreservation.

On the day of the experiment, cryopreserved adenoid suspension cells were thawed, and then cultured in 96U-well plates with $1 \times 10^6$ cells/well. Cells were either left unstimulated or stimulated with Pertussis Toxin mutant (PT; enzymatically inactive point mutant, highly purified and low endotoxin-tested, List Biological Laboratories via Biotrend) at 1 μg/ml final concentration. Where indicated, cultures were treated with the following compounds: isotype controls, comparator antibodies and ISVDs in the respective concentrations (1:10 dilution, from 200 nM, 4.5 concentrations, duplicates). IgG1 isotype control was used as negative control for comparator antibodies, while VHH IRR00119 was used as ISVD isotype negative control. Anti-human TNF-α and anti-human IL-6 reference antibodies were used as comparators. Furthermore, the combination of full dose of both comparators was used as additional positive control and to show additive efficacy. The following ISVD construct was evaluated in this model: F027201062. 18 h after stimulation, cells were centrifuged and supernatant was collected and stored at −20° C. CXCL13 level were determined by ELISA.

For the evaluation of ISVD efficacy on MMP-1 and G-CSF, up to 7 adenoid donors were evaluated (dependent on the tested concentration). Anti-hTNF-α and anti-hIL-6 reference mAb partially reduced CXCL13 secretion. The combination of both anti-hTNF-α and anti-hIL-6 completely inhibited the Pertussis-toxin induced increase in CXCL13 in a dose-dependent manner. F027201062 was similar efficacious as the combination of both comparator antibodies (FIG. 14, 4-7 donors).

Focusing on the maximal efficacy at high concentrations (data for all 7 donors available for 200 nM), we then evaluated the additive effect of comparator antibody combination and F027201062 versus monospecific anti-hTNF-α and anti-hIL-6 comparator antibodies using One-way ANOVA with Tukey's correction. F027201062 was significantly more efficacious than anti-hTNF-α comparator antibody (p-value: 0.0002) and anti-hIL-6 comparator antibody (p-value: 0.0077) at equimolar doses (200 nM). There is no significant and nominal difference between F027201062 and combination of 200 nM anti-hTNF-α reference and 200 nM anti-hIL-6 reference antibody (FIG. 15, 7 donors).

6.15 Example 16: Anti-TNF-α Efficacy of Different ISVD Constructs in Human Whole Blood Assay We analysed the efficacy to block TNF-α in human whole blood, a more physiological condition. Human whole blood was stimulated with SEB to secrete endogenous TNF-α and treated with different concentrations of anti-hTNF-α reference antibody, different ISVD's and corresponding isotype controls.

In detail: blood from healthy human donors was drawn into vacutainer blood collection tubes (BD #368480) in the presence of Na-Heparin [17 IU/ml] as anti-coagulant. SEB was reconstituted as stock solution [1 mg/ml] in sterile water, and a working solution with SEB was prepared. Working solutions of the negative IgG1 control antibody, the anti-hTNF-α comparator antibody (positive control), the negative control VHH IRR00119 and the multispecific anti-TNF-α/anti-IL-6 ISVD constructs F027200926, F027201029, F027201060, F027201061 and F027201062 were prepared.

Serial dilutions of the antibodies and ISVD constructs between 13 µM to 200 nM final concentrations in medium [RPMI-1640 (from Gibco)+10% human AB-serum (from Sigma; ordering number H3667)+1% PenStrep were added in 10 µL to 96 well V-bottom microplates. 10 µl of SEB in medium was added to each well of the pre-incubation mixture of human blood with the antibodies or ISVD constructs in the 96 well plate. Finally, 80 µL of the human blood was added to each well. Samples were gently mixed, the plates were sealed with a sterile lid, and plates were incubated for 6 h at 37° C., 5% CO2, 95% rH. After incubation, 200 µl PBS were added and the blood samples were centrifuged for 15 min at 2000×g. The plasma supernatant was harvested and stored at −80° C. in a new 96 well microplate for further analyses by ELISA. Levels of MCP-1 were determined using ELISA (Invitrogen) according to the protocol provided by the manufacturer. CCL4 levels were determined using Luminex technology (R&D). The XLfit program in Speed was used for fitting the dose response curves and calculating the IC50 values in FIGS. 16 and 18 for every donor. Geomean of all 7 donors is reported. Data shown are based on 7 human blood donors.

Incubation of human whole blood with the negative control IgG1 isotype antibody or the negative control VHH IRR00119 did not lead to any inhibition of SEB-induced MCP-1 release (data not shown). In contrast, incubation of human whole blood with the monospecific anti-TNF-α monoclonal reference antibody induced a strong inhibition of SEB-induced MCP-1 release with an IC50 of 2.8 nM (FIG. 15). Incubation of human whole blood with the multispecific anti-TNF-α/anti-IL-6 ISVD construct F027201062 inhibited MCP-1 secretion to a similar extent with an IC50 of 3.2 nM. The multispecific anti-TNF-α/anti-IL-6 ISVD constructs F027200926, F027201029, F027201060, F027201061 inhibited MCP-1 release with IC50 values of 8.9 nM, 1 nM, 3.8 nM, 4.1 nM and 3.5 nM respectively (FIG. 16). IC50 values reported here are based on Geomean, while FIG. 16 shows Mean of all 7 donors.

Anti-hIL-6 comparator antibody did not induce any inhibition of MCP-1 proving the assay to be solely dependent on TNF-α. This is further strengthened by the lack of additive efficacy with anti-hTNF-α and anti-hIL-6 comparator antibodies in relation to anti-hTNF-α alone (FIG. 16).

Efficacy against TNF-α was further evaluated using a second chemokine readout, CCL4 (FIGS. 17 and 18). Analysis was focused on comparator antibodies and F027201062 as ISVD construct. Incubation of human whole blood with the monospecific anti-TNF-α monoclonal reference antibody induced a strong dose-dependent inhibition of SEB-induced CCL4 release with an IC50 of 0.96 nM (FIGS. 17 and 18). Incubation of human whole blood with the multispecific anti-TNF-α/anti-IL-6 ISVD construct F027201062 inhibited CCL4 secretion to a similar extent with an IC50 of 0.92 nM (FIGS. 17 and 18). IC50 values reported here are based on Geomean, while FIG. 18 shows Mean of all 7 donors.

Anti-hIL-6 comparator antibody did not induce any inhibition of CCL4 proving the assay to be solely dependent on TNF-α (FIG. 17). This is further strengthened by the lack of additive efficacy with anti-hTNF-α and anti-hIL-6 comparator antibodies in relation to anti-hTNF-α alone (FIGS. 17 and 18).

6.16 Example 17: IL-6 Efficacy of Different ISVD Constructs in Human Fibroblast-Like Synoviocytes from Rheumatoid Arthritis Patients We analysed the efficacy to block IL-6 in primary fibroblast-like synoviocytes from rheumatoid arthritis patients (RA-FLS). RA-FLS were stimulated with IL-17A and soluble IL-6R due to their lack of membrane-bound IL-6R. In contrast to the TF-1 proliferation assay, this FLS assay reflects thereby IL-6 trans-signalling. RA-FLS do not secrete human TNF-α, thereby the system is solely dependent on IL-6. Stimulated RA-FLS were then treated with different concentrations of anti-hIL-6 reference antibody, different ISVD's and corresponding isotype controls.

The protocol in more detail:
RA-FLS were seeded at a density of 10.000 cells/well in 96 well format in Synoviocyte Basal Medium with growth supplements (Pelobiotech). On the following day RA-FLS medium is replaced by medium with isotype controls, comparator antibodies and ISVDs in the respective concentrations (1:10 dilution, from 200 nM, 6 concentrations, duplicates). IgG1 isotype control was used as negative control for comparator antibodies, while VHH IRR00119 was used as ISVD isotype negative control. Anti-human IL-6 reference antibody was used as comparator. The following ISVD constructs were evaluated in this model: F027200926, F027201029, F027201060, F027201061 and F027201062.

Intraplate position of all constructs was varied between the duplicates to avoid plate effects. Finally, RA-FLS were stimulated with 100 ng/mi human recombinant IL-17A and 100 ng/ml sIL-6R for 24 h. After 24 h cells are centrifuged, and supernatant is collected and stored at −80° C. VEGF-A level are measured using Luminex technology. Measurements are performed in three different rheumatoid arthritis donors and for each of them in two different passages. Incubation of RA-FLS with the negative control IgG1 isotype antibody or the negative control VHH IRR00119 did not blocked IL-17A/sIL-6R induced VEGF-A secretion (data not shown). In contrast, incubation of RA-FLS with the monospecific anti-IL-6 reference antibody induced a strong dose-dependent inhibition of IL-17A/sIL-6R induced VEGF-A release with an IC50 of 0.67 nM (FIGS. 19 and 20). Incubation of RA-FLS with the multispecific anti-TNF-α/anti-IL-6 ISVD construct F027201062 inhibited VEGF-A secretion to a slightly lower extent with an IC50 of 2 nM. The multispecific anti-TNF-α/anti-IL-6 ISVD constructs F027200926, F027201029, F027201060, F027201061 inhibited VEGF-A release with IC50 values of 2 nM, 1 nM, 0.4 nM, 2.9 nM and 2.7 nM respectively (FIG. 20). IC50 values reported here are based on Geomean, while FIG. 20 shows Mean of all donors and passages.

Anti-hTNF-α comparator antibody did not induce any inhibition of VEGF-A proving the assay to be solely dependent on IL-6 (FIG. 19). This is further strengthened by the lack of additive efficacy with anti-hTNF-α and anti-hIL-6 comparator antibodies in relation to anti-IL-6 alone (FIG. 19).

6.17 Example 18: Evaluation of F027201062 in the Human TNF-α Transgenic Tg197 Polyarthritis Model F027201062 was profiled in the Tg197 mouse model of TNF-driven progressive polyarthritis (Keffer, J. et al. Transgenic mice expressing human tumour necrosis factor: a predictive genetic model of arthritis. *EMBO J* (1991) 10, 4025-4031). In these mice, a modified human TNF-α gene was inserted as a transgene into mice. The human gene was modified in a way to render the transcribed mRNA more stable, and thus led to overexpression of TNF-α and a spontaneous progressive arthritis in all four paws at 100% penetrance. Signs and symptoms became visible at about 6 weeks of age and are constantly increasing until they led to significant moribundity and mortality from about 10 weeks of age onwards if left untreated. Arthritis severity was clinically assessed by a scoring system as detailed in table 15 below.

animals of 6 weeks of age with visible signs and symptoms of arthritis (n=8 animals per group). Human IgG1 purified from human myeloma serum (BioXcell #BE0297) was used as negative control, and anti-human TNF reference mAb was used as positive control to suppress arthritis. In addition, an anti-hTNF monospecific nanobody RA15627569 was used as second positive control. F027201062 was administered at four different dose strengths of 3 mg/kg of body weight, 10 mg/kg, 30 mg/kg and 100 mg/kg respectively. Treatment was continued until 11 weeks of age. Clinical arthritis scores were determined once per week. As shown in FIG. 21, treatment with F027201062 resulted in a dose-dependent suppression of clinical arthritis scores over time. Animals treated with human IgG1 negative control antibody developed a mean arthritis score of 1.571±0.1086 by week 11. Anti-hTNFα reference mAb as well as the anti-hTNF nanobody RA15627569 suppressed arthritis progression, with a week 11 mean score of 0.5156±0.0898 and 0.2344±0.0156, respectively. Increasing doses of F027201062 reduced the arthritis progression with mean scores at week 11 of 1.203±0.0943 (3 mg/kg), 0.8214±0.161 (10 mg/kg), 0.3393±0.0592 (30 mg/kg), and 0.25±0.0579 (100 mg/kg). Statistical analysis was performed by 2-way ANOVA for time and treatment and Bonferroni-corrected groupwise comparisons were performed (FIG. 21).

Overall suppression of arthritis in the Tg197 arthritis model was analysed by Area Under the Curve (AUC, FIG. 22). Doses of F027201062 larger 3 mg/kg significantly suppressed arthritis progression to an extent comparable to

TABLE 15

Arthritis scoring system for determining arthritis phenotype severity

| ARTHRITIS SCORE[1] | CHARACTERISTICS |
|---|---|
| 0/no disease | no arthritis (normal appearance, mouse can support its weight clinging to an inverted or tilted surface such as a wire grid or a cage lid for a period of time, whole body flexibility/evasiveness normal, grip strength maximum) |
| 0.5/mild disease | onset of arthritis (mild joint swelling, all other parameters as above) |
| 1/mild to moderate disease | mild to moderate (joint distortion by swelling, inflamed paw, all other parameters as above) |
| 1.5/moderate disease | moderate arthritis (joint-paw swelling, distortion + last finger inward deformation, brief support clinging to an inverted or tilted surface such as a wire grid or a cage lid, whole body flexibility reduced, reduced grip strength) |
| 2/moderate to severe disease | moderate to severe arthritis (severe joint, paw and finger swelling, joint - leg deformation, no support clinging to an inverted or tilted surface such as a wire grid or a cage lid, no whole-body flexibility, no grip strength, climbing/feeding affected, starts shaking when trying to move, but manages to move forward) |
| 2.5/severe disease | severe arthritis (as above 2 + finger deformation in front paws, mouse movement impaired, shaking not willing to move) |
| 3/very severe disease | very severe arthritis (ankylosis detected on flexion and severely impaired movement, mouse moribund, not shaking anymore, cannot turn/flip around readily when tilted to the side). |

[1]Arthritis score as indicated on the y-axis in FIG. 21.

Arthritis was sensitive to treatment with therapeutic agents directed towards inhibition of human TNFα (Shealy, D. J. et at. Anti-TNF-alpha antibody allows healing of joint damage in polyarthritic transgenic mice. Arthritis Res 4 (2002), R7, doi:10.1186/ar430).

For the purpose of establishing dose-dependent efficacy, different doses of F027201062 were administered by twice weekly intraperitoneal injection in a therapeutic manner to anti-hTNF reference mAb as well as the anti-hTNF nanobody RA15627569 when analysed by 1-way ANOVA followed by Bonferroni-corrected groupwise comparisons.

Upon completion of treatment, hindlimb ankle joints were processed for histology and section were evaluated for structural signs of arthritis with the scoring system outlined in Table 16.

TABLE 16

Cumulative histopathological criteria for scoring arthritic phenotype in the ankle joints

| SCORE[1] | DISEASE | CRITERIA |
|---|---|---|
| 0 | Normal | no detectable pathology |
| 1 | Mild | hyperplasia of the synovial membrane and presence of polymorphonuclear infiltrates. Mild tendonitis may be present. |
| 2 | Moderate | pannus and fibrous tissue formation and focal subchondral bone erosion |
| 3 | Moderate-Severe | cartilage destruction and bone erosion |
| 4 | Severe | extensive cartilage destruction and bone erosion. Bone outline structure is lost |

[1]arthritis score as indicated on the y-axis in FIG. 23.

The results of the histology scoring are depicted in FIG. 23. Structural arthritis and joint destruction were significantly suppressed by F027201062 at higher doses.

In conclusion, the results demonstrate dose dependent suppression of arthritis signs and symptoms as well as inhibition of structural progression by the F027201062 to an extent comparable with anti-hTNF reference mAb as well as the anti-hTNF Nanobody RA15627569.

6.18 Example 19: Evaluation of F027201062 in hIL-6 Induced Haptoglobin in Vivo Model Inhibition of IL-6 In vivo was investigated in a mechanistic pharmacodynamic mouse model. Female BALB/c mice were injected with F027201062, a reference anti-hIL-6 mAb, or vehicle via the intraperitoneal route. Eight hours later, mice were injected either with PBS or with 25 μg of recombinant human IL-6. Sixteen hours later, mice were bled, and plasma was prepared. IL-6 induced acute phase reactant haptoglobin was measured in the plasma samples by fluorescent bead-coupled assay. As depicted in FIG. 24, both 1 mg/kg as well as 3 mg/kg doses of F027201062 fully suppressed IL-6-induced plasma haptoglobin, similar to the reference anti-hIL-6 mAb.

6.19 Example 20: Evaluation of F027201062 in hIL-6 Transgenic Splenomegaly Model In vivo inhibition of IL-6 was further tested in a transgenic mouse model of hIL-6 overexpression. The C.B6-Tg(H2-L-IL6)1$^{Kish/J}$ strain (Suematsu S et al., 1992: Generation of plasmacytomas with the chromosomal translocation t (12; 15) in interleukin 6 transgenic mice. Proc Natl Acad Sci USA 89(1):232-5) overexpresses human IL-6 under the control of a H-2Ld major histocompatibility promotor. At around 7 to 10 weeks of age, lymphoproliferative changes like plasmacytosis and subsequent hyperglobulinemia become apparent (Suematsu S et al., 1989: IgG1 plasmacytosis in interleukin 6 transgenic mice. Proc Natl Acad Sci USA 86(19):7547-51).

Male and female hemizygous C.B6-Tg(H2-t-IL6)1$^{Kish/j}$ mice of about 2-2.5 months of age were treated with F027201062, a reference anti-hIL-6 mAb, or a non-specific control Nanobody three times per week by intraperitoneal injection. After two weeks, mice were sacrificed and splenomegaly and hypergammaglobulinemia was determined. Non-transgenic wildtype littermate mice served as controls.

Both F027201062 as well as an anti-hIL-6 reference mAb significantly decrease splenomegaly in this model. Consistent with suppressing plasmacytosis, the plasma levels of IgG1 and IgG2a are also suppressed by F027201062 as well as anti-hIL-6 mAb treatment (FIG. 26).

6.20 Example 21: Single Dose Pharmacokinetics of F027201062 in Non-Human Primate The objective of the study was to investigate the pharmacokinetics of F027201062 after single dose administration in non-human primates. For this non-GLP study, a total of 9 male, naïve cynomolgus monkeys (Macaca fascicularis) were used. The animals were dosed according the scheme in Table 17.

TABLE 17

Dosing scheme at NHP PK study.

| Phase | Animal ID | Dose Route | Dose Level (mg/kg) | Dose Conc. (mg/mL) | Dose Volume (mL/kg) |
|---|---|---|---|---|---|
| 1 | 001M-003M | IV | 3 | 3 | 1 |
| 2 | 004M-006M | SC | 3 | 3 | 1 |
| 3 | 007M-009M | SC | 30 | 30 | 1 |

The blood was kept at room temperature to allow clotting (maximum 90 minutes) prior to centrifugation (approximately 1500 g for 10 minutes at +4° C.). The resulting serum was decanted into labelled polypropylene tubes and stored in a freezer set to ≤−65° C. The samples were measured using a non-validated generic ELISA method developed.

The pharmacokinetic profiles are given in FIG. 27. After IV administration, the clearance was 0.273 t/h/kg and volume of distribution (Vss) 0.0464 L/kg. The pharmacokinetics were affected by ADA. All pre-dose naïve, ADA-negative animals were tested positive at 360 h and 672 h.

7 INDUSTRIAL APPLICABILITY

The polypeptides, nucleic acid molecules encoding the same, vectors comprising the nucleic acids and compositions described herein may be used for example in the treatment of subjects suffering from inflammatory and/or autoimmune diseases.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A polypeptide, or a composition comprising the polypeptide, wherein the polypeptide comprises at least three immunoglobulin single variable domains (ISVDs), wherein each of said ISVDs comprises three complementarity determining regions (CDR1 to CDR3, respectively), optionally linked via one or more peptidic linkers; and wherein:
   a) a first ISVD binds to IL-6 and comprises
      i. a CDR1 which has the amino acid sequence of SEQ ID NO: 6;
      ii. a CDR2 which has the amino acid sequence of SEQ ID NO: 10 amino acid difference(s) with SEQ ID NO: 10; and
      iii. a CDR3 which has the amino acid sequence of SEQ ID NO: 14;
   b) a second ISVD binds to IL-6 and comprises;
      iv. a CDR1 which has the amino acid sequence of SEQ ID NO: 8
      v. a CDR2 which has the amino acid sequence of SEQ ID NO: 12 amino acid difference(s) with SEQ ID NO: 12; and
      vi. a CDR3 which has the amino acid sequence of SEQ ID NO: 16; and
   c) a third ISVD binds to TNF-α and comprises
      vii. a CDR1 which has the amino acid sequence of SEQ ID NO: 9;
      viii. a CDR2 which has the amino acid sequence of SEQ ID NO: 13 amino acid difference(s) with SEQ ID NO: 13; and
      ix. a CDR3 which has the amino acid sequence of SEQ ID NO: 17.

2. The polypeptide or composition according to claim 1, which is a pharmaceutical composition which further comprises at least one pharmaceutically acceptable carrier, diluent or excipient and/or adjuvant, and optionally comprises one or more further polypeptides and/or compounds.

3. The polypeptide or composition according to claim 1, wherein the polypeptide consists of three ISVDs, wherein:
   a) said first ISVD comprises a CDR1 having the amino acid sequence of SEQ ID NO:6, a CDR2 having the amino acid sequence of SEQ ID NO: 10 and a CDR3 having the amino acid sequence of SEQ ID NO: 14;
   b) said second ISVD comprises a CDR1 having the amino acid sequence of SEQ ID NO:8, a CDR2 having the amino acid sequence of SEQ ID NO: 12 and a CDR3 having the amino acid sequence of SEQ ID NO: 16; and
   c) said third ISVD comprises a CDR1 having the amino acid sequence of SEQ ID NO:9, a CDR2 having the amino acid sequence of SEQ ID NO: 13 and a CDR3 having the amino acid sequence of SEQ ID NO: 17.

4. The polypeptide or composition according to claim 1, wherein:

a) the amino acid sequence of said first ISVD has a sequence identity of more than 90% with SEQ ID NO: 2;
b) the amino acid sequence of said second ISVD has a sequence identity of more than 90% with SEQ ID NO: 4; and
c) the amino acid sequence of said third ISVD has a sequence identity of more than 90% identity with SEQ ID NO: 5.

5. The polypeptide or composition according to claim 1, wherein:
   a) said first ISVD has the amino acid sequence of SEQ ID NO: 2;
   b) said second ISVD has the amino acid sequence of SEQ ID NO: 4; and
   c) said third ISVD has the amino acid sequence of SEQ ID NO: 5.

6. The polypeptide or composition according to claim 1, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

7. The polypeptide or composition according to claim 6, in which said one or more other groups, residues, moieties or binding units that provide the polypeptide with increased half-life is chosen from the group consisting of binding units that can bind to serum albumin or and binding units that can bind to a serum immunoglobulin.

8. The polypeptide or composition according to claim 7, wherein the binding units that can bind to serum albumin are binding units that can bind to human serum albumin.

9. The polypeptide or composition according to claim 7, wherein the binding units that can bind to a serum immunoglobulin are binding units that can bind to IgG.

10. The polypeptide or composition according to claim 7, in which said binding unit that provides the polypeptide with increased half-life is an ISVD that can bind to human serum albumin.

11. The polypeptide or composition according to claim 10, wherein the ISVD binding to human serum albumin comprises
   i. a CDR1 which has the amino acid sequence of SEQ ID NO: 7 amino;
   ii. a CDR2 which has the amino acid sequence of SEQ ID NO: 11; and
   iii. a CDR3 which has the amino acid sequence of SEQ ID NO: 15.

12. The polypeptide or composition according to claim 11, wherein the amino acid sequence of said ISVD binding to human serum albumin has a sequence identity of more than 90% with SEQ ID NO: 3.

13. The polypeptide or composition according to claim 1, wherein the polypeptide comprises or consists of an amino acid sequence having a sequence identity of more than 90% with SEQ ID NO: 1.

14. A nucleic acid comprising a nucleotide sequence that encodes a polypeptide according to claim 1.

15. A non-human host or host cell comprising a nucleic acid according to claim 14.

16. A method for producing a polypeptide, said method at least comprising the steps of:
   a) expressing a nucleic acid according to claim 14; optionally followed by:
   b) isolating and/or purifying the polypeptide.

17. A method of treating an inflammatory and/or autoimmune disease, wherein said method comprises administering, to a subject in need thereof, an effective amount of a polypeptide according to claim 1.

18. The method according to claim 17, wherein the inflammatory and/or autoimmune disease is rheumatoid arthritis.

* * * * *

UNITED STATES PATENT AND TRADEMARK OFFICE
CERTIFICATE OF CORRECTION

PATENT NO. : 11,897,951 B2
APPLICATION NO. : 17/553916
DATED : February 13, 2024
INVENTOR(S) : Heidi Rommelaere et al.

It is certified that error appears in the above-identified patent and that said Letters Patent is hereby corrected as shown below:

In the Claims

In Claim 1, at Column 159, Lines 52-54:
"ii. a CDR2 which has the amino acid sequence of SEQ
 ID NO: 10 amino acid difference(s) with SEQ ID
 NO: 10; and"

Should read:
--ii. a CDR2 which has the amino acid sequence of SEQ
 ID NO: 10; and--

In Claim 1, at Column 159, Lines 57-62:
"b) a second ISVD binds to IL-6 and comprises;
 iv. a CDR1 which has the amino acid sequence of SEQ
  ID NO: 8
 v. a CDR2 which has the amino acid sequence of SEQ
  ID NO: 12 amino acid difference(s) with SEQ ID
  NO: 12; and"

Should read:
--b) a second ISVD binds to IL-6 and comprises
 iv. a CDR1 which has the amino acid sequence of SEQ
  ID NO: 8;
 v. a CDR2 which has the amino acid sequence of SEQ
  ID NO: 12; and--

In Claim 1, at Column 160, Lines 42-44:
"viii. a CDR2 which has the amino acid sequence of
 SEQ ID NO: 13 amino acid difference(s) with SEQ
 ID NO: 13; and"

Signed and Sealed this
Twenty-third Day of April, 2024

Katherine Kelly Vidal
*Director of the United States Patent and Trademark Office*

CERTIFICATE OF CORRECTION (continued)
U.S. Pat. No. 11,897,951 B2

Should read:
--viii. a CDR2 which has the amino acid sequence of
   SEQ ID NO: 13; and--

In Claim 7, at Column 161, Lines 31-32:
"that can bind to serum albumin or and binding units that can bind to a serum immunoglobulin."

Should read:
--that can bind to serum albumin and binding units that can bind to a serum immunoglobulin.--

In Claim 11, at Column 162, Lines 8-9:
"i. a CDR1 which has the amino acid sequence of SEQ ID
   NO: 7 amino;"

Should read:
--i. a CDR1 which has the amino acid sequence of SEQ ID
   NO: 7;--

SEQUENCE LISTING

<160> NUMBER OF SEQ ID NOS: 177

<210> SEQ ID NO 1
<211> LENGTH: 516
<212> TYPE: PRT
<213> ORGANISM: Artificial Sequence
<220> FEATURE:
<223> OTHER INFORMATION: F027201062

<400> SEQUENCE: 1

```
Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Asn Tyr
            20                  25                  30

Ala Met Ala Trp Phe Arg Gln Ala Pro Gly Lys Glu Arg Glu Phe Val
        35                  40                  45

Ala Val Ile Ser Tyr Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Val Asp Ser Pro Leu Ile Ala Thr His Pro Arg Gly Tyr Asp
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Val
    130                 135                 140

Val Gln Pro Gly Gly Ser Leu Arg Leu Ser Cys Ala Ala Ser Gly Phe
145                 150                 155                 160

Thr Phe Arg Ser Phe Gly Met Ser Trp Val Arg Gln Ala Pro Gly Lys
                165                 170                 175

Gly Pro Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ser
        195                 200                 205

Lys Asn Thr Leu Tyr Leu Gln Met Asn Ser Leu Arg Pro Glu Asp Thr
    210                 215                 220

Ala Leu Tyr Tyr Cys Thr Ile Gly Gly Ser Leu Ser Arg Ser Ser Gln
225                 230                 235                 240

Gly Thr Leu Val Thr Val Ser Ser Gly Gly Gly Ser Gly Gly Gly
                245                 250                 255

Ser Glu Val Gln Leu Val Glu Ser Gly Gly Gly Val Val Gln Pro Gly
            260                 265                 270

Gly Ser Leu Arg Leu Ser Cys Ala Ala Ser Gly Phe Thr Leu Ala Tyr
        275                 280                 285

Tyr Ala Ile Gly Trp Phe Arg Gln Ala Pro Gly Lys Glu Arg Glu Gly
    290                 295                 300

Val Ser Cys Ile Ser Gly Ser Val Gly Thr Thr Tyr Ala Asp Ser
305                 310                 315                 320

Val Lys Gly Arg Phe Thr Ile Ser Arg Asp Asn Ala Lys Asn Thr Val
                325                 330                 335

Tyr Leu Gln Met Asn Ser Leu Arg Pro Glu Asp Thr Ala Leu Tyr Tyr
            340                 345                 350

Cys Val Arg Ser Ser Trp Phe Asp Cys Gly Val Gln Gly Arg Asp Leu
```

```
                355                 360                 365
Gly Asn Glu Tyr Asp Tyr Arg Gly Gln Gly Thr Leu Val Thr Val Ser
370                 375                 380

Ser Gly Gly Gly Gly Ser Gly Gly Ser Glu Val Gln Leu Val Glu
385                 390                 395                 400

Ser Gly Gly Gly Val Val Gln Pro Gly Gly Ser Leu Arg Leu Ser Cys
                405                 410                 415

Thr Ala Ser Gly Phe Thr Phe Ser Thr Ala Asp Met Gly Trp Phe Arg
                420                 425                 430

Gln Ala Pro Gly Lys Gly Arg Glu Phe Val Ala Arg Ile Ser Gly Ile
                435                 440                 445

Asp Gly Thr Thr Tyr Tyr Asp Glu Pro Val Lys Gly Arg Phe Thr Ile
                450                 455                 460

Ser Arg Asp Asn Ser Lys Asn Thr Val Tyr Leu Gln Met Asn Ser Leu
465                 470                 475                 480

Arg Pro Glu Asp Thr Ala Leu Tyr Tyr Cys Arg Ser Pro Arg Tyr Ala
                485                 490                 495

Asp Gln Trp Ser Ala Tyr Asp Tyr Trp Gly Gln Gly Thr Leu Val Lys
                500                 505                 510

Val Ser Ser Ala
        515

<210> SEQ ID NO 2
<211> LENGTH: 124
<212> TYPE: PRT
<213> ORGANISM: Artificial Sequence
<220> FEATURE:
<223> OTHER INFORMATION: 17C04

<400> SEQUENCE: 2

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Asn Tyr
                20                  25                  30

Ala Met Ala Trp Phe Arg Gln Ala Pro Gly Lys Glu Arg Glu Phe Val
            35                  40                  45

Ala Val Ile Ser Tyr Ala Gly Gly Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Val Asp Ser Pro Leu Ile Ala Thr His Pro Arg Gly Tyr Asp
                100                 105                 110

Tyr Trp Gly Gln Gly Thr Leu Val Thr Val Ser Ser
            115                 120

<210> SEQ ID NO 3
<211> LENGTH: 115
<212> TYPE: PRT
<213> ORGANISM: Artificial Sequence
<220> FEATURE:
<223> OTHER INFORMATION: ALB23002

<400> SEQUENCE: 3

Glu Val Gln Leu Val Glu Ser Gly Gly Gly Val Val Gln Pro Gly Gly
1               5                   10                  15
```

```
Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 4
<211> LENGTH: 128
<212> TYPE: PRT
<213> ORGANISM: Artificial Sequence
<220> FEATURE:
<223> OTHER INFORMATION: 6B12

<400> SEQUENCE: 4

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Leu Ala Tyr Tyr
            20                  25                  30

Ala Ile Gly Trp Phe Arg Gln Ala Pro Gly Lys Glu Arg Glu Gly Val
        35                  40                  45

Ser Cys Ile Ser Gly Ser Val Gly Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Leu Tyr Tyr Cys
                85                  90                  95

Val Arg Ser Ser Trp Phe Asp Cys Gly Val Gly Arg Asp Leu Gly
            100                 105                 110

Asn Glu Tyr Asp Tyr Arg Gly Gln Gly Thr Leu Val Thr Val Ser Ser
            115                 120                 125

<210> SEQ ID NO 5
<211> LENGTH: 121
<212> TYPE: PRT
<213> ORGANISM: Artificial Sequence
<220> FEATURE:
<223> OTHER INFORMATION: 6C11

<400> SEQUENCE: 5

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Asn Ser Lys Asn Thr Val Tyr
65                  70                  75                  80
```

```
Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Lys Val Ser Ser
        115                 120

<210> SEQ ID NO 6
<211> LENGTH: 10
<212> TYPE: PRT
<213> ORGANISM: Artificial Sequence
<220> FEATURE:
<223> OTHER INFORMATION: CDR1

<400> SEQUENCE: 6

Gly Arg Thr Phe Ser Asn Tyr Ala Met Ala
1               5                   10

<210> SEQ ID NO 7
<211> LENGTH: 10
<212> TYPE: PRT
<213> ORGANISM: Artificial Sequence
<220> FEATURE:
<223> OTHER INFORMATION: CDR1

<400> SEQUENCE: 7

Gly Phe Thr Phe Arg Ser Phe Gly Met Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: CDR1

<400> SEQUENCE: 8

Gly Phe Thr Leu Ala Tyr Tyr Ala Ile Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: CDR1

<400> SEQUENCE: 9

Gly Phe Thr Phe Ser Thr Ala Asp Met Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: CDR2

<400> SEQUENCE: 10

Val Ile Ser Tyr Ala Gly Gly Arg Thr Tyr
1               5                   10

<210> SEQ ID NO 11
<211> LENGTH: 10
<212> TYPE: PRT
```

<213> ORGANISM: Artificial Sequence
<220> FEATURE:
<223> OTHER INFORMATION: CDR2

<400> SEQUENCE: 11

Ser Ile Ser Gly Ser Gly Ser Asp Thr Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: CDR2

<400> SEQUENCE: 12

Cys Ile Ser Gly Ser Val Gly Thr Thr Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: CDR2

<400> SEQUENCE: 13

Arg Ile Ser Gly Ile Asp Gly Thr Thr Tyr
1               5                   10

<210> SEQ ID NO 14
<211> LENGTH: 15
<212> TYPE: PRT
<213> ORGANISM: Artificial Sequence
<220> FEATURE:
<223> OTHER INFORMATION: CDR3

<400> SEQUENCE: 14

Val Asp Ser Pro Leu Ile Ala Thr His Pro Arg Gly Tyr Asp Tyr
1               5                   10                  15

<210> SEQ ID NO 15
<211> LENGTH: 6
<212> TYPE: PRT
<213> ORGANISM: Artificial Sequence
<220> FEATURE:
<223> OTHER INFORMATION: CDR3

<400> SEQUENCE: 15

Gly Gly Ser Leu Ser Arg
1               5

<210> SEQ ID NO 16
<211> LENGTH: 19
<212> TYPE: PRT
<213> ORGANISM: Artificial Sequence
<220> FEATURE:
<223> OTHER INFORMATION: CDR3

<400> SEQUENCE: 16

Ser Ser Trp Phe Asp Cys Gly Val Gln Gly Arg Asp Leu Gly Asn Glu
1               5                   10                  15

Tyr Asp Tyr

<210> SEQ ID NO 17
<211> LENGTH: 12

```
<212> TYPE: PRT
<213> ORGANISM: Artificial Sequence
<220> FEATURE:
<223> OTHER INFORMATION: CDR3

<400> SEQUENCE: 17

Pro Arg Tyr Ala Asp Gln Trp Ser Ala Tyr Asp Tyr
1               5                   10

<210> SEQ ID NO 18
<211> LENGTH: 25
<212> TYPE: PRT
<213> ORGANISM: Artificial Sequence
<220> FEATURE:
<223> OTHER INFORMATION: FR1

<400> SEQUENCE: 18

Asp Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 19
<211> LENGTH: 25
<212> TYPE: PRT
<213> ORGANISM: Artificial Sequence
<220> FEATURE:
<223> OTHER INFORMATION: FR1

<400> SEQUENCE: 19

Glu Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: FR1

<400> SEQUENCE: 20

Glu Val Gln Leu Val Glu Ser Gly Gly Gly Val Val Gln Pro Gly Gly
1               5                   10                  15

Ser Leu Arg Leu Ser Cys Thr Ala Ser
            20                  25

<210> SEQ ID NO 21
<211> LENGTH: 14
<212> TYPE: PRT
<213> ORGANISM: Artificial Sequence
<220> FEATURE:
<223> OTHER INFORMATION: FR2

<400> SEQUENCE: 21

Trp Phe Arg Gln Ala Pro Gly Lys Glu Arg Glu Phe Val Ala
1               5                   10

<210> SEQ ID NO 22
<211> LENGTH: 14
<212> TYPE: PRT
<213> ORGANISM: Artificial Sequence
<220> FEATURE:
<223> OTHER INFORMATION: FR2
```

-continued

<400> SEQUENCE: 22

Trp Val Arg Gln Ala Pro Gly Lys Gly Pro Glu Trp Val Ser
1               5                   10

<210> SEQ ID NO 23
<211> LENGTH: 14
<212> TYPE: PRT
<213> ORGANISM: Artificial Sequence
<220> FEATURE:
<223> OTHER INFORMATION: FR2

<400> SEQUENCE: 23

Trp Phe Arg Gln Ala Pro Gly Lys Glu Arg Glu Gly Val Ser
1               5                   10

<210> SEQ ID NO 24
<211> LENGTH: 14
<212> TYPE: PRT
<213> ORGANISM: Artificial Sequence
<220> FEATURE:
<223> OTHER INFORMATION: FR2

<400> SEQUENCE: 24

Trp Phe Arg Gln Ala Pro Gly Lys Gly Arg Glu Phe Val Ala
1               5                   10

<210> SEQ ID NO 25
<211> LENGTH: 39
<212> TYPE: PRT
<213> ORGANISM: Artificial Sequence
<220> FEATURE:
<223> OTHER INFORMATION: FR3

<400> SEQUENCE: 25

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Arg Pro Glu Asp Thr
                20                  25                  30

Ala Leu Tyr Tyr Cys Ala Ala
        35

<210> SEQ ID NO 26
<211> LENGTH: 39
<212> TYPE: PRT
<213> ORGANISM: Artificial Sequence
<220> FEATURE:
<223> OTHER INFORMATION: FR3

<400> SEQUENCE: 26

Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Pro Glu Asp Thr
                20                  25                  30

Ala Leu Tyr Tyr Cys Thr Ile
        35

<210> SEQ ID NO 27
<211> LENGTH: 39
<212> TYPE: PRT
<213> ORGANISM: Artificial Sequence
<220> FEATURE:
<223> OTHER INFORMATION: FR3

<400> SEQUENCE: 27

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Arg Pro Glu Asp Thr
            20                  25                  30

Ala Leu Tyr Tyr Cys Val Arg
        35

<210> SEQ ID NO 28
<211> LENGTH: 39
<212> TYPE: PRT
<213> ORGANISM: Artificial Sequence
<220> FEATURE:
<223> OTHER INFORMATION: FR3

<400> SEQUENCE: 28

Tyr Asp Glu Pro Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Arg Ser
        35

<210> SEQ ID NO 29
<211> LENGTH: 11
<212> TYPE: PRT
<213> ORGANISM: Artificial Sequence
<220> FEATURE:
<223> OTHER INFORMATION: FR4

<400> SEQUENCE: 29

Trp Gly Gln Gly Thr Leu Val Thr Val Ser Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: FR4

<400> SEQUENCE: 30

Ser Ser Gln Gly Thr Leu Val Thr Val Ser Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: FR4

<400> SEQUENCE: 31

Arg Gly Gln Gly Thr Leu Val Thr Val Ser Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: FR4

<400> SEQUENCE: 32

Trp Gly Gln Gly Thr Leu Val Lys Val Ser Ser
1               5                   10

```
<210> SEQ ID NO 33
<211> LENGTH: 5
<212> TYPE: PRT
<213> ORGANISM: Artificial Sequence
<220> FEATURE:
<223> OTHER INFORMATION: CDR1

<400> SEQUENCE: 33

Asn Tyr Ala Met Ala
1               5

<210> SEQ ID NO 34
<211> LENGTH: 5
<212> TYPE: PRT
<213> ORGANISM: Artificial Sequence
<220> FEATURE:
<223> OTHER INFORMATION: CDR1

<400> SEQUENCE: 34

Ser Phe Gly Met Ser
1               5

<210> SEQ ID NO 35
<211> LENGTH: 5
<212> TYPE: PRT
<213> ORGANISM: Artificial Sequence
<220> FEATURE:
<223> OTHER INFORMATION: CDR1

<400> SEQUENCE: 35

Tyr Tyr Ala Ile Gly
1               5

<210> SEQ ID NO 36
<211> LENGTH: 5
<212> TYPE: PRT
<213> ORGANISM: Artificial Sequence
<220> FEATURE:
<223> OTHER INFORMATION: CDR1

<400> SEQUENCE: 36

Thr Ala Asp Met Gly
1               5

<210> SEQ ID NO 37
<211> LENGTH: 17
<212> TYPE: PRT
<213> ORGANISM: Artificial Sequence
<220> FEATURE:
<223> OTHER INFORMATION: CDR2

<400> SEQUENCE: 37

Val Ile Ser Tyr Ala Gly Gly Arg Thr Tyr Tyr Ala Asp Ser Val Lys
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: CDR2

<400> SEQUENCE: 38

Ser Ile Ser Gly Ser Gly Ser Asp Thr Leu Tyr Ala Asp Ser Val Lys
```

```
1               5                   10                  15
Gly

<210> SEQ ID NO 39
<211> LENGTH: 17
<212> TYPE: PRT
<213> ORGANISM: Artificial Sequence
<220> FEATURE:
<223> OTHER INFORMATION: CDR2

<400> SEQUENCE: 39

Cys Ile Ser Gly Ser Val Gly Thr Thr Tyr Tyr Ala Asp Ser Val Lys
1               5                   10                  15
Gly

<210> SEQ ID NO 40
<211> LENGTH: 17
<212> TYPE: PRT
<213> ORGANISM: Artificial Sequence
<220> FEATURE:
<223> OTHER INFORMATION: CDR2

<400> SEQUENCE: 40

Arg Ile Ser Gly Ile Asp Gly Thr Thr Tyr Tyr Asp Glu Pro Val Lys
1               5                   10                  15
Gly

<210> SEQ ID NO 41
<211> LENGTH: 30
<212> TYPE: PRT
<213> ORGANISM: Artificial Sequence
<220> FEATURE:
<223> OTHER INFORMATION: FR1

<400> SEQUENCE: 41

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: FR1

<400> SEQUENCE: 42

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: FR1

<400> SEQUENCE: 43

Glu Val Gln Leu Val Glu Ser Gly Gly Gly Val Val Gln Pro Gly Gly
1               5                   10                  15
```

Ser Leu Arg Leu Ser Cys Ala Ala Ser Gly Phe Thr Leu Ala
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: FR1

<400> SEQUENCE: 44

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: FR3

<400> SEQUENCE: 45

Arg Phe Thr Ile Ser Arg Asp Asn Ala Lys Asn Thr Val Tyr Leu Gln
1               5                   10                  15

Met Asn Ser Leu Arg Pro Glu Asp Thr Ala Leu Tyr Tyr Cys Ala Ala
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: FR3

<400> SEQUENCE: 46

Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Leu Tyr Tyr Cys Thr Ile
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: FR3

<400> SEQUENCE: 47

Arg Phe Thr Ile Ser Arg Asp Asn Ala Lys Asn Thr Val Tyr Leu Gln
1               5                   10                  15

Met Asn Ser Leu Arg Pro Glu Asp Thr Ala Leu Tyr Tyr Cys Val Arg
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: FR3

<400> SEQUENCE: 48

Arg Phe Thr Ile Ser Arg Asp Asn Ser Lys Asn Thr Val Tyr Leu Gln
1               5                   10                  15

```
Met Asn Ser Leu Arg Pro Glu Asp Thr Ala Leu Tyr Tyr Cys Arg Ser
            20                  25                  30

<210> SEQ ID NO 49
<211> LENGTH: 4
<212> TYPE: PRT
<213> ORGANISM: Artificial Sequence
<220> FEATURE:
<223> OTHER INFORMATION: Motif from Table X

<400> SEQUENCE: 49

Gly Leu Glu Trp
1

<210> SEQ ID NO 50
<211> LENGTH: 115
<212> TYPE: PRT
<213> ORGANISM: Artificial Sequence
<220> FEATURE:
<223> OTHER INFORMATION: Alb8

<400> SEQUENCE: 50

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 51
<211> LENGTH: 115
<212> TYPE: PRT
<213> ORGANISM: Artificial Sequence
<220> FEATURE:
<223> OTHER INFORMATION: Alb23

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95
```

```
Thr Ile Gly Gly Ser Leu Ser Arg Ser Ser Gln Gly Thr Leu Val Thr
            100                 105                 110

Val Ser Ser
        115

<210> SEQ ID NO 52
<211> LENGTH: 116
<212> TYPE: PRT
<213> ORGANISM: Artificial Sequence
<220> FEATURE:
<223> OTHER INFORMATION: Alb129

<400> SEQUENCE: 52

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 53
<211> LENGTH: 116
<212> TYPE: PRT
<213> ORGANISM: Artificial Sequence
<220> FEATURE:
<223> OTHER INFORMATION: Alb132

<400> SEQUENCE: 53

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 54
<211> LENGTH: 115
<212> TYPE: PRT
<213> ORGANISM: Artificial Sequence
```

<220> FEATURE:
<223> OTHER INFORMATION: Alb11

<400> SEQUENCE: 54

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 55
<211> LENGTH: 116
<212> TYPE: PRT
<213> ORGANISM: Artificial Sequence
<220> FEATURE:
<223> OTHER INFORMATION: Alb11 (S112K)-A

<400> SEQUENCE: 55

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 56
<211> LENGTH: 115
<212> TYPE: PRT
<213> ORGANISM: Artificial Sequence
<220> FEATURE:
<223> OTHER INFORMATION: Alb82

<400> SEQUENCE: 56

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

```
Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
                100                 105                 110

Val Ser Ser
        115

<210> SEQ ID NO 57
<211> LENGTH: 116
<212> TYPE: PRT
<213> ORGANISM: Artificial Sequence
<220> FEATURE:
<223> OTHER INFORMATION: Alb82-A

<400> SEQUENCE: 57

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
                100                 105                 110

Val Ser Ser Ala
        115

<210> SEQ ID NO 58
<211> LENGTH: 117
<212> TYPE: PRT
<213> ORGANISM: Artificial Sequence
<220> FEATURE:
<223> OTHER INFORMATION: Alb82-AA

<400> SEQUENCE: 58

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95
```

```
Thr Ile Gly Gly Ser Leu Ser Arg Ser Ser Gln Gly Thr Leu Val Thr
            100                 105                 110

Val Ser Ser Ala Ala
        115

<210> SEQ ID NO 59
<211> LENGTH: 118
<212> TYPE: PRT
<213> ORGANISM: Artificial Sequence
<220> FEATURE:
<223> OTHER INFORMATION: Alb82-AAA

<400> SEQUENCE: 59

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 60
<211> LENGTH: 116
<212> TYPE: PRT
<213> ORGANISM: Artificial Sequence
<220> FEATURE:
<223> OTHER INFORMATION: Alb82-G

<400> SEQUENCE: 60

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 61
<211> LENGTH: 117
<212> TYPE: PRT
```

<213> ORGANISM: Artificial Sequence
<220> FEATURE:
<223> OTHER INFORMATION: Alb82-GG

<400> SEQUENCE: 61

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115

<210> SEQ ID NO 62
<211> LENGTH: 118
<212> TYPE: PRT
<213> ORGANISM: Artificial Sequence
<220> FEATURE:
<223> OTHER INFORMATION: Alb82-GGG

<400> SEQUENCE: 62

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115

<210> SEQ ID NO 63
<211> LENGTH: 116
<212> TYPE: PRT
<213> ORGANISM: Artificial Sequence
<220> FEATURE:
<223> OTHER INFORMATION: Alb223

<400> SEQUENCE: 63

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 64
<211> LENGTH: 3
<212> TYPE: PRT
<213> ORGANISM: Artificial Sequence
<220> FEATURE:
<223> OTHER INFORMATION: linker

<400> SEQUENCE: 64

Ala Ala Ala
1

<210> SEQ ID NO 65
<211> LENGTH: 5
<212> TYPE: PRT
<213> ORGANISM: Artificial Sequence
<220> FEATURE:
<223> OTHER INFORMATION: linker

<400> SEQUENCE: 65

Gly Gly Gly Gly Ser
1               5

<210> SEQ ID NO 66
<211> LENGTH: 7
<212> TYPE: PRT
<213> ORGANISM: Artificial Sequence
<220> FEATURE:
<223> OTHER INFORMATION: linker

<400> SEQUENCE: 66

Ser Gly Gly Ser Gly Gly Ser
1               5

<210> SEQ ID NO 67
<211> LENGTH: 8
<212> TYPE: PRT
<213> ORGANISM: Artificial Sequence
<220> FEATURE:
<223> OTHER INFORMATION: linker

<400> SEQUENCE: 67

Gly Gly Gly Gly Ser Gly Gly Ser
1               5

<210> SEQ ID NO 68
<211> LENGTH: 9
<212> TYPE: PRT
<213> ORGANISM: Artificial Sequence
<220> FEATURE:
<223> OTHER INFORMATION: linker

```
<400> SEQUENCE: 68

Gly Gly Gly Gly Ser Gly Gly Gly Ser
1               5

<210> SEQ ID NO 69
<211> LENGTH: 10
<212> TYPE: PRT
<213> ORGANISM: Artificial Sequence
<220> FEATURE:
<223> OTHER INFORMATION: linker

<400> SEQUENCE: 69

Gly Gly Gly Gly Ser Gly Gly Gly Gly Ser
1               5                   10

<210> SEQ ID NO 70
<211> LENGTH: 15
<212> TYPE: PRT
<213> ORGANISM: Artificial Sequence
<220> FEATURE:
<223> OTHER INFORMATION: linker

<400> SEQUENCE: 70

Gly Gly Gly Gly Ser Gly Gly Gly Gly Ser Gly Gly Gly Gly Ser
1               5                   10                  15

<210> SEQ ID NO 71
<211> LENGTH: 18
<212> TYPE: PRT
<213> ORGANISM: Artificial Sequence
<220> FEATURE:
<223> OTHER INFORMATION: linker

<400> SEQUENCE: 71

Gly Gly Gly Gly Ser Gly Gly Gly Gly Ser Gly Gly Gly Gly Ser Gly
1               5                   10                  15

Gly Ser

<210> SEQ ID NO 72
<211> LENGTH: 20
<212> TYPE: PRT
<213> ORGANISM: Artificial Sequence
<220> FEATURE:
<223> OTHER INFORMATION: linker

<400> SEQUENCE: 72

Gly Gly Gly Gly Ser Gly Gly Gly Gly Ser Gly Gly Gly Gly Ser Gly
1               5                   10                  15

Gly Gly Gly Ser
            20

<210> SEQ ID NO 73
<211> LENGTH: 25
<212> TYPE: PRT
<213> ORGANISM: Artificial Sequence
<220> FEATURE:
<223> OTHER INFORMATION: linker

<400> SEQUENCE: 73

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 74
<211> LENGTH: 30
<212> TYPE: PRT
<213> ORGANISM: Artificial Sequence
<220> FEATURE:
<223> OTHER INFORMATION: linker

<400> SEQUENCE: 74

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 75
<211> LENGTH: 35
<212> TYPE: PRT
<213> ORGANISM: Artificial Sequence
<220> FEATURE:
<223> OTHER INFORMATION: linker

<400> SEQUENCE: 75

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 76
<211> LENGTH: 40
<212> TYPE: PRT
<213> ORGANISM: Artificial Sequence
<220> FEATURE:
<223> OTHER INFORMATION: linker

<400> SEQUENCE: 76

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 77
<211> LENGTH: 15
<212> TYPE: PRT
<213> ORGANISM: Artificial Sequence
<220> FEATURE:
<223> OTHER INFORMATION: linker

<400> SEQUENCE: 77

Glu Pro Lys Ser Cys Asp Lys Thr His Thr Cys Pro Pro Cys Pro
1               5                   10                  15

<210> SEQ ID NO 78
<211> LENGTH: 24
<212> TYPE: PRT
<213> ORGANISM: Artificial Sequence
<220> FEATURE:
<223> OTHER INFORMATION: linker

<400> SEQUENCE: 78

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 79
<211> LENGTH: 12
<212> TYPE: PRT
<213> ORGANISM: Artificial Sequence
<220> FEATURE:
<223> OTHER INFORMATION: linker

<400> SEQUENCE: 79

Glu Pro Lys Thr Pro Lys Pro Gln Pro Ala Ala Ala
1               5                   10

<210> SEQ ID NO 80
<211> LENGTH: 62
<212> TYPE: PRT
<213> ORGANISM: Artificial Sequence
<220> FEATURE:
<223> OTHER INFORMATION: linker

<400> SEQUENCE: 80

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 81
<211> LENGTH: 5
<212> TYPE: PRT
<213> ORGANISM: Artificial Sequence
<220> FEATURE:
<223> OTHER INFORMATION: C-terminus

<400> SEQUENCE: 81

Val Thr Val Ser Ser
1               5

<210> SEQ ID NO 82
<211> LENGTH: 5
<212> TYPE: PRT
<213> ORGANISM: Artificial Sequence
<220> FEATURE:
<223> OTHER INFORMATION: C-terminus

<400> SEQUENCE: 82

Val Lys Val Ser Ser
1               5

<210> SEQ ID NO 83
<211> LENGTH: 5
<212> TYPE: PRT
<213> ORGANISM: Artificial Sequence
<220> FEATURE:
<223> OTHER INFORMATION: C-terminus

<400> SEQUENCE: 83

Val Gln Val Ser Ser
1               5

<210> SEQ ID NO 84

```
<211> LENGTH: 5
<212> TYPE: PRT
<213> ORGANISM: Artificial Sequence
<220> FEATURE:
<223> OTHER INFORMATION: C-terminus

<400> SEQUENCE: 84

Val Thr Val Lys Ser
1               5

<210> SEQ ID NO 85
<211> LENGTH: 5
<212> TYPE: PRT
<213> ORGANISM: Artificial Sequence
<220> FEATURE:
<223> OTHER INFORMATION: C-terminus

<400> SEQUENCE: 85

Val Thr Val Gln Ser
1               5

<210> SEQ ID NO 86
<211> LENGTH: 5
<212> TYPE: PRT
<213> ORGANISM: Artificial Sequence
<220> FEATURE:
<223> OTHER INFORMATION: C-terminus

<400> SEQUENCE: 86

Val Lys Val Lys Ser
1               5

<210> SEQ ID NO 87
<211> LENGTH: 5
<212> TYPE: PRT
<213> ORGANISM: Artificial Sequence
<220> FEATURE:
<223> OTHER INFORMATION: C-terminus

<400> SEQUENCE: 87

Val Lys Val Gln Ser
1               5

<210> SEQ ID NO 88
<211> LENGTH: 5
<212> TYPE: PRT
<213> ORGANISM: Artificial Sequence
<220> FEATURE:
<223> OTHER INFORMATION: C-terminus

<400> SEQUENCE: 88

Val Gln Val Lys Ser
1               5

<210> SEQ ID NO 89
<211> LENGTH: 5
<212> TYPE: PRT
<213> ORGANISM: Artificial Sequence
<220> FEATURE:
<223> OTHER INFORMATION: C-terminus

<400> SEQUENCE: 89

Val Gln Val Gln Ser
1               5

<210> SEQ ID NO 90
<211> LENGTH: 6
```

```
<212> TYPE: PRT
<213> ORGANISM: Artificial Sequence
<220> FEATURE:
<223> OTHER INFORMATION: C-terminus

<400> SEQUENCE: 90

Val Thr Val Ser Ser Ala
1               5

<210> SEQ ID NO 91
<211> LENGTH: 6
<212> TYPE: PRT
<213> ORGANISM: Artificial Sequence
<220> FEATURE:
<223> OTHER INFORMATION: C-terminus

<400> SEQUENCE: 91

Val Lys Val Ser Ser Ala
1               5

<210> SEQ ID NO 92
<211> LENGTH: 6
<212> TYPE: PRT
<213> ORGANISM: Artificial Sequence
<220> FEATURE:
<223> OTHER INFORMATION: C-terminus

<400> SEQUENCE: 92

Val Gln Val Ser Ser Ala
1               5

<210> SEQ ID NO 93
<211> LENGTH: 6
<212> TYPE: PRT
<213> ORGANISM: Artificial Sequence
<220> FEATURE:
<223> OTHER INFORMATION: C-terminus

<400> SEQUENCE: 93

Val Thr Val Lys Ser Ala
1               5

<210> SEQ ID NO 94
<211> LENGTH: 6
<212> TYPE: PRT
<213> ORGANISM: Artificial Sequence
<220> FEATURE:
<223> OTHER INFORMATION: C-terminus

<400> SEQUENCE: 94

Val Thr Val Gln Ser Ala
1               5

<210> SEQ ID NO 95
<211> LENGTH: 6
<212> TYPE: PRT
<213> ORGANISM: Artificial Sequence
<220> FEATURE:
<223> OTHER INFORMATION: C-terminus

<400> SEQUENCE: 95

Val Lys Val Lys Ser Ala
1               5

<210> SEQ ID NO 96
<211> LENGTH: 6
<212> TYPE: PRT
```

```
<213> ORGANISM: Artificial Sequence
<220> FEATURE:
<223> OTHER INFORMATION: C-terminus

<400> SEQUENCE: 96

Val Lys Val Gln Ser Ala
1               5

<210> SEQ ID NO 97
<211> LENGTH: 6
<212> TYPE: PRT
<213> ORGANISM: Artificial Sequence
<220> FEATURE:
<223> OTHER INFORMATION: C-terminus

<400> SEQUENCE: 97

Val Gln Val Lys Ser Ala
1               5

<210> SEQ ID NO 98
<211> LENGTH: 6
<212> TYPE: PRT
<213> ORGANISM: Artificial Sequence
<220> FEATURE:
<223> OTHER INFORMATION: C-terminus

<400> SEQUENCE: 98

Val Gln Val Gln Ser Ala
1               5

<210> SEQ ID NO 99
<211> LENGTH: 4
<212> TYPE: PRT
<213> ORGANISM: Artificial Sequence
<220> FEATURE:
<223> OTHER INFORMATION: Motif from Table X

<400> SEQUENCE: 99

Lys Glu Arg Glu
1

<210> SEQ ID NO 100
<211> LENGTH: 4
<212> TYPE: PRT
<213> ORGANISM: Artificial Sequence
<220> FEATURE:
<223> OTHER INFORMATION: Motif from Table X

<400> SEQUENCE: 100

Lys Gln Arg Glu
1

<210> SEQ ID NO 101
<211> LENGTH: 5
<212> TYPE: PRT
<213> ORGANISM: Artificial Sequence
<220> FEATURE:
<223> OTHER INFORMATION: Motif from Table X

<400> SEQUENCE: 101

Lys Glu Arg Glu Leu
1               5

<210> SEQ ID NO 102
<211> LENGTH: 5
<212> TYPE: PRT
<213> ORGANISM: Artificial Sequence
```

```
<220> FEATURE:
<223> OTHER INFORMATION: Motif from Table X

<400> SEQUENCE: 102

Lys Glu Arg Glu Phe
1               5

<210> SEQ ID NO 103
<211> LENGTH: 5
<212> TYPE: PRT
<213> ORGANISM: Artificial Sequence
<220> FEATURE:
<223> OTHER INFORMATION: Motif from Table X

<400> SEQUENCE: 103

Lys Gln Arg Glu Leu
1               5

<210> SEQ ID NO 104
<211> LENGTH: 5
<212> TYPE: PRT
<213> ORGANISM: Artificial Sequence
<220> FEATURE:
<223> OTHER INFORMATION: Motif from Table X

<400> SEQUENCE: 104

Lys Gln Arg Glu Phe
1               5

<210> SEQ ID NO 105
<211> LENGTH: 5
<212> TYPE: PRT
<213> ORGANISM: Artificial Sequence
<220> FEATURE:
<223> OTHER INFORMATION: Motif from Table X

<400> SEQUENCE: 105

Lys Glu Arg Glu Gly
1               5

<210> SEQ ID NO 106
<211> LENGTH: 5
<212> TYPE: PRT
<213> ORGANISM: Artificial Sequence
<220> FEATURE:
<223> OTHER INFORMATION: Motif from Table X

<400> SEQUENCE: 106

Lys Gln Arg Glu Trp
1               5

<210> SEQ ID NO 107
<211> LENGTH: 5
<212> TYPE: PRT
<213> ORGANISM: Artificial Sequence
<220> FEATURE:
<223> OTHER INFORMATION: Motif from Table X

<400> SEQUENCE: 107

Lys Gln Arg Glu Gly
1               5

<210> SEQ ID NO 108
<211> LENGTH: 4
<212> TYPE: PRT
<213> ORGANISM: Artificial Sequence
<220> FEATURE:
```

```
<223> OTHER INFORMATION: Motif from Table X

<400> SEQUENCE: 108

Thr Glu Arg Glu
1

<210> SEQ ID NO 109
<211> LENGTH: 5
<212> TYPE: PRT
<213> ORGANISM: Artificial Sequence
<220> FEATURE:
<223> OTHER INFORMATION: Motif from Table X

<400> SEQUENCE: 109

Thr Glu Arg Glu Leu
1               5

<210> SEQ ID NO 110
<211> LENGTH: 4
<212> TYPE: PRT
<213> ORGANISM: Artificial Sequence
<220> FEATURE:
<223> OTHER INFORMATION: Motif from Table X

<400> SEQUENCE: 110

Thr Gln Arg Glu
1

<210> SEQ ID NO 111
<211> LENGTH: 5
<212> TYPE: PRT
<213> ORGANISM: Artificial Sequence
<220> FEATURE:
<223> OTHER INFORMATION: Motif from Table X

<400> SEQUENCE: 111

Thr Gln Arg Glu Leu
1               5

<210> SEQ ID NO 112
<211> LENGTH: 4
<212> TYPE: PRT
<213> ORGANISM: Artificial Sequence
<220> FEATURE:
<223> OTHER INFORMATION: Motif from Table X

<400> SEQUENCE: 112

Lys Glu Cys Glu
1

<210> SEQ ID NO 113
<211> LENGTH: 5
<212> TYPE: PRT
<213> ORGANISM: Artificial Sequence
<220> FEATURE:
<223> OTHER INFORMATION: Motif from Table X

<400> SEQUENCE: 113

Lys Glu Cys Glu Leu
1               5

<210> SEQ ID NO 114
<211> LENGTH: 5
<212> TYPE: PRT
<213> ORGANISM: Artificial Sequence
<220> FEATURE:
<223> OTHER INFORMATION: Motif from Table X
```

```
<400> SEQUENCE: 114

Lys Glu Cys Glu Arg
1               5

<210> SEQ ID NO 115
<211> LENGTH: 4
<212> TYPE: PRT
<213> ORGANISM: Artificial Sequence
<220> FEATURE:
<223> OTHER INFORMATION: Motif from Table X

<400> SEQUENCE: 115

Lys Gln Cys Glu
1

<210> SEQ ID NO 116
<211> LENGTH: 5
<212> TYPE: PRT
<213> ORGANISM: Artificial Sequence
<220> FEATURE:
<223> OTHER INFORMATION: Motif from Table X

<400> SEQUENCE: 116

Lys Gln Cys Glu Leu
1               5

<210> SEQ ID NO 117
<211> LENGTH: 4
<212> TYPE: PRT
<213> ORGANISM: Artificial Sequence
<220> FEATURE:
<223> OTHER INFORMATION: Motif from Table X

<400> SEQUENCE: 117

Arg Glu Arg Glu
1

<210> SEQ ID NO 118
<211> LENGTH: 5
<212> TYPE: PRT
<213> ORGANISM: Artificial Sequence
<220> FEATURE:
<223> OTHER INFORMATION: Motif from Table X

<400> SEQUENCE: 118

Arg Glu Arg Glu Gly
1               5

<210> SEQ ID NO 119
<211> LENGTH: 4
<212> TYPE: PRT
<213> ORGANISM: Artificial Sequence
<220> FEATURE:
<223> OTHER INFORMATION: Motif from Table X

<400> SEQUENCE: 119

Arg Gln Arg Glu
1

<210> SEQ ID NO 120
<211> LENGTH: 5
<212> TYPE: PRT
<213> ORGANISM: Artificial Sequence
<220> FEATURE:
<223> OTHER INFORMATION: Motif from Table X
```

```
<400> SEQUENCE: 120

Arg Gln Arg Glu Leu
1               5

<210> SEQ ID NO 121
<211> LENGTH: 5
<212> TYPE: PRT
<213> ORGANISM: Artificial Sequence
<220> FEATURE:
<223> OTHER INFORMATION: Motif from Table X

<400> SEQUENCE: 121

Arg Gln Arg Glu Phe
1               5

<210> SEQ ID NO 122
<211> LENGTH: 5
<212> TYPE: PRT
<213> ORGANISM: Artificial Sequence
<220> FEATURE:
<223> OTHER INFORMATION: Motif from Table X

<400> SEQUENCE: 122

Arg Gln Arg Glu Trp
1               5

<210> SEQ ID NO 123
<211> LENGTH: 4
<212> TYPE: PRT
<213> ORGANISM: Artificial Sequence
<220> FEATURE:
<223> OTHER INFORMATION: Motif from Table X

<400> SEQUENCE: 123

Gln Glu Arg Glu
1

<210> SEQ ID NO 124
<211> LENGTH: 5
<212> TYPE: PRT
<213> ORGANISM: Artificial Sequence
<220> FEATURE:
<223> OTHER INFORMATION: Motif from Table X

<400> SEQUENCE: 124

Gln Glu Arg Glu Gly
1               5

<210> SEQ ID NO 125
<211> LENGTH: 4
<212> TYPE: PRT
<213> ORGANISM: Artificial Sequence
<220> FEATURE:
<223> OTHER INFORMATION: Motif from Table X

<400> SEQUENCE: 125

Gln Gln Arg Glu
1

<210> SEQ ID NO 126
<211> LENGTH: 5
<212> TYPE: PRT
<213> ORGANISM: Artificial Sequence
<220> FEATURE:
<223> OTHER INFORMATION: Motif from Table X

<400> SEQUENCE: 126
```

Gln Gln Arg Glu Trp
1               5

<210> SEQ ID NO 127
<211> LENGTH: 5
<212> TYPE: PRT
<213> ORGANISM: Artificial Sequence
<220> FEATURE:
<223> OTHER INFORMATION: Motif from Table X

<400> SEQUENCE: 127

Gln Gln Arg Glu Leu
1               5

<210> SEQ ID NO 128
<211> LENGTH: 5
<212> TYPE: PRT
<213> ORGANISM: Artificial Sequence
<220> FEATURE:
<223> OTHER INFORMATION: Motif from Table X

<400> SEQUENCE: 128

Gln Gln Arg Glu Phe
1               5

<210> SEQ ID NO 129
<211> LENGTH: 4
<212> TYPE: PRT
<213> ORGANISM: Artificial Sequence
<220> FEATURE:
<223> OTHER INFORMATION: Motif from Table X

<400> SEQUENCE: 129

Lys Gly Arg Glu
1

<210> SEQ ID NO 130
<211> LENGTH: 5
<212> TYPE: PRT
<213> ORGANISM: Artificial Sequence
<220> FEATURE:
<223> OTHER INFORMATION: Motif from Table X

<400> SEQUENCE: 130

Lys Gly Arg Glu Gly
1               5

<210> SEQ ID NO 131
<211> LENGTH: 4
<212> TYPE: PRT
<213> ORGANISM: Artificial Sequence
<220> FEATURE:
<223> OTHER INFORMATION: Motif from Table X

<400> SEQUENCE: 131

Lys Asp Arg Glu
1

<210> SEQ ID NO 132
<211> LENGTH: 5
<212> TYPE: PRT
<213> ORGANISM: Artificial Sequence
<220> FEATURE:
<223> OTHER INFORMATION: Motif from Table X

<400> SEQUENCE: 132

```
Lys Asp Arg Glu Val
1               5

<210> SEQ ID NO 133
<211> LENGTH: 5
<212> TYPE: PRT
<213> ORGANISM: Artificial Sequence
<220> FEATURE:
<223> OTHER INFORMATION: Motif from Table X

<400> SEQUENCE: 133

Asp Glu Cys Lys Leu
1               5

<210> SEQ ID NO 134
<211> LENGTH: 5
<212> TYPE: PRT
<213> ORGANISM: Artificial Sequence
<220> FEATURE:
<223> OTHER INFORMATION: Motif from Table X

<400> SEQUENCE: 134

Asn Val Cys Glu Leu
1               5

<210> SEQ ID NO 135
<211> LENGTH: 4
<212> TYPE: PRT
<213> ORGANISM: Artificial Sequence
<220> FEATURE:
<223> OTHER INFORMATION: Motif from Table X

<400> SEQUENCE: 135

Gly Val Glu Trp
1

<210> SEQ ID NO 136
<211> LENGTH: 4
<212> TYPE: PRT
<213> ORGANISM: Artificial Sequence
<220> FEATURE:
<223> OTHER INFORMATION: Motif from Table X

<400> SEQUENCE: 136

Glu Pro Glu Trp
1

<210> SEQ ID NO 137
<211> LENGTH: 4
<212> TYPE: PRT
<213> ORGANISM: Artificial Sequence
<220> FEATURE:
<223> OTHER INFORMATION: Motif from Table X

<400> SEQUENCE: 137

Gly Leu Glu Arg
1

<210> SEQ ID NO 138
<211> LENGTH: 4
<212> TYPE: PRT
<213> ORGANISM: Artificial Sequence
<220> FEATURE:
<223> OTHER INFORMATION: Motif from Table X

<400> SEQUENCE: 138

Asp Gln Glu Trp
```

```
<210> SEQ ID NO 139
<211> LENGTH: 4
<212> TYPE: PRT
<213> ORGANISM: Artificial Sequence
<220> FEATURE:
<223> OTHER INFORMATION: Motif from Table X

<400> SEQUENCE: 139

Asp Leu Glu Trp
1

<210> SEQ ID NO 140
<211> LENGTH: 4
<212> TYPE: PRT
<213> ORGANISM: Artificial Sequence
<220> FEATURE:
<223> OTHER INFORMATION: Motif from Table X

<400> SEQUENCE: 140

Gly Ile Glu Trp
1

<210> SEQ ID NO 141
<211> LENGTH: 4
<212> TYPE: PRT
<213> ORGANISM: Artificial Sequence
<220> FEATURE:
<223> OTHER INFORMATION: Motif from Table X

<400> SEQUENCE: 141

Glu Leu Glu Trp
1

<210> SEQ ID NO 142
<211> LENGTH: 4
<212> TYPE: PRT
<213> ORGANISM: Artificial Sequence
<220> FEATURE:
<223> OTHER INFORMATION: Motif from Table X

<400> SEQUENCE: 142

Gly Pro Glu Trp
1

<210> SEQ ID NO 143
<211> LENGTH: 4
<212> TYPE: PRT
<213> ORGANISM: Artificial Sequence
<220> FEATURE:
<223> OTHER INFORMATION: Motif from Table X

<400> SEQUENCE: 143

Glu Trp Leu Pro
1

<210> SEQ ID NO 144
<211> LENGTH: 4
<212> TYPE: PRT
<213> ORGANISM: Artificial Sequence
<220> FEATURE:
<223> OTHER INFORMATION: Motif from Table X

<400> SEQUENCE: 144

Gly Pro Glu Arg
1
```

<210> SEQ ID NO 145
<211> LENGTH: 4
<212> TYPE: PRT
<213> ORGANISM: Artificial Sequence
<220> FEATURE:
<223> OTHER INFORMATION: Motif from Table X

<400> SEQUENCE: 145

Gly Leu Glu Arg
1

<210> SEQ ID NO 146
<211> LENGTH: 4
<212> TYPE: PRT
<213> ORGANISM: Artificial Sequence
<220> FEATURE:
<223> OTHER INFORMATION: Motif from Table X

<400> SEQUENCE: 146

Glu Leu Glu Trp
1

<210> SEQ ID NO 147
<211> LENGTH: 515
<212> TYPE: PRT
<213> ORGANISM: Artificial Sequence
<220> FEATURE:
<223> OTHER INFORMATION: F027200927

<400> SEQUENCE: 147

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Gly Gly Gly Ser Gly Gly
        115                 120                 125

Gly Ser Glu Val Gln Leu Val Glu Ser Gly Gly Gly Val Val Gln Pro
    130                 135                 140

Gly Gly Ser Leu Arg Leu Ser Cys Ala Ala Ser Gly Arg Thr Phe Ser
145                 150                 155                 160

Ser Tyr Val Met Gly Trp Phe Arg Gln Ala Pro Gly Lys Glu Arg Glu
                165                 170                 175

Phe Val Ser Thr Ile Asn Trp Ala Gly Ser Arg Gly Tyr Tyr Ala Asp
            180                 185                 190

Ser Val Lys Gly Arg Phe Thr Ile Ser Arg Asp Asn Ala Lys Asn Thr
        195                 200                 205

Val Tyr Leu Gln Met Asn Ser Leu Arg Pro Glu Asp Thr Ala Leu Tyr
    210                 215                 220

Tyr Cys Ala Ala Ser Ala Gly Gly Phe Leu Val Pro Arg Val Gly Gln
225                 230                 235                 240

Gly Tyr Asp Tyr Trp Gly Gln Gly Thr Leu Val Thr Val Ser Ser Gly
            245                 250                 255

Gly Gly Gly Ser Gly Gly Gly Ser Glu Val Gln Leu Val Glu Ser Gly
        260                 265                 270

Gly Gly Val Val Gln Pro Gly Gly Ser Leu Arg Leu Ser Cys Ala Ala
        275                 280                 285

Ser Gly Phe Thr Phe Arg Ser Phe Gly Met Ser Trp Val Arg Gln Ala
    290                 295                 300

Pro Gly Lys Gly Pro Glu Trp Val Ser Ser Ile Ser Gly Ser Gly Ser
305                 310                 315                 320

Asp Thr Leu Tyr Ala Asp Ser Val Lys Gly Arg Phe Thr Ile Ser Arg
            325                 330                 335

Asp Asn Ser Lys Asn Thr Leu Tyr Leu Gln Met Asn Ser Leu Arg Pro
        340                 345                 350

Glu Asp Thr Ala Leu Tyr Tyr Cys Thr Ile Gly Gly Ser Leu Ser Arg
        355                 360                 365

Ser Ser Gln Gly Thr Leu Val Thr Val Ser Ser Gly Gly Gly Gly Ser
    370                 375                 380

Gly Gly Gly Ser Glu Val Gln Leu Val Glu Ser Gly Gly Gly Val Val
385                 390                 395                 400

Gln Pro Gly Gly Ser Leu Arg Leu Ser Cys Ala Ala Ser Gly Phe Ser
            405                 410                 415

Leu Asp Tyr Tyr Gly Val Gly Trp Phe Arg Gln Ala Pro Gly Lys Glu
        420                 425                 430

Arg Glu Gly Val Ser Cys Ile Ser Ser Glu Gly Asp Thr Tyr Tyr
        435                 440                 445

Ala Asp Ser Val Lys Gly Arg Phe Thr Ile Ser Arg Asp Asn Ala Lys
450                 455                 460

Asn Thr Val Tyr Leu Gln Met Asn Ser Leu Arg Pro Glu Asp Thr Ala
465                 470                 475                 480

Leu Tyr Tyr Cys Ala Thr Asp Leu Ser Asp Tyr Gly Val Cys Ser Arg
            485                 490                 495

Trp Pro Ser Pro Tyr Asp Tyr Trp Gly Gln Gly Thr Leu Val Lys Val
        500                 505                 510

Ser Ser Ala
    515

<210> SEQ ID NO 148
<211> LENGTH: 125
<212> TYPE: PRT
<213> ORGANISM: Artificial Sequence
<220> FEATURE:
<223> OTHER INFORMATION: 10A06

<400> SEQUENCE: 148

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Pro Gly Lys Glu Arg Glu Phe Val
        35                  40                  45

Ser Thr Ile Asn Trp Ala Gly Ser Arg Gly Tyr Tyr Ala Asp Ser Val
    50                  55                  60

```
Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Ser Ala Gly Gly Phe Leu Val Pro Arg Val Gly Gln Gly Tyr
            100                 105                 110

Asp Tyr Trp Gly Gln Gly Thr Leu Val Thr Val Ser Ser
        115                 120                 125

<210> SEQ ID NO 149
<211> LENGTH: 126
<212> TYPE: PRT
<213> ORGANISM: Artificial Sequence
<220> FEATURE:
<223> OTHER INFORMATION: 7G09

<400> SEQUENCE: 149

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Ser Leu Asp Tyr Tyr
                 20                  25                  30

Gly Val Gly Trp Phe Arg Gln Ala Pro Gly Lys Glu Arg Glu Gly Val
            35                  40                  45

Ser Cys Ile Ser Ser Ser Glu Gly Asp Thr Tyr Tyr Ala Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Thr Asp Leu Ser Asp Tyr Val Cys Ser Arg Trp Pro Ser Pro
            100                 105                 110

Tyr Asp Tyr Trp Gly Gln Gly Thr Leu Val Lys Val Ser Ser
        115                 120                 125

<210> SEQ ID NO 150
<211> LENGTH: 10
<212> TYPE: PRT
<213> ORGANISM: Artificial Sequence
<220> FEATURE:
<223> OTHER INFORMATION: CDR1

<400> SEQUENCE: 150

Gly Arg Thr Phe Ser Ser Tyr Val Met Gly
 1               5                  10

<210> SEQ ID NO 151
<211> LENGTH: 10
<212> TYPE: PRT
<213> ORGANISM: Artificial Sequence
<220> FEATURE:
<223> OTHER INFORMATION: CDR2

<400> SEQUENCE: 151

Thr Ile Asn Trp Ala Gly Ser Arg Gly Tyr
 1               5                  10

<210> SEQ ID NO 152
<211> LENGTH: 16
<212> TYPE: PRT
<213> ORGANISM: Artificial Sequence
<220> FEATURE:
<223> OTHER INFORMATION: CDR3
```

```
<400> SEQUENCE: 152

Ser Ala Gly Gly Phe Leu Val Pro Arg Val Gly Gln Gly Tyr Asp Tyr
1               5                   10                  15

<210> SEQ ID NO 153
<211> LENGTH: 10
<212> TYPE: PRT
<213> ORGANISM: Artificial Sequence
<220> FEATURE:
<223> OTHER INFORMATION: CDR1

<400> SEQUENCE: 153

Gly Phe Ser Leu Asp Tyr Tyr Gly Val Gly
1               5                   10

<210> SEQ ID NO 154
<211> LENGTH: 10
<212> TYPE: PRT
<213> ORGANISM: Artificial Sequence
<220> FEATURE:
<223> OTHER INFORMATION: CDR2

<400> SEQUENCE: 154

Cys Ile Ser Ser Ser Glu Gly Asp Thr Tyr
1               5                   10

<210> SEQ ID NO 155
<211> LENGTH: 17
<212> TYPE: PRT
<213> ORGANISM: Artificial Sequence
<220> FEATURE:
<223> OTHER INFORMATION: CDR3

<400> SEQUENCE: 155

Asp Leu Ser Asp Tyr Gly Val Cys Ser Arg Trp Pro Ser Pro Tyr Asp
1               5                   10                  15

Tyr

<210> SEQ ID NO 156
<211> LENGTH: 14
<212> TYPE: PRT
<213> ORGANISM: Artificial Sequence
<220> FEATURE:
<223> OTHER INFORMATION: FR2

<400> SEQUENCE: 156

Trp Phe Arg Gln Ala Pro Gly Lys Glu Arg Glu Phe Val Ser
1               5                   10

<210> SEQ ID NO 157
<211> LENGTH: 39
<212> TYPE: PRT
<213> ORGANISM: Artificial Sequence
<220> FEATURE:
<223> OTHER INFORMATION: FR3

<400> SEQUENCE: 157

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Arg Pro Glu Asp Thr
            20                  25                  30

Ala Leu Tyr Tyr Cys Ala Thr
        35
```

```
<210> SEQ ID NO 158
<211> LENGTH: 505
<212> TYPE: PRT
<213> ORGANISM: Artificial Sequence
<220> FEATURE:
<223> OTHER INFORMATION: F027200925

<400> SEQUENCE: 158
```

Asp Val Gln Leu Val Glu Ser Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Tyr Trp Gly
            100                 105                 110

Gln Gly Thr Leu Val Thr Val Ser Ser Gly Gly Gly Ser Gly Gly
        115                 120                 125

Gly Ser Glu Val Gln Leu Val Glu Ser Gly Gly Val Val Gln Pro
130                 135                 140

Gly Gly Ser Leu Arg Leu Ser Cys Ala Ala Ser Gly Ile Ile Phe Ser
145                 150                 155                 160

Ile Asn Ala Met Gly Trp Tyr Arg Gln Ala Pro Gly Lys Gln Arg Glu
                165                 170                 175

Leu Val Ala Asp Ile Phe Pro Phe Gly Ser Thr Glu Tyr Ala Asp Ser
            180                 185                 190

Val Lys Gly Arg Phe Thr Ile Ser Arg Asp Asn Ala Lys Asn Thr Val
        195                 200                 205

Tyr Leu Gln Met Asn Ser Leu Arg Pro Glu Asp Thr Ala Leu Tyr Tyr
    210                 215                 220

Cys His Ser Tyr Asp Pro Arg Gly Asp Tyr Trp Gly Gln Gly Thr
225                 230                 235                 240

Leu Val Thr Val Ser Ser Gly Gly Gly Ser Gly Gly Ser Glu
            245                 250                 255

Val Gln Leu Val Glu Ser Gly Gly Val Val Gln Pro Gly Gly Ser
        260                 265                 270

Leu Arg Leu Ser Cys Ala Ala Ser Gly Phe Thr Phe Arg Ser Phe Gly
    275                 280                 285

Met Ser Trp Val Arg Gln Ala Pro Gly Lys Gly Pro Glu Trp Val Ser
290                 295                 300

Ser Ile Ser Gly Ser Gly Ser Asp Thr Leu Tyr Ala Asp Ser Val Lys
305                 310                 315                 320

Gly Arg Phe Thr Ile Ser Arg Asp Asn Ser Lys Asn Thr Leu Tyr Leu
                325                 330                 335

Gln Met Asn Ser Leu Arg Pro Glu Asp Thr Ala Leu Tyr Tyr Cys Thr
            340                 345                 350

Ile Gly Gly Ser Leu Ser Arg Ser Ser Gln Gly Thr Leu Val Thr Val
        355                 360                 365

```
Ser Ser Gly Gly Gly Ser Gly Gly Gly Ser Glu Val Gln Leu Val
    370             375             380

Glu Ser Gly Gly Gly Val Val Gln Pro Gly Gly Ser Leu Arg Leu Ser
385             390             395             400

Cys Ala Ala Ser Gly Arg Thr Phe Ser Ser Tyr Val Met Gly Trp Phe
            405             410             415

Arg Gln Ala Pro Gly Lys Glu Arg Glu Phe Val Ser Thr Ile Asn Trp
            420             425             430

Ala Gly Ser Arg Gly Tyr Tyr Ala Asp Ser Val Lys Gly Arg Phe Thr
            435             440             445

Ile Ser Arg Asp Asn Ala Lys Asn Thr Val Tyr Leu Gln Met Asn Ser
450             455             460

Leu Arg Pro Glu Asp Thr Ala Leu Tyr Tyr Cys Ala Ala Ser Ala Gly
465             470             475             480

Gly Phe Leu Val Pro Arg Val Gly Gln Gly Tyr Asp Tyr Trp Gly Gln
            485             490             495

Gly Thr Leu Val Lys Val Ser Ser Ala
            500             505
```

<210> SEQ ID NO 159
<211> LENGTH: 116
<212> TYPE: PRT
<213> ORGANISM: Artificial Sequence
<220> FEATURE:
<223> OTHER INFORMATION: 6B06

<400> SEQUENCE: 159

```
Glu Val Gln Leu Val Glu Ser Gly Gly Gly Val Val Gln Pro Gly Gly
1               5                   10                  15

Ser Leu Arg Leu Ser Cys Ala Ala Ser Gly Ile Ile Phe Ser Ile Asn
            20                  25                  30

Ala Met Gly Trp Tyr Arg Gln Ala Pro Gly Lys Gln Arg Glu Leu Val
        35                  40                  45

Ala Asp Ile Phe Pro Phe Gly Ser Thr Glu Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Leu Tyr Tyr Cys His
                85                  90                  95

Ser Tyr Asp Pro Arg Gly Asp Asp Tyr Trp Gly Gln Gly Thr Leu Val
            100                 105                 110

Thr Val Ser Ser
        115
```

<210> SEQ ID NO 160
<211> LENGTH: 10
<212> TYPE: PRT
<213> ORGANISM: Artificial Sequence
<220> FEATURE:
<223> OTHER INFORMATION: CDR1

<400> SEQUENCE: 160

```
Gly Ile Ile Phe Ser Ile Asn Ala Met Gly
1               5                   10
```

<210> SEQ ID NO 161
<211> LENGTH: 9
<212> TYPE: PRT
<213> ORGANISM: Artificial Sequence

```
<220> FEATURE:
<223> OTHER INFORMATION: CDR2

<400> SEQUENCE: 161

Asp Ile Phe Pro Phe Gly Ser Thr Glu
1               5

<210> SEQ ID NO 162
<211> LENGTH: 8
<212> TYPE: PRT
<213> ORGANISM: Artificial Sequence
<220> FEATURE:
<223> OTHER INFORMATION: CDR3

<400> SEQUENCE: 162

Tyr Asp Pro Arg Gly Asp Asp Tyr
1               5

<210> SEQ ID NO 163
<211> LENGTH: 14
<212> TYPE: PRT
<213> ORGANISM: Artificial Sequence
<220> FEATURE:
<223> OTHER INFORMATION: FR2

<400> SEQUENCE: 163

Trp Tyr Arg Gln Ala Pro Gly Lys Gln Arg Glu Leu Val Ala
1               5                   10

<210> SEQ ID NO 164
<211> LENGTH: 39
<212> TYPE: PRT
<213> ORGANISM: Artificial Sequence
<220> FEATURE:
<223> OTHER INFORMATION: FR3

<400> SEQUENCE: 164

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Arg Pro Glu Asp Thr
            20                  25                  30

Ala Leu Tyr Tyr Cys His Ser
        35

<210> SEQ ID NO 165
<211> LENGTH: 5
<212> TYPE: PRT
<213> ORGANISM: Artificial Sequence
<220> FEATURE:
<223> OTHER INFORMATION: CDR1

<400> SEQUENCE: 165

Ser Tyr Val Met Gly
1               5

<210> SEQ ID NO 166
<211> LENGTH: 17
<212> TYPE: PRT
<213> ORGANISM: Artificial Sequence
<220> FEATURE:
<223> OTHER INFORMATION: CDR2

<400> SEQUENCE: 166

Thr Ile Asn Trp Ala Gly Ser Arg Gly Tyr Tyr Ala Asp Ser Val Lys
1               5                   10                  15
```

-continued

Gly

<210> SEQ ID NO 167
<211> LENGTH: 5
<212> TYPE: PRT
<213> ORGANISM: Artificial Sequence
<220> FEATURE:
<223> OTHER INFORMATION: CDR1

<400> SEQUENCE: 167

Tyr Tyr Gly Val Gly
1               5

<210> SEQ ID NO 168
<211> LENGTH: 17
<212> TYPE: PRT
<213> ORGANISM: Artificial Sequence
<220> FEATURE:
<223> OTHER INFORMATION: CDR2

<400> SEQUENCE: 168

Cys Ile Ser Ser Ser Glu Gly Asp Thr Tyr Tyr Ala Asp Ser Val Lys
1               5                   10                  15

Gly

<210> SEQ ID NO 169
<211> LENGTH: 30
<212> TYPE: PRT
<213> ORGANISM: Artificial Sequence
<220> FEATURE:
<223> OTHER INFORMATION: FR1

<400> SEQUENCE: 169

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ser Leu Asp
                20                  25                  30

<210> SEQ ID NO 170
<211> LENGTH: 32
<212> TYPE: PRT
<213> ORGANISM: Artificial Sequence
<220> FEATURE:
<223> OTHER INFORMATION: FR3

<400> SEQUENCE: 170

Arg Phe Thr Ile Ser Arg Asp Asn Ala Lys Asn Thr Val Tyr Leu Gln
1               5                   10                  15

Met Asn Ser Leu Arg Pro Glu Asp Thr Ala Leu Tyr Tyr Cys Ala Thr
                20                  25                  30

<210> SEQ ID NO 171
<211> LENGTH: 5
<212> TYPE: PRT
<213> ORGANISM: Artificial Sequence
<220> FEATURE:
<223> OTHER INFORMATION: CDR1

<400> SEQUENCE: 171

Ile Asn Ala Met Gly
1               5

<210> SEQ ID NO 172
<211> LENGTH: 16
<212> TYPE: PRT

```
<213> ORGANISM: Artificial Sequence
<220> FEATURE:
<223> OTHER INFORMATION: CDR2

<400> SEQUENCE: 172

Asp Ile Phe Pro Phe Gly Ser Thr Glu Tyr Ala Asp Ser Val Lys Gly
1               5                   10                  15

<210> SEQ ID NO 173
<211> LENGTH: 30
<212> TYPE: PRT
<213> ORGANISM: Artificial Sequence
<220> FEATURE:
<223> OTHER INFORMATION: FR1

<400> SEQUENCE: 173

Glu Val Gln Leu Val Glu Ser Gly Gly Gly Val Val Gln Pro Gly Gly
1               5                   10                  15

Ser Leu Arg Leu Ser Cys Ala Ala Ser Gly Ile Ile Phe Ser
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: FR3

<400> SEQUENCE: 174

Arg Phe Thr Ile Ser Arg Asp Asn Ala Lys Asn Thr Val Tyr Leu Gln
1               5                   10                  15

Met Asn Ser Leu Arg Pro Glu Asp Thr Ala Leu Tyr Tyr Cys His Ser
            20                  25                  30

<210> SEQ ID NO 175
<211> LENGTH: 30
<212> TYPE: PRT
<213> ORGANISM: Artificial Sequence
<220> FEATURE:
<223> OTHER INFORMATION: FR1

<400> SEQUENCE: 175

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ser Leu Asp
            20                  25                  30

<210> SEQ ID NO 176
<211> LENGTH: 124
<212> TYPE: PRT
<213> ORGANISM: Artificial Sequence
<220> FEATURE:
<223> OTHER INFORMATION: F027200921

<400> SEQUENCE: 176

Asp Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Asn Tyr
            20                  25                  30

Ala Met Ala Trp Phe Arg Gln Ala Pro Gly Lys Glu Arg Glu Phe Val
        35                  40                  45

Ala Val Ile Ser Tyr Ala Gly Gly Arg Thr Tyr Tyr Ala Asp Ser Val
    50                  55                  60
```

```
Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Val Asp Ser Pro Leu Ile Ala Thr His Pro Arg Gly Tyr Asp
                100                 105                 110

Tyr Trp Gly Gln Gly Thr Leu Val Thr Val Ser Ser
            115                 120

<210> SEQ ID NO 177
<211> LENGTH: 128
<212> TYPE: PRT
<213> ORGANISM: Artificial Sequence
<220> FEATURE:
<223> OTHER INFORMATION: F027201040

<400> SEQUENCE: 177

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Leu Ala Tyr Tyr
                 20                  25                  30

Ala Ile Gly Trp Phe Arg Gln Ala Pro Gly Lys Glu Arg Glu Gly Val
             35                  40                  45

Ser Cys Ile Ser Gly Ser Val Gly Thr Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Leu Tyr Tyr Cys
                 85                  90                  95

Val Arg Ser Ser Trp Phe Asp Cys Gly Val Gln Gly Arg Asp Leu Gly
                100                 105                 110

Asn Glu Tyr Asp Tyr Arg Gly Gln Gly Thr Leu Val Thr Val Ser Ser
            115                 120                 125
```